US012754258B2

(12) United States Patent
Sharma et al.

(10) Patent No.: US 12,754,258 B2
(45) Date of Patent: Oct. 6, 2026

(54) THREE-DIMENSIONAL ON-CHIP MAGNETIC SENSOR FOR OSCILLATING MAGNETIC FIELDS

(71) Applicant: California Institute of Technology, Pasadena, CA (US)

(72) Inventors: Saransh Sharma, Pasadena, CA (US); Hayward Melton, Hinsdale, IL (US); Azita Emami, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 59 days.

(21) Appl. No.: 18/430,936

(22) Filed: Feb. 2, 2024

(65) Prior Publication Data

US 2024/0264247 A1 Aug. 8, 2024

Related U.S. Application Data

(60) Provisional application No. 63/443,592, filed on Feb. 6, 2023, provisional application No. 63/443,576, filed on Feb. 6, 2023.

(51) Int. Cl.
*G01R 33/02* (2006.01)
*A61B 5/06* (2006.01)
*G01R 33/028* (2006.01)

(52) U.S. Cl.
CPC .......... *G01R 33/0286* (2013.01); *A61B 5/062* (2013.01); *G01R 33/0206* (2013.01)

(58) Field of Classification Search
CPC .............. G01R 33/0286; G01R 33/383; G01R 33/3835; G01R 33/0206; A61B 5/062
See application file for complete search history.

(56) References Cited

U.S. PATENT DOCUMENTS 6,414,564 B1 7/2002 Mizoguchi et al.
9,915,641 B2 3/2018 Shapiro et al.
(Continued)

FOREIGN PATENT DOCUMENTS

JP 10199724 A 7/1998
JP 2014166306 A 9/2014
(Continued)

OTHER PUBLICATIONS

W. M. Ricci et al., "Intramedullary Nailing of Femoral Shaft Fractures: Current Concepts," JAAOS, 2009, pp. 296-305, vol. 17, No. 5.
(Continued)

*Primary Examiner* — Lee E Rodak
*Assistant Examiner* — Taqi R Nasir
(74) *Attorney, Agent, or Firm* — Intrinsic Law Corp.

(57) ABSTRACT

A three-dimensional on-chip magnetic sensor includes first, second, and third coils. The first and second coils include respective planar spirals formed by metal layers and metal vias. Each planar spiral of the first coil includes first interconnected loops wound about a first axis, where neighboring first planar spirals are electrically connected to each other. Each planar spiral of the second coil includes second interconnected loops wound about a second axis, where neighboring second planar spirals are electrically connected to each other. The third coil has a planar spiral includes third interconnected loops that are wound about a third axis. Each electrically conductive coil is configured to produce a respective electromagnetic force (EMF) induced by an oscillating magnetic field, the respective EMF driving a respective alternating current (AC) through the respective readout circuit. Each readout circuit is configured to detect a respective peak voltage magnitude of the respective AC.

20 Claims, 44 Drawing Sheets

(56) References Cited

U.S. PATENT DOCUMENTS

| | | | | |
|---|---|---|---|---|
| 10,466,277 | B1 | 11/2019 | Brooks | |
| 10,788,546 | B2 | 9/2020 | Bilbao De | |
| 11,457,835 | B2 | 10/2022 | Sharma et al. | |
| 11,944,423 | B2 | 4/2024 | Sharma et al. | |
| 2010/0156399 | A1 | 6/2010 | Chiba et al. | |
| 2011/0009697 | A1 | 1/2011 | Kawano et al. | |
| 2013/0303878 | A1 | 11/2013 | Nevo et al. | |
| 2014/0167762 | A1 | 6/2014 | Sugiyama | |
| 2015/0022193 | A1 * | 1/2015 | Burdette ................ | G01R 33/06 324/239 |
| 2015/0297065 | A1 | 10/2015 | Park et al. | |
| 2015/0308810 | A1 | 10/2015 | Gilmore | |
| 2016/0022123 | A1 | 1/2016 | Katznelson et al. | |
| 2016/0199832 | A1 * | 7/2016 | Jamshidi ............. | B01F 33/3021 204/600 |
| 2016/0278662 | A1 | 9/2016 | Brister et al. | |
| 2019/0335983 | A1 | 11/2019 | Duan | |
| 2019/0388105 | A1 | 12/2019 | Sharma et al. | |
| 2020/0271733 | A1 * | 8/2020 | Jourdan ............... | G01R 33/022 |
| 2020/0348378 | A1 | 11/2020 | Alford et al. | |
| 2021/0141034 | A1 * | 5/2021 | Sharma .................... | A61B 5/05 |
| 2022/0022349 | A1 | 1/2022 | Ramachandran et al. | |
| 2022/0308128 | A1 | 9/2022 | Endo et al. | |

FOREIGN PATENT DOCUMENTS

| | | | |
|---|---|---|---|
| KR | 1020220032064 | A | 3/2022 |
| WO | 2021097211 | A1 | 5/2021 |

OTHER PUBLICATIONS

A. Wang et al., "Wireless Capsule Endoscopy," Technology Status Evalutation Reports, 2013, pp. 805-815, vol. 78, No. 6, Elsevier.

U. Mezger et al., "Navigation in surgery," Langenbeck's Archives of Surgery, 2013, pp. 501-514, vol. 398, No. 4, Springer.

H. M. Kremers et al., "Prevalence of Total Hip and Knee Replacement in the United States," The Journal of bone and joint surgery. American vol. 2015, pp. 1386-1397, vol. 97, No. 17, The Journal of Bone and Joint Surgery, Incorporated.

D. Vasisht et al., "In-body backscatter communication and localization," Proceedings of the 2018 Conference of the ACM Special Interest Group on Data Communication (SIGCOMM '18). Association for Computing Machinery, Aug. 2018, pp. 132-146, New York, NY, USA.

A. L. Simpson et al., "Comparison Study of Intraoperative Surface Acquisition Methods for Surgical Navigation," IEEE Transactions on Biomedical Engineering, 2013, pp. 1090-1099, vol. 60, No. 4, IEEE.

D. Formica et al., "Biological effects of exposure to magnetic resonance imaging: an overview," BioMedical Eng. OnLine, 2004, pp. 1-12, vol. 3, No. 11, BioMed Central Ltd.

V. Grover et al., "Magnetic Resonance Imaging: Principles and Techniques: Lessons for Clinicians," Journal of Clinical and Experimental Hepatology, 2015, pp. 246-255, vol. 5, No. 3, Elsevier Inc.

M. Monge et al., "Localization of microscale devices in vivo using addressable transmitters operated as magnetic spins," Nature Biomedical Engineering, 2017, vol. 6, pp. 736-744, Springer Nature Limited.

J. Marques et al., "Low-Field MRI: An MR Physics Perspective," Journal of Magnetic Resonance Imaging, 2019, pp. 1528-1542, vol. 49, No. 6, Wiley Online Library.

D. Son et al., "A 5-D Localization Method for a Magnetically Manipulated Untethered Robot using a 2-D Array of Hall-effect Sensors," IEEE/ASME Transactions on Mechatronics, 2016, pp. 708-716, vol. 21, No. 2, IEEE.

A. Emami et al., "MRI-Inspired High-Resolution Localization for Biomedical Applications: Artificial Nuclear Spins on a Chip," IEEE Solid-State Circuits Magazine, 2018, pp. 34-42, vol. 10, No. 4, IEEE.

Rao et al., "Evaluation of gastrointestinal transit in clinical practice: position paper of the American and European Neurogastroenterology and Motility Societies", Neurogastroenterology & Motility, 2011, vol. 23, 8-23, Blackwell Publishing Ltd.

Hoffman et al., "Gastrointestinal Motility Monitor (GIMM)," Journal of Visualized Experiments, 2010, pp. 1-3, vol. 1, No. 46, JOVE.

Keller et al., "Advances in the diagnosis and classification of gastric and intestinal motility disorders," Nature Reviews, Gastroenterology & Hepatology, 2018, pp. 291-308, vol. 15, Springer Nature Limited.

Medtronic, "SmartPill Motility Testing System", Motility Testing, https://www.medtronic.com/covidien/en-us/products/motility-testing/smartpill-motility-testing-system.html#smartpill-motility-capsule.

Lo et al., "A Wireless Implant for Gastrointestinal Motility Disorders," Micromachines, 2018, pp. 1-13, vol. 9, No. 17, MDPI.

T. Leloup et al., "A Novel Technique for Distal Locking of Intramedullary Nail Based on Two Non-constrained Fluoroscopic Images and Navigation," IEEE Trans. Med. Imaging, 2008, pp. 1202-1212, vol. 27, No. 9, IEEE.

A. M. Franz et al., "Electromagnetic Tracking in Medicine—A Review of Technology, Validation, and Applications," IEEE Trans. Med. Imaging, Aug. 2014, pp. 1702-1725, vol. 33, No. 8, IEEE.

F. Chen et al., "3D Catheter Shape Determination for Endovascular Navigation Using a Two-Step Particle Filter and Ultrasound Scanning," IEEE Trans. Med. Imaging, 2017, pp. 685-695, vol. 36, No. 3, IEEE.

F. Parent et al., "Intra-Arterial Image Guidance With Optical Frequency Domain Reflectometry Shape Sensing," IEEE Trans. Med. Imaging, 2019, pp. 482-492, vol. 38, No. 2, IEEE.

M. M. Ahmadi et al., "A Wireless-Implantable Microsystem for Continuous Blood Glucose Monitoring," IEEE Transactions on Biomedical Circuits and Systems, 2009, pp. 169-180, vol. 3, No. 3, IEEE.

ISA, "International Search Report", PCT/US20/60433, Mar. 9, 2021.

ISA, "International Search Report", PCT/US20/60420, Mar. 9, 2021.

ISA, "International Search Report", PCT/US2024/014156, Jun. 3, 2024.

ISA, "International Search Report", PCT/US2024/014169, Jun. 5, 2024.

First Office Action for CN Patent App. No. 202080079140.6, dated Apr. 12, 2025.

* cited by examiner

3800

Input – $B_{xi}, B_{yi}, B_{zi}$

Step 1 – Search for $B_{xi}$ in Main LUT and create LUT-X with all values within $\pm\Delta B$.

Step 2 – Search for $B_{yi}$ in LUT-X and create LUT-Y with all values within $\pm\Delta B$.

Step 3 – Search for $B_{zi}$ in LUT-Y and create LUT-Z with all values within $\pm\Delta B$.

Step 4 – Output the closest $x_i, y_i, z_i$ in LUT-Z.

Output – $x_i, y_i, z_i$

THREE-DIMENSIONAL ON-CHIP MAGNETIC SENSOR FOR OSCILLATING MAGNETIC FIELDS

CROSS-REFERENCE TO RELATED APPLICATIONS

This application claims priority to U.S. Provisional Application No. 63/443,576, titled "Spatial Encoding Using AC Magnetic Field Gradients for Localization of Microdevices," filed on Feb. 6, 2023 and to U.S. Provisional Application No. 63/443,592, titled "Monolithic 3D Sensor in CMOS for AC Field Sensing by Electromagnetic Induction," filed on Feb. 6, 2023, which are hereby incorporated by reference.

STATEMENT REGARDING FEDERALLY-SPONSORED RESEARCH

This invention was made with government support under Grant No. CBET1823036 awarded by the National Science Foundation. The government has certain rights in the invention.

TECHNICAL FIELD

This application relates generally magnetic sensors for three-dimensional localization using oscillating magnetic field gradients produced with alternating current.

BACKGROUND

Magnetic sensors have become increasingly ubiquitous as they constitute an integral part of several fast-growing sectors such as automotive, navigation, robotics, medical devices, power grids, industrial applications, consumer electronics, and space equipment. Examples of magnetic sensors that have been developed for these applications include Hall sensors, semiconducting magneto-resistors, fluxgate sensors, resonant sensors, induction-based magnetometers, and superconducting quantum interference devices (SQUID).

Due to their compatibility with standard low-cost complementary metal-oxide-semiconductor (CMOS) manufacturing processes, Hall sensors are one of the most widely used types of magnetic sensors. More recently, Hall sensors have been used for magnetic gradient based navigation and tracking of miniaturized devices in different biomedical applications. However, one of the key challenges of CMOS-based Hall sensors is their relatively low sensitivity due to the low Hall coefficient of silicon. To achieve better sensitivity, Hall sensors need to be biased at higher current levels, which hinders their widescale use in low-power bioelectronics and other power-constrained applications. Another challenge is the difficulty in implementing high-sensitivity 3D Hall sensors using standard CMOS manufacturing processes. This is often overcome by using ferromagnetic materials that require additional and expensive steps during fabrication, thus increasing complexity and cost.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages, and novel features of the disclosure will be set forth in the following detailed description of the disclosure when considered in conjunction with the drawings, which are intended to illustrate, not limit, the invention.

An aspect of the invention is directed to a three-dimensional on-chip magnetic sensor comprising a semiconductor chip having a semiconductor substrate; a plurality of metal layers disposed on the semiconductor substrate; a plurality of insulator layers disposed on the semiconductor substrate, each insulator layer disposed between a pair of neighboring metal layers to form an alternating arrangement of metal layers and insulator layers; a plurality of metal vias defined in the insulator layers, each metal via electrically connecting a respective pair of neighboring metal layers; and a first electrically conductive coil having a plurality of first planar spirals formed by the metal layers and the metal vias, each first planar spiral including a plurality of first interconnected loops wound about a first axis, wherein neighboring first planar spirals are electrically connected to each other; a second electrically conductive coil having a plurality of second planar spirals formed by the metal layers and the metal vias, each second planar spiral including a plurality of second interconnected loops wound about a second axis that is orthogonal to the first axis, wherein neighboring first planar spirals are electrically connected to each other; a third electrically conductive coil having a third planar spiral formed by at least some of the metal layers and at least some of the metal vias, the third planar spiral including a plurality of third interconnected loops that are wound about a third axis that is orthogonal to the first and second axes, the metal layers spaced apart along the third axis; and a respective readout circuit electrically coupled to a respective electrically conductive coil, the respective readout circuit disposed in the semiconductor chip, wherein each electrically conductive coil is configured to produce a respective electromagnetic force (EMF) induced by an oscillating magnetic field, the respective EMF driving a respective alternating current (AC) through the respective readout circuit, and each readout circuit is configured to detect a respective peak voltage magnitude of the respective AC.

In one or more embodiments, the respective readout circuit comprises a respective amplifier and filter circuit electrically coupled having an input coupled to the respective electrically conductive coil; a respective peak-detect-and-hold (PDH) circuit having an input coupled to an output of the respective amplifier and filter circuit; and a respective analog-to-digital converter (ADC) having an input coupled to an output of the respective peak-detect-and-hold circuit. In one or more embodiments, the respective amplifier and filter circuit includes a band-pass filter having an output coupled to an input of a programmable gain amplifier. In one or more embodiments, the respective PDH circuit includes a respective positive differential PDH circuit and a respective negative differential PDH. In one or more embodiments, the respective ADC comprises a respective differential-input successive approximation register (SAR) ADC.

In one or more embodiments, a catheter is attached to the three-dimensional on-chip magnetic sensor. In one or more embodiments, a guidewire is attached to the three-dimensional on-chip magnetic sensor.

Another aspect of the invention is directed to a system for three-dimensional (3D) localization using oscillating magnetic field gradients, comprising a 3D magnetic field gradient generator; and a 3D on-chip magnetic sensor. The 3D magnetic field gradient generator comprises a first planar electromagnet coil set configured to produce a first oscillating magnetic field gradient with respect to a first axis; a second planar electromagnet coil set configured to produce a second oscillating magnetic field gradient with respect to a second axis that is orthogonal to the first axis; a third planar electromagnet coil set configured to produce a third oscillating magnetic field gradient with respect to a third axis that is orthogonal to the first and second axes, the first, second, and third planar electromagnet coil sets vertically arranged with respect to the third axis; and a controller configured to selectively provide alternating-current (AC) power to the first planar electromagnet coil set, to the second planar electromagnet coil set, and/or to the third planar electromagnet coil set to sequentially produce a respective oscillating localization magnetic field gradient with respect to each of the first, second, and third axes, at least a portion of each oscillating localization magnetic field gradient having a monotonically-varying peak magnetic field magnitude along a respective axis that uniquely encodes a relative position along a respective axis. The 3D on-chip magnetic sensor comprises a semiconductor chip having a semiconductor substrate; a plurality of metal layers disposed on the semiconductor substrate; a plurality of insulator layers disposed on the semiconductor substrate, each insulator layer disposed between a pair of neighboring metal layers to form an alternating arrangement of metal layers and insulator layers; a plurality of metal vias defined in the insulator layers, each metal via electrically connecting a respective pair of neighboring metal layers; a first electrically conductive coil having a plurality of first planar spirals formed by the metal layers and the metal vias, each first planar spiral including a plurality of first interconnected loops wound about a first chip axis, wherein neighboring first planar spirals are electrically connected to each other; a second electrically conductive coil having a plurality of second planar spirals formed by the metal layers and the metal vias, each second planar spiral including a plurality of second interconnected loops wound about a second chip axis that is orthogonal to the first chip axis, wherein neighboring first planar spirals are electrically connected to each other; a third electrically conductive coil having a third planar spiral formed by at least some of the metal layers and at least some of the metal vias, the third planar spiral including a plurality of third interconnected loops that are wound about a third chip axis that is orthogonal to the first and second chip axes, the metal layers spaced apart along the third chip axis; and a respective readout circuit electrically coupled to a respective electrically conductive coil, the respective readout circuit disposed in the semiconductor chip. Each electrically conductive coil is configured to produce a respective electromagnetic force (EMF) induced by each oscillating localization magnetic field gradient, the respective EMF driving a respective sensor AC through the respective readout circuit. Each readout circuit is configured to detect a respective peak voltage magnitude of the respective sensor AC, the respective peak voltage magnitude corresponding to the monotonically-varying peak magnetic field magnitude of each oscillating localization magnetic field gradient.

In one or more embodiments, the controller is configured to provide AC power simultaneously to only the first and third planar electromagnet coil sets to thereby produce a first oscillating localization magnetic field gradient with respect to the first axis, the controller is configured to provide AC power simultaneously to only the second and third planar electromagnet coil sets to thereby produce a second oscillating localization magnetic field gradient with respect to the second axis, and the controller is configured to provide AC power to only the third planar electromagnet coil set to thereby produce a third oscillating localization magnetic field gradient with respect to the third axis. In one or more embodiments, the first planar spirals are spatially offset from each other along the first chip axis, and the second planar spirals are spatially offset from each other along the second chip axis.

In one or more embodiments, each first interconnected loop and each second interconnected loop includes a respective pair of metal wires disposed in respective metal layers, a respective intra-loop column that electrically connects the respective pair of metal wires of a respective interconnected loop, and a respective inter-loop column that electrically connects one of the metal wires of the respective interconnected loop to one of the metal wires in a subsequent interconnected loop. In one or more embodiments, the at least some of the metal layers and the at least some of the metal vias form a continuous metal structure, with respect to the third chip axis, along a length of the third planar spiral.

In one or more embodiments, the respective readout circuit comprises a respective amplifier and filter circuit electrically coupled having an input coupled to the respective electrically conductive coil; a respective peak-detect-and-hold (PDH) circuit having an input coupled to an output of the respective amplifier and filter circuit; and a respective analog-to-digital converter (ADC) having an input coupled to an output of the respective peak-detect-and-hold circuit. In one or more embodiments, the respective amplifier and filter circuit includes a band-pass filter having an output coupled to an input of a programmable gain amplifier. In one or more embodiments, the respective PDH circuit includes a respective positive differential PDH circuit and a respective negative differential PDH. In one or more embodiments, the respective ADC comprises a respective differential-input successive approximation register (SAR) ADC.

In one or more embodiments, a catheter is attached to the 3D on-chip magnetic sensor. In one or more embodiments, a guidewire is attached to the 3D on-chip magnetic sensor.

Another aspect of the invention is directed to a method of three-dimensional (3D) localization, comprising placing the 3D magnetic sensor within a field of view (FOV) of a 3D magnetic field gradient generator; sequentially producing, with the 3D magnetic field gradient generator, first, second, and third oscillating localization magnetic field gradients with respect to first, second, and third axes, respectively, the first, second, and third axes mutually orthogonal to one another, wherein the FOV corresponds to at least a portion of each oscillating localization magnetic field gradient having a monotonically-varying peak magnitude along a respective axis; sequentially measuring, with a respective electrically conductive coil in the 3D magnetic sensor, respective peak voltages corresponding to the monotonically-varying peak magnitude of each oscillating localization magnetic field gradient; and determining a relative position of the 3D magnetic sensor, with respect to the 3D magnetic field gradient generator, using the respective peak voltages.

In one or more embodiments, the method further comprises attaching and/or mechanically coupling the 3D magnetic sensor to an object, whereby the relative position of the 3D magnetic sensor corresponds to a relative position of the object.

BRIEF DESCRIPTION OF THE DRAWINGS

For a fuller understanding of the nature and advantages of the concepts disclosed herein, reference is made to the detailed description of preferred embodiments and the accompanying drawings.

DETAILED DESCRIPTION

A three-dimensional (3D) magnetic sensor is implemented on a monolithic semiconductor chip with high sensitivity and ultra-low power operation. The sensor includes three orthogonal metal coils that produce a respective voltage signal in response to oscillating magnetic field gradients by electromagnetic induction. The voltage signals are processed by on-chip circuitry to determine peak voltages which correspond to the magnitude of an oscillating magnetic field gradient, produced with AC current, and the relative position of the 3D magnetic sensor.

The 3D magnetic sensor can be fully CMOS compatible, for example in 65 nm CMOS or in another process node, and can achieve high sensitivity with only μW-level power budget. The three orthogonal metal coils produce an induced electromotive force (EMF) in response to the oscillating magnetic flux along each coil's axis. The three orthogonal metal coils can be implemented using the available metal stack in standard CMOS process. By incorporating the 3D coils and all the processing circuitry on a monolithic CMOS chip, the sensor footprint can be significantly reduced and the sensitivity can be enhanced. Furthermore, the μW-level power required by our sensor can be delivered wirelessly or harvested locally from bio-fluids, thus eliminating the need for wired sensors. Such highly miniaturized, ultra-low power and wireless magnetic sensors can be of significant benefit for several applications, particularly for bioelectronics.

The on-chip circuitry can include amplifiers, filters, peak detectors, and/or analog-to-digital (A/D) converters. In an implementation, the magnetic sensor can perform low-noise amplification, filtering, peak detection and 12-bit digitization while consuming only 14.8 μW to yield μT-level sensitivity, which can correspond to a 3D location having about a 500 μm mean accuracy.

Figure 1:
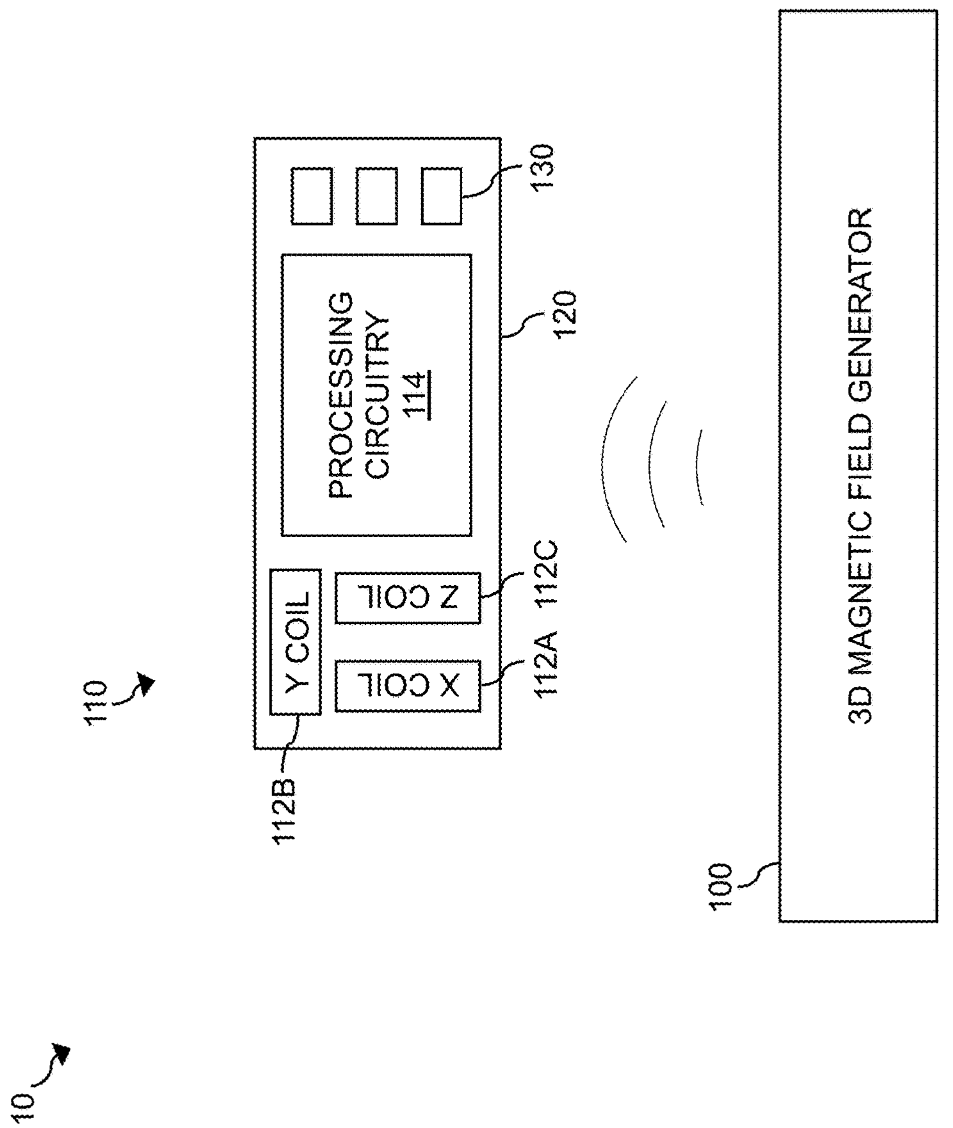
FIG. 1 is a block diagram of a system for three-dimensional (3D) localization using oscillating magnetic field gradients produced with alternating current according to an embodiment.

FIG. 1 is a block diagram of system 10 for 3D localization using oscillating magnetic field gradients produced with AC according to an embodiment. The system 10 includes a 3D magnetic field generator 100 and a 3D magnetic field sensor 110.

The 3D magnetic field generator 100 is configured to generate oscillating magnetic field gradients along or parallel to multiple mutually-orthogonal axes. The 3D magnetic field generator 100 uses AC power to produce the oscillating (e.g., sinusoidal) magnetic field gradients.

The 3D magnetic field generator 100 sequentially generates a first oscillating localization magnetic field gradient along or parallel to a first axis, a second oscillating localization magnetic field gradient along or parallel to a second axis, and a oscillating third localization magnetic field gradient along or parallel to a third axis. The first, second, and third axes are orthogonal to one another. In the Cartesian coordinate system, the first axis can correspond to the "X" axis, the second axis can correspond to the "Y" axis, and the third axis can correspond to the "Z" axis. At least a portion and/or at least a substantial portion of each oscillating magnetic field gradient can have a monotonically-varying peak magnitude along the respective axis so as to uniquely encode a relative position of the 3D magnetic field sensor 110 with respect to the 3D magnetic field generator 100. In some embodiments, each oscillating localization magnetic field gradient magnitude can vary linearly or non-linearly over some or all of the respective oscillating magnetic field gradient.

The 3D magnetic field sensor 110 is monolithically formed on a semiconductor chip 120. The ED magnetic field sensor 110 includes three electrically conductive coils 112A-C (in general, electrically conductive coil(s) 112) and processing circuitry 114. The electrically conductive coils 112 are oriented orthogonally from one another and produce an induced electromotive force (EMF) in response to the oscillating magnetic flux along the respective axis of each electrically conductive coil 112. The induced EMF drives an AC current through the processing circuitry 114 where the peak magnitude of the AC current is detected for each conductive coil 112. The peak magnitude of the AC current for each conductive coil 112 corresponds to the peak magnitude of the induced EMF in the respective conductive coil 112, which corresponds to the peak magnitude of the oscillating magnetic field gradient at the position at the position of the 3D magnetic field sensor 110. The peak magnitude of each oscillating magnetic field gradient can be used to determine the relative 3D position of the 3D magnetic field sensor 110 with respect to the 3D magnetic field generator 100. The peak magnitude of the induced EMF in the respective conductive coil 112 for each oscillating magnetic field gradient can be used to determine the angular orientation of the 3D magnetic field sensor 110 with respect to the 3D magnetic field generator 100.

The 3D magnetic field sensor 110 can further include contact pads and/or other circuitry 130. The circuitry 130 can include wireless communication circuitry that can allow the 3D magnetic field sensor 110 to communicate with an external device. The wireless communication circuitry can support one or more local wireless communication protocols or standards, such as Bluetooth, near-field communication (NFC), and/or backscattering. In addition or in the alternative, the wireless communication circuitry can support WiFi and/or cellular communications protocols or standards. The wireless communication circuitry can transmit the peak magnetic field measurements from the 3D magnetic field sensor 110 (e.g., from each conducive coil 112).

Figure 2:
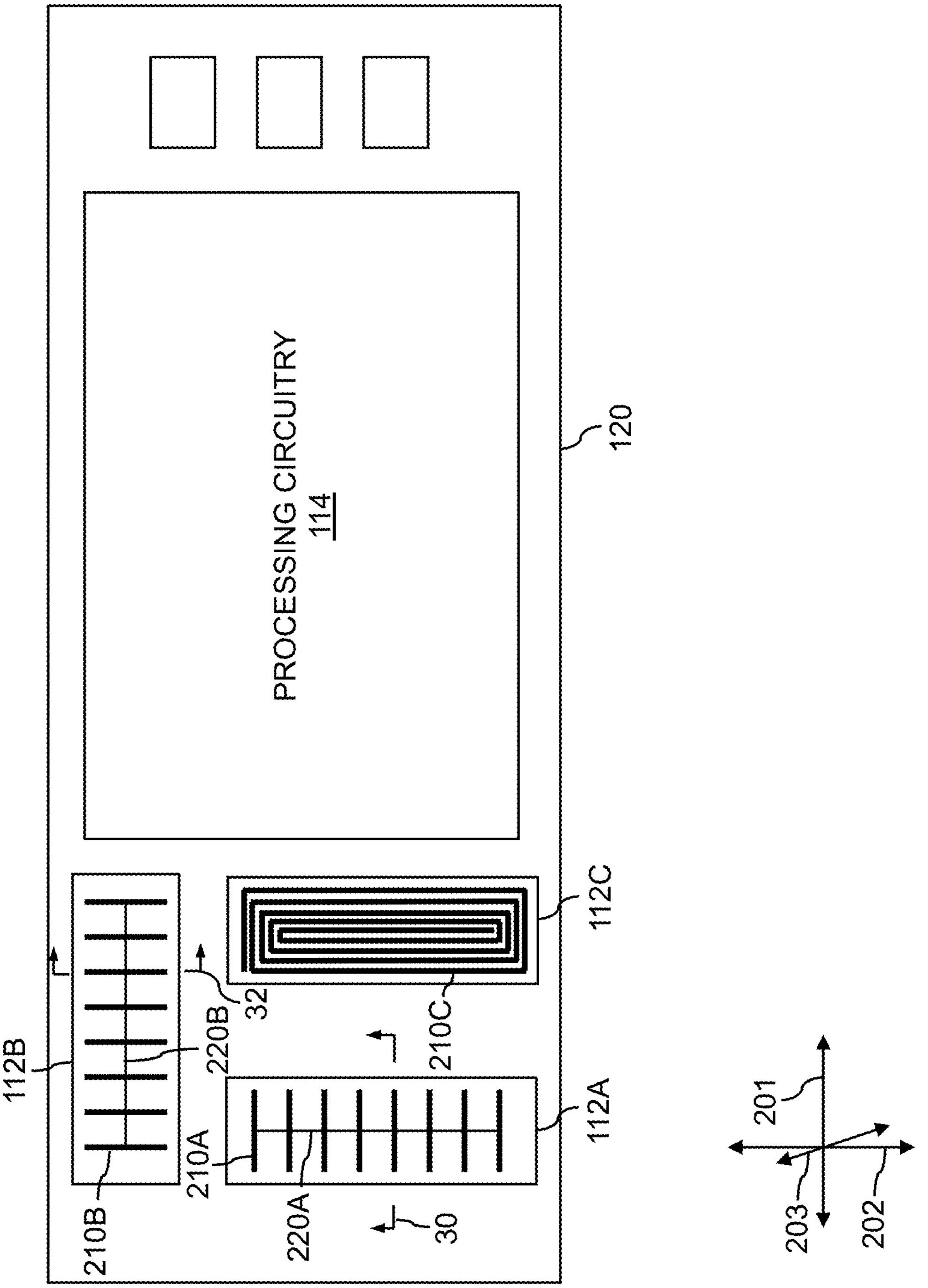
FIG. 2 is top view of the 3D magnetic field sensor illustrated in FIG. 1 according to an embodiment.

FIG. 2 is top view of the 3D magnetic field sensor 110 according to an embodiment. The first electrically conductive coil 112A includes a plurality of spirals 210A that are electrically connected to each other in series through wires 220A. The spirals 210A are parallel to a plane defined by the first and third axes 201, 203 and are wound about a second axis 202. The first, second, and third axes 201-203 are mutually orthogonal. The first, second, and third axes 201-203 can alternately be referred to as the first, second, and third chip axes 201-203, respectively. The magnitude of the induced EMF in the first coil 112A corresponds to the component of the oscillating magnetic field flux across the first axis 201.

The second electrically conductive coil 112B includes a plurality of spirals 210B that are electrically connected to each other in series through wires 220B. The spirals 210B are parallel to a plane defined by the second and third axes 202, 203 and are wound about the first axis 201. The magnitude of the induced EMF in the second coil 112B corresponds to the component of the oscillating magnetic field flux across the second axis 202. In some embodiments, the first and second electrically conductive coil 112A, 112B can be the same but the second electrically conductive coil 112B is rotated by 90 degrees relative to the first electrically conductive coil 112A.

The third electrically conductive coil 112C includes a spiral 210C that is parallel to a plane defined by the first and second axes 202, 203 and is wound about the third axis 201. The magnitude of the induced EMF in the third coil 112C corresponds to the component of the oscillating magnetic field flux across the third axis 203.

The induced EMF in each electrically conductive coil 112A-C is a product of the effective cross sectional area of the electrically conductive coil 112A-C and the rate of change of the oscillating magnetic field which is given by:

$$dB/dt = B_0 * \omega * \cos(\omega t) \quad (1)$$

where $B_0$*sin(ωt) is the oscillating magnetic field at the sensor's location. Eq. (1) illustrates that the frequency a of the oscillating magnetic field can be varied to enhance the signal at the sensor 110. This is an advantage compared to using DC magnetic field gradients where the signal at the sensor 110 can be enhanced only by increasing $B_0$, which requires a higher current in the gradient coils or more number of turns. In contrast, AC magnetic field gradients offer a more power-efficient way by increasing the frequency of operation while keeping the current (and hence $B_0$) constant. Higher power efficiency is also achieved for the sensor 110 as the 3D coil-based sensing requires only μW-level power consumption by the processing circuitry 114, which is orders of magnitude smaller than the mW-level power consumed by the Hall sensors for sensing DC gradients.

For selecting the excitation frequency ω, Eq. (1) indicates that a higher value of ω leads to a higher EMF signal. However, the reactive impedance (jLω) of the gradient coils used in the 3D magnetic field generator 100 also increases with a, requiring a higher voltage AC power supply unit for the same current. The gradient coils can be powered at a frequency in the range of about 100 Hz to about 100 kHz, including about 500 Hz, about 1 kHz, about 10 kHz, about 50 kHz, and any value or range between any two of the foregoing values. In other embodiments, the frequency can be higher than about 100 kHz such as about 250 kHz or higher. The value of w should be high enough to avoid electromagnetic interference from the surroundings, most common being the 50/60 Hz components caused by the power grid.

The induced EMF of each electrically conductive coil 112A-C, which is an indirect measure of the oscillating magnetic field produced by the external gradient coils, is given by:

$$EMF = d\phi/dt = N.A. * dB/dt \quad (2)$$

where N.A. is a sensor-dependent geometric factor and dB/dt is an AC gradient dependent factor. For a sinusoidal magnetic field produced by the 3D magnetic field generator 100 gradient coils:

$$B = B_0 * \sin(\omega t) \quad (3)$$

$$dB/dt = B_0 * \omega * \cos(\omega t) \quad (4)$$

In the 3D magnetic field generator 100, both $B_0$ and w can be used to enhance the EMF given by Eq. (2). In the 3D magnetic field sensor 110, the geometrical factor of N.A. can be increased to control the amount of induced voltage. It is to be noted that A is the effective cross-section area of the coil-sensor that is perpendicular to the incoming oscillating magnetic field flux, and N is the total number of turns of the coil-sensor in the direction of the incoming flux.

For two coils that have a mutual inductance M between them, the induced EMF in one (secondary) due to changing current I in the other (primary) is given by:

$$EMF = M * dI/dt \quad (5)$$

M depends on various factors including (i) the area and number of turns in both the primary and the secondary coils; (ii) the distance between the two coils; (iii) the relative orientation of the two coils; and (iv) the media between the two coils. Hence, the best way to evaluate M is through electromagnetic simulations and then verifying the simulated outcome by comparison with theoretical calculations. For the purpose of calculation of M, we make use of another equation:

$$EMF = N * A * dB/dt \quad (6)$$

which describes the induced EMF in the secondary coil (e.g., electrically conductive coil 112A, 112B, and/or 112C) as a function of the secondary coil's number of turns (N), cross-section area (A) perpendicular to the magnetic flux B, and the rate of change of the magnetic flux. By equating (5) and (6), we obtain:

$$M = N * A * (dB/dt)/(dI/dt) \quad (7)$$

where I is the current in the primary coil (e.g., one of the coils in the 3D magnetic field generator 100) and B is the oscillating magnetic field at the location of the secondary coil. For a sinusoidal current I given by:

$$I = I_0 * \sin(\omega * t) \quad (8)$$

The oscillating magnetic field B at the location of the secondary coil is given by:

$$B = B_0 * \sin(\omega * t) \quad (9)$$

Plugging I and B from Eq. (8) and (9) respectively in Eq. (9), we get:

$$M = N * A * B_0 / I_0 \quad (10)$$

where $I_0$ is the peak current used to excite the primary coil and $B_0$ is the peak magnetic field observed at the secondary coil's location. For simple coil structures, $B_0$ can be calculated theoretically from $I_0$ using the Biot-Savart law since both are peak (hence can be considered DC for calculation purpose) values. For more complex geometries such as the gradient coils used in this work, the value of $B_0$ for a given $I_0$ can be found experimentally and/or through magnetostatic simulations in Maxwell. Once the ratio $B_0/I_0$ is found, we can plug it into Eq. (12) and use the geometrical parameters N and A of the secondary coil to calculate the mutual inductance M. This theoretical value of M can be compared with its simulated value from magnetostatic simulations in Maxwell and provide a higher degree of confidence in the effective coupling that will occur between the two coils in the final real-world scenario. For a comprehensive study, the value of M can be evaluated under different environments such as silicon chip environment, frequency variation, eddy currents, and presence of human tissue.

There are several advantages to using an AC (e.g., oscillating) magnetic field gradient instead of DC for localization of magnetic-field sensing microdevices. First, for a gradient $G_0$ that corresponds to a DC current of $I_0$, the same gradient in AC domain would require a current excitation of $I_0 \sin(\omega_0 t)$. The power loss due to heating in the coils, which can be quite significant for continuous operation, would be $$I_0^2 R$$

for DC excitation but $$I_0^2 R/2$$

for AC excitation. Thus, the power loss is reduced by half for AC gradients.

Second, for an AC gradient based localization system, the 3D magnetic-field sensor is not constrained to employ a Hall-effect based magnetic sensor for high resolution. Instead, a passive coil-based sensor capable of sensing the induced EMF due to the AC magnetic field produced by the gradient coils can be used. As shown by Eq. (13), the position resolution Δx obtained by using a DC gradient G and a magnetic sensor with resolution ΔB, can be improved by increasing the value of G which scales linearly with the DC current (for a given sensor and coil geometry):

$$\Delta x = \Delta B/G \tag{11}$$

Thus, a lower Δx implies a higher G which requires a higher I. On the other hand, while using the AC gradient, the induced EMF is given by:

$$EMF = d\phi/dt = N.A * \mathrm{dB}/dt \tag{12}$$

where N.A. is the sensor dependent geometric factor and dB/dt is the AC gradient dependent factor. For a sinusoidal magnetic field produced by the gradient coils:

$$B = B_0 * \sin(\omega t) \tag{13}$$

$$\mathrm{dB}/dt = B_0 * \omega * \cos(\omega t) \tag{14}$$

As seen from Eq. (16), dB/dt not only depends on $B_0$ which is the peak magnetic field value that depends on the peak current in the coils, but also on the frequency component ω. Thus, we now have an additional tuning knob of frequency ω to enhance the sensitivity of the sensor, thus reducing ΔB in Eq. (11). This improves Δx without having to ramp up the current to yield a higher G. If the current I in the gradient coils stays the same while the frequency is changed, the $I^2R$ heat loss also stays the same, unlike the DC gradients that increase the current linearly and result in a quadratic increase in the $I^2R$ loss. This results in a more power efficient system.

Third, the sensor for the AC gradient based localization can be replaced by a passive EMF-sensing inductor coil that does not consume any active power during the EMF sensing mechanism. The processing of the EMF can easily be done within a few μW of power, as described herein. The complete end-to-end power of the coil-based sensor and processing circuits described herein can be <15 μW, which is significantly less than the milliwatt-level power consumed by power-hungry Hall sensors used in DC magnetic gradient sensors. It is also to be noted that the sensitivity of Hall sensors directly depends on the current used in Hall elements, implying that a higher sensitivity comes at the cost of higher power. However, for the passive coil-based sensor, the sensitivity can be enhanced by either using a higher frequency on the gradient coils side or by using a higher geometrical factor on the sensor side. As discussed before, a higher frequency does not lead to more power loss for the gradient coils. Thus, the AC gradient based localization system is more power efficient both from the gradient coils side and the sensor side.

The AC gradient based system is also more robust to DC offsets, ambient earth's magnetic field, and avoids low-frequency noise problems.

Figure 3:
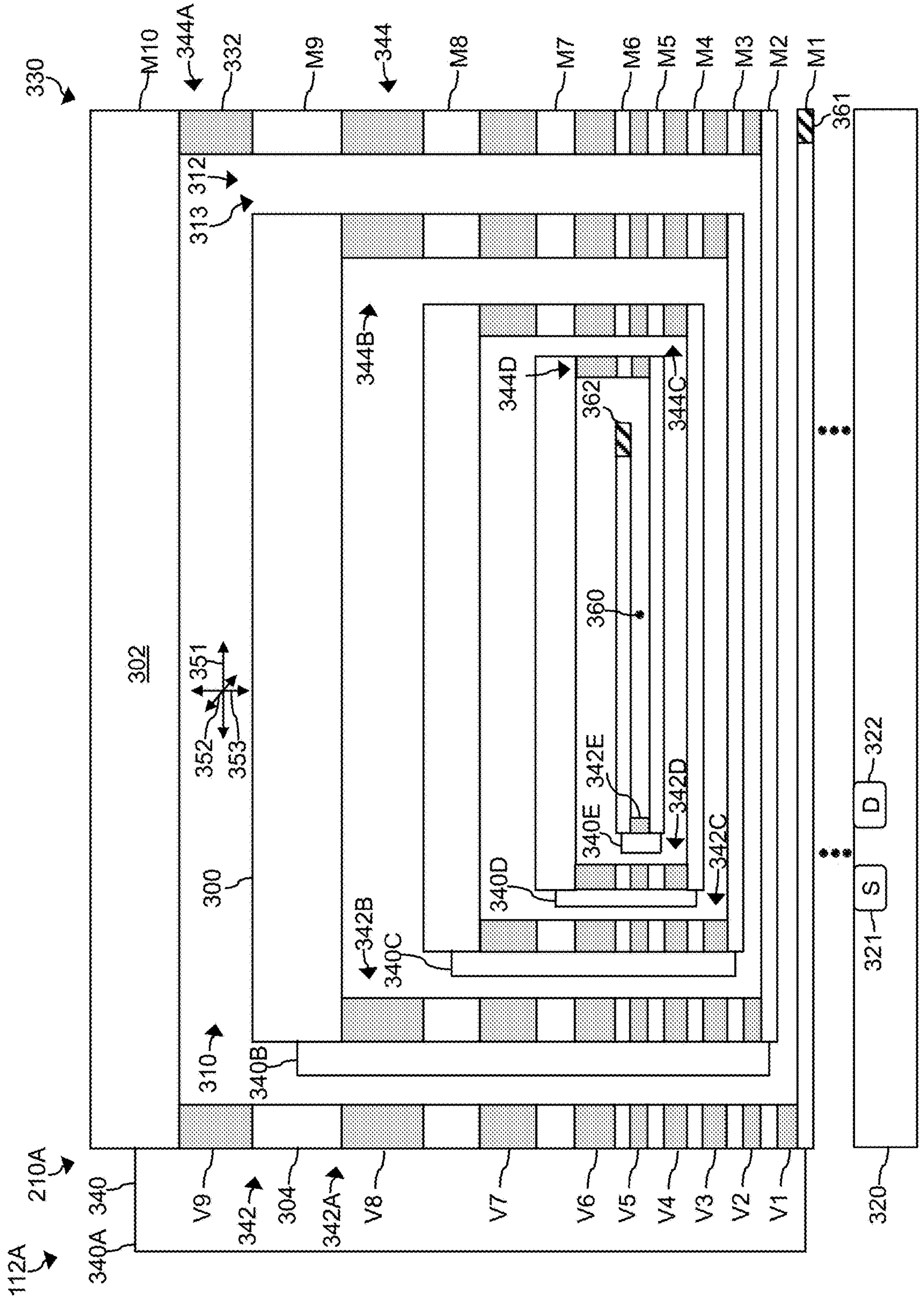
FIG. 3 is a cross section of a spiral in the first electrically conductive coil illustrated in FIG. 2 according to an embodiment.

FIG. 3 is a cross section of a spiral 210A in the first electrically conductive coil 112A through plane 30 in FIG. 2 according to an embodiment. The spiral 210A includes a plurality of metal layers 300 and a plurality of insulation layers 310 that are disposed on a semiconductor substrate 320. The semiconductor substrate 320 can include or can be silicon, silicon dioxide, aluminum oxide, sapphire, germanium, gallium arsenide, silicon germanium, indium phosphide, or another semiconductor material. Active elements for transistors such as a source 321 and a drain 322 can be defined on or in the semiconductor substrate 320. The active elements can be located in the portion of the semiconductor substrate 320 beneath the spiral 210A and/or in another portion of the semiconductor substrate 320. For example, the active elements can be located in the portion of the semiconductor substrate 320 that corresponds to the processing circuitry 114 (FIGS. 1, 2).

The metal layers 300 include metal levels M1-M10 in the illustrated example. Additional or fewer metal layers 300 can be included in other embodiments. It is noted that the numerical notations used herein are relative and are not necessarily the same as the metal level numbers in the semiconductor chip 120. In some embodiments, there may be one or more metal levels between the first metal level M1 and the semiconductor substrate 320, for example to form electrical connections to the active elements in the portion of the semiconductor substrate 320 beneath the spiral 210A (e.g., below metal level M1). In other embodiments, the first metal level M1 can be the first metal level in the semiconductor chip 120. Using more metal layers increases the effective cross-sectional area of the spiral 210A which increases the induced EMF of the first electrically conductive coil 112A.

The insulation layers 310 are located between neighboring metal layers 300 (e.g., between metal levels M1 and M2). Each insulation layer mechanically supports any layers above the insulation layer and electrically isolates the neighboring metal layers 300. Insulation material 312 is also located in any gaps 313 in the metal layers 300 to electrically isolate any metal wires 302 and/or metal wire segments 304 defined in the metal layers 300. The insulation layers 310 and the insulation material 312 can comprise or consist of a dielectric material such as silicon dioxide.

The spiral 210A includes a plurality of interconnected metal loops 330. Each loop 330 includes a pair 340 of metal wires 302, an intra-loop metal column 342, and an inter-loop metal column 344. The intra-loop metal column 342 includes one or more metal vias 332 and one or more metal segments 304 of any metal layers 300 between the pair 340 of metal wires 302. The metal via(s) 332 and the optional metal segment(s) 304 are electrically connected to one another and to the pair 340 of metal wires 330 such that the pair 340 of metal wires 330 is electrically connected through the intra-loop metal column 342. The inter-loop metal column 344 includes one or more metal vias 332 and one or more metal segments 304 of any metal layers 300 between a first metal wire 302 of one pair 340 and a second metal wire 302 of another pair 340. The metal vias 332 are defined in the insulation layers 310.

A first pair 340A of metal wires 302 includes the metal wires 302 formed in the M1 and M10 layers. A second pair 340B of metal wires 302 includes the metal wires 302 formed in the M2 and M9 layers. A third pair 340C of metal wires 302 includes the metal wires 302 formed in the M3 and M8 layers. A fourth pair 340D of metal wires 302 includes the metal wires 302 formed in the M4 and M7 layers. A fifth pair 340E of metal wires 302 includes the metal wires 302 formed in the M5 and M6 layers. The first pair 340A is the outermost pair, the second pair 340B is the next outermost pair, and so on. The fifth pair 340E is the innermost pair (the least outermost pair).

The second pair 340B is located between the first pair 340A. The third pair 340C is located between the second pair 340B and between the first pair 340A. The fourth pair 340D is located between the third pair 340C, between the second pair 340B, and between the first pair 340A. The fifth pair 340E is located between the fourth pair 340D, between the third pair 340C, between the second pair 340B, and between the first pair 340A. The first pair 340A is the outermost pair and the firth pair 340E is the innermost pair.

A first intra-loop metal column 342A electrically connects the first pair 340A of metal wires 302 in the first loop 330. The first intra-loop metal column 342A includes metal vias 332 in via levels V1-V9 and metal segments 304 in metal levels M2-M9. A first inter-loop metal column 344A electrically connects the metal wire 302 in metal level M10 in the first pair 340A to the metal wire 302 in metal level M2 in the second pair 340B to electrically couple the first and second loops 330.

A second intra-loop metal column 342B electrically connects the second pair 340B of metal wires 302 in the second loop 330. The second intra-loop metal column 342B includes metal vias 332 in via levels V2-V8 and metal segments 304 in metal levels M3-M8. A second inter-loop metal column 344B electrically connects the metal wire 302 in metal level M9 in the second pair 340B to the metal wire 302 in metal level M3 in the third pair 340C to electrically couple the second and third loops 330.

A third intra-loop metal column 342C electrically connects the third pair 340C of metal wires 302 in the third loop 330. The third intra-loop metal column 342C includes metal vias 332 in via levels V3-V7 and metal segments 304 in metal levels M4-M7. A third inter-loop metal column 344C electrically connects the metal wire 302 in metal level M8 in the third pair 340C to the metal wire 302 in metal level M4 in the fourth pair 340D to electrically couple the third and fourth loops 330.

A fourth intra-loop metal column 342D electrically connects the fourth pair 340D of metal wires 302 in the fourth loop 330. The fourth intra-loop metal column 342D includes metal vias 332 in via levels V4-V6 and metal segments 304 in metal levels M5 and M6. A fourth inter-loop metal column 344D electrically connects the metal wire 302 in metal level M7 in the fourth pair 340D to the metal wire 302 in metal level M5 in the fifth pair 340D to electrically couple the fourth and fifth loops 330.

A fifth intra-loop metal column 342E electrically connects the fifth pair 340E of metal wires 302 in the fifth loop 330. The fifth intra-loop metal column 342E includes a metal via 332 in via levels V5.

The metal wires 302 have a respective length, a respective width, and a respective height. The respective length of each metal wire 302 can be measured with respect to a first axis 351, which can be parallel to the first axis 201 (FIG. 2). The respective width of each metal wire 302 can be measured with respect to a second axis 352 that is orthogonal to the first axis 351 and that can be parallel to the second axis 202 (FIG. 2). The respective height of each metal wire 302 can be measured with respect to a third axis 353 that is orthogonal to the first and second axes 351, 352 and that can be parallel to the third axis 203 (FIG. 2). The respective length of each metal wire 320 is greater than (e.g., significantly greater than) the respective height to increase the cross-sectional magnetic. A ratio of the respective length to the respective height of each metal wire 302 can be in the range of 500:1 to about 10,000:1 including any values or ranges therebetween. The width and the height of each metal wire can be the same or approximately the same. Thus, a ratio of the respective length to the respective width of a given metal wire 302 can be the same or approximately the same as the ratio of the respective length to the respective height of each metal wire 302 for that metal wire.

Figure 4:
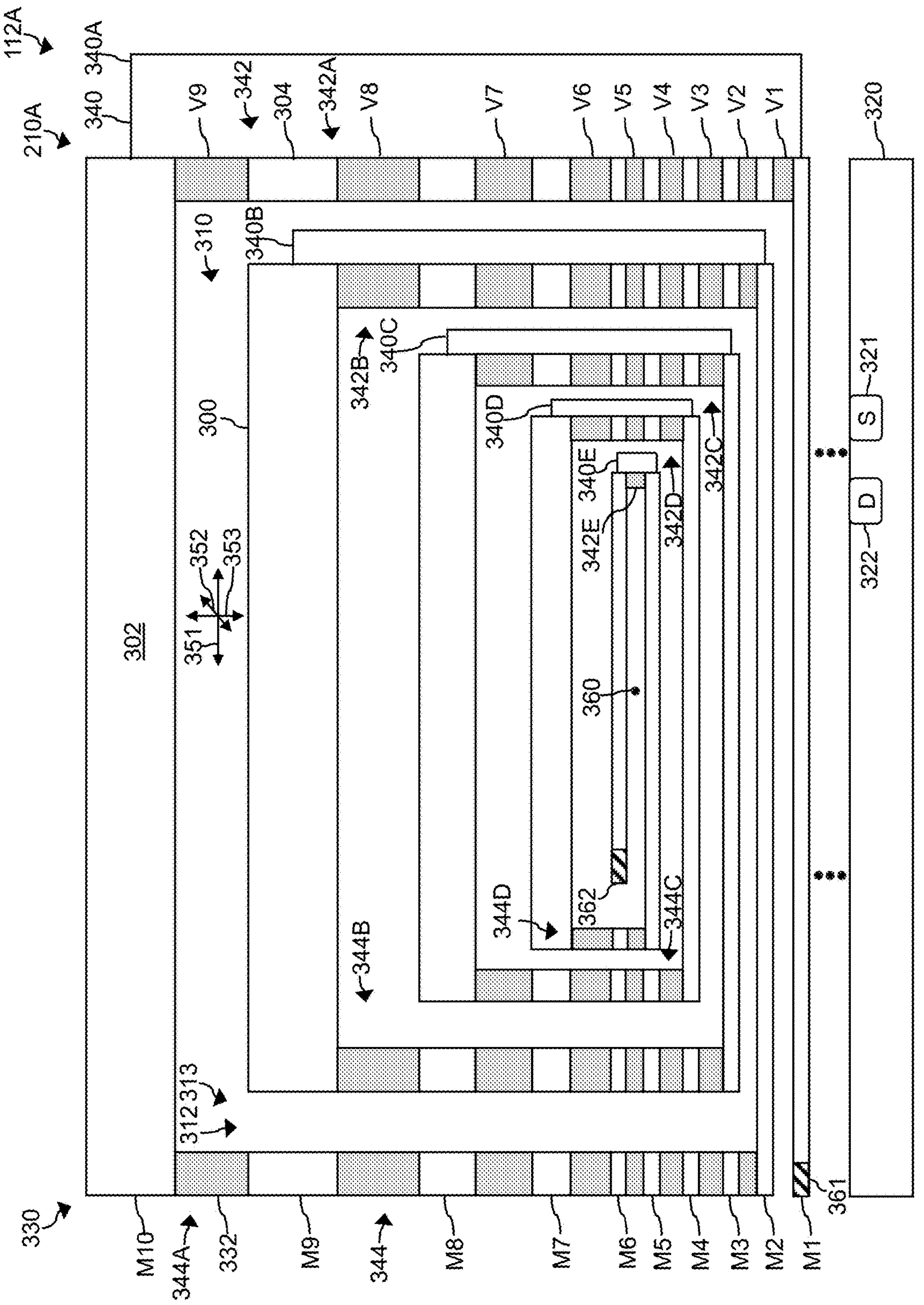
FIG. 4 is a cross section of a spiral in the first electrically conductive coil illustrated in FIG. 2 according to another embodiment.

The spiral 210A and the coils 330 are wound about an axis 360, which is parallel to the second axis 352. Due to the general increase in thickness (e.g., height) of the metal layers 300 and insulating layers 310 with distance from the semiconductor substrate 320 (e.g., metal level M10 is thicker than metal level M1), the axis 360 is positionally offset so as to be located closer to the metal level M1 than to the metal level M10. The spiral 210A is generally planar and lies within or parallel to the plane defined by the first and third axes 351, 353. In FIG. 3, the spiral 210A is wound in the counterclockwise direction with respect to the axis 360. In another embodiment, the spiral 210A is wound in a clockwise direction with respect to the axis 360, as illustrated in FIG. 4.

There are two terminals at the opposing ends of the first spiral 210A. A first terminal 361 is located on (e.g., electrically connected to) the metal wire 302 formed in the M1 metal layer. The first terminal 361 and the first intra-loop metal column 342A can be located on (e.g., electrically connected to) opposing ends of the metal wire 302 formed in the M1 metal layer. A second terminal 362 is located on (e.g., electrically connected to) the metal wire 302 formed in the M6 metal layer. The second terminal 362 and the fifth intra-loop metal column 342E can be located at (e.g., electrically connected to) opposing ends of the metal wire 302 formed in the M6 metal layer.

Neighboring spirals 210A in the first electrically conductive coil 112A are electrically coupled through the first and second terminals 361, 362 and the wires 220A (e.g., in a cascaded connection), which can increase the effective coupling area of the first electrically conductive coil 112A. The first terminal 361 of one spiral 210A is electrically connected to the second terminal 362 of a neighboring spiral 210A through one or more wires 220A. Similarly, the second terminal 362 of one spiral 210A is electrically connected to the first terminal 361 of a neighboring spiral 210 through one or more wires 220A. The terminals 361, 362 at opposing ends of the first electrically conductive coil 112A can be electrically coupled to the processing circuitry 114.

Figure 5:
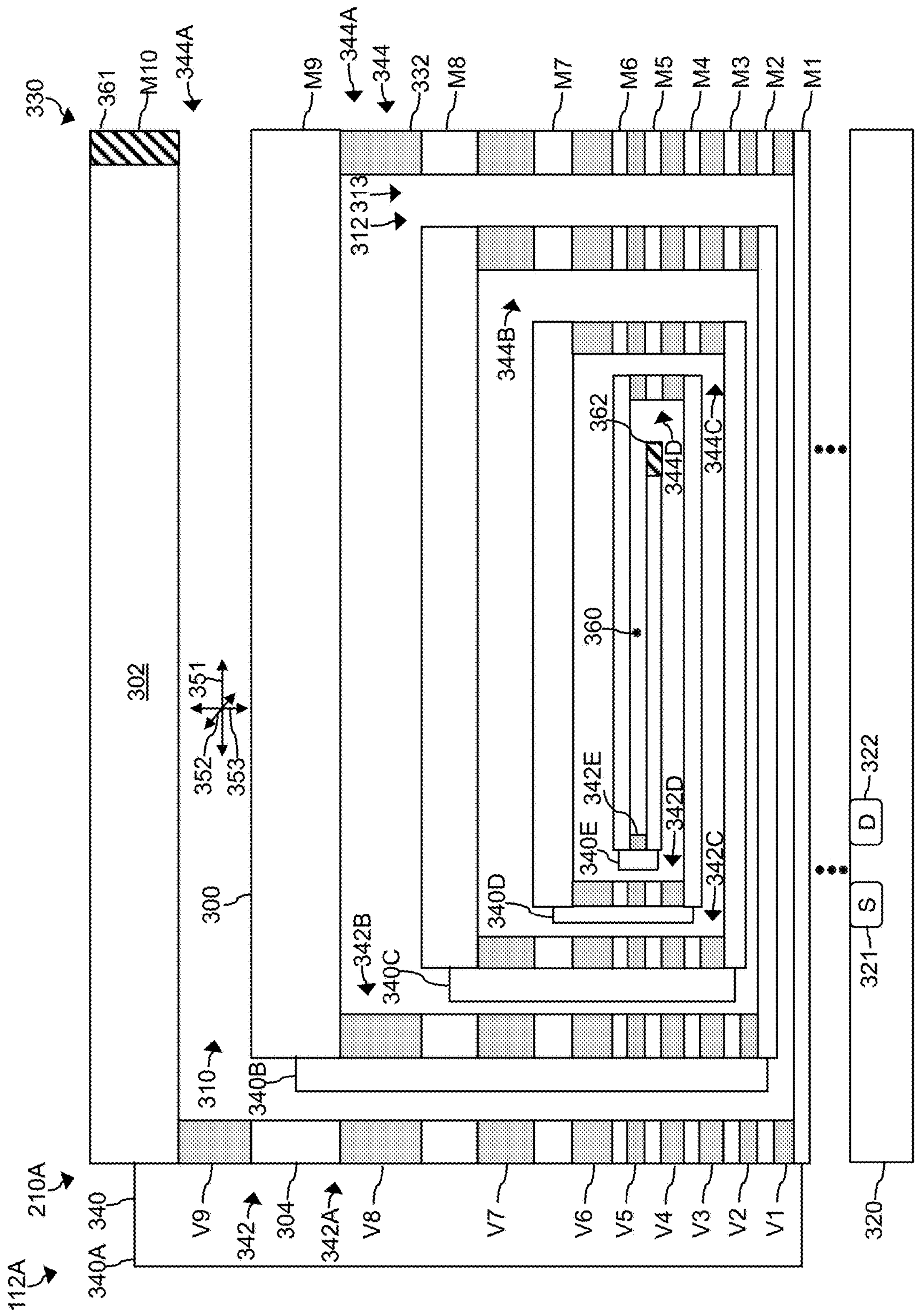
FIG. 5 is a cross section of a spiral in the first electrically conductive coil illustrated in FIG. 2 according to another embodiment.
Figure 6:
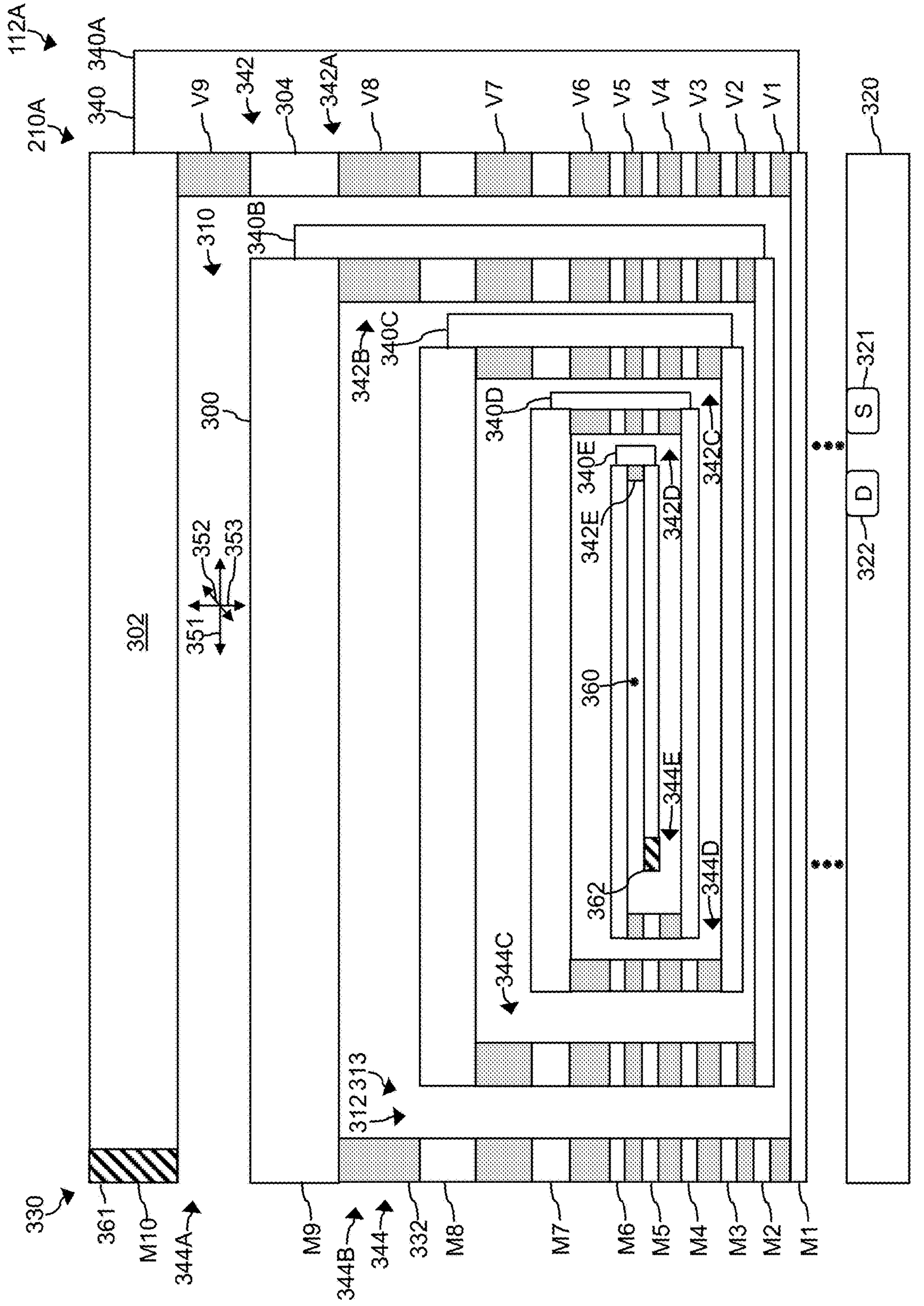
FIG. 6 is a cross section of a spiral in the first electrically conductive coil illustrated in FIG. 2 according to another embodiment.

In another embodiment, the first terminal 361 is located on (e.g., electrically connected to) the metal wire 302 formed in the M10 metal layer, for example as illustrated in FIGS. 5 and 6. In FIG. 5, the spiral 210A is wound in a counterclockwise direction with respect to the axis 360. In FIG. 6, the spiral 210A is wound in a clockwise direction with respect to the axis 360.

The overall length of the coil 112A, as measured with respect to the second axis 202, is significantly larger than the height of the spiral 210A (e.g., of the coil-metal stack), as measured with respect to the third axis 203, 353 to increase the effective cross-sectional area of the coil 112A and to increase the induced EMF. For example, a ratio of the overall length of the coil 112A with respect to the height of the spiral 210A can be about 50:1 to about 250:1 including about 100:1, about 150:1, about 200:1, and any values or ranges between any two of the foregoing ratios. In some embodiments, the length of the coil 112A can be equal to or approximately equal to one of the dimensions (e.g., a width or length) of the semiconductor chip 120.

As discussed above, the second electrically conductive coil 112B can be the same as the first electrically conductive coil 112A but the second electrically conductive coil 112B is rotated by 90 degrees relative to the first electrically conductive coil 112A. Thus, the spirals 210B in the second electrically conductive coil 112B can be the same as the spirals 210A in the first electrically conductive coil 112A but the spirals 210B are rotated by 90 degrees relative to the spirals 210A.

Figure 7:
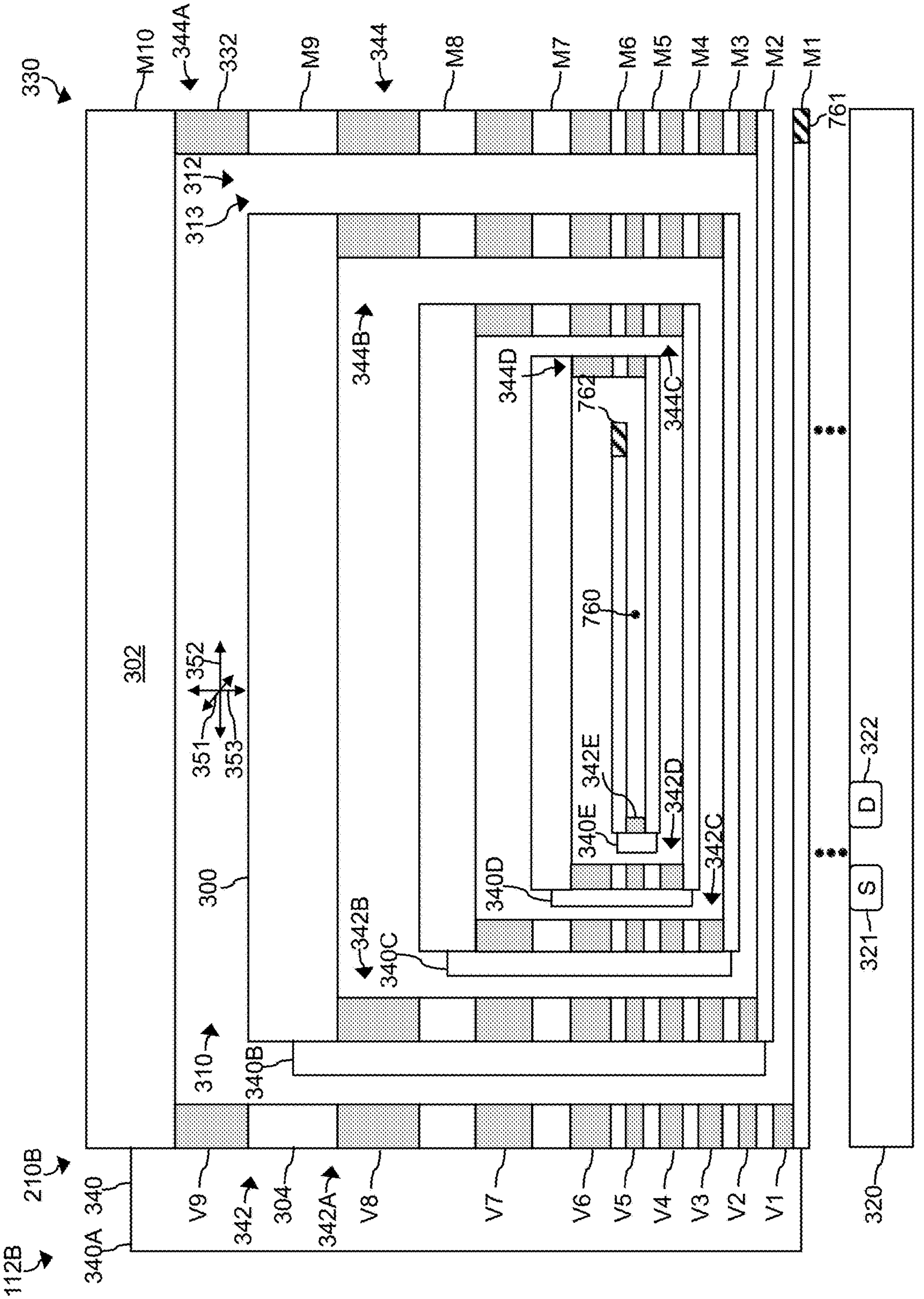
FIG. 7 is a cross section of a spiral in the second electrically conductive coil illustrated in FIG. 2 according to an embodiment.

FIG. 7 is a cross section of a spiral 210B in the second electrically conductive coil 112B through plane 32 in FIG. 2 according to an embodiment. In this embodiment, spiral 210B is the same as spiral 210A in the embodiment illustrated in FIG. 3 except that the spiral 210B is rotated by 90 degrees relative to the spiral 210A.

As such, the respective length of each metal wire 302 in spiral 210B can be measured with respect to the second axis 352. The respective width of each metal wire 302 in spiral 210B can be measured with respect to the first axis 351. The respective height of each metal wire 302 in spiral 210B can be measured with respect to the third axis 353. The respective length of each metal wire 320 is greater than (e.g., significantly greater than) the respective height. A ratio of the respective length to the respective height of each metal wire 302 can be in the range of about 50 to about 250 including about 100, about 150, about 200, and any values or ranges between any two of the foregoing values. The width and the height of each metal wire can be the same or approximately the same. Thus, a ratio of the respective length to the respective width of a given metal wire 302 can be the same or approximately the same as the ratio of the respective length to the respective height of each metal wire 302 for that metal wire.

The spiral 210B and the coils 330 are wound about an axis 760, which is parallel to the first axis 351 and orthogonal to axis 360. Due to the general increase in thickness (e.g., height) of the metal layers 300 and insulating layers 310 with distance from the semiconductor substrate 320 (e.g., metal level M10 is thicker than metal level M1), the axis 360 is positionally offset so as to be located closer to the metal level M1 than to the metal level M10. The spiral 210B is generally planar and lies within or parallel to the plane defined by the second and third axes 352, 353.

Figure 8:
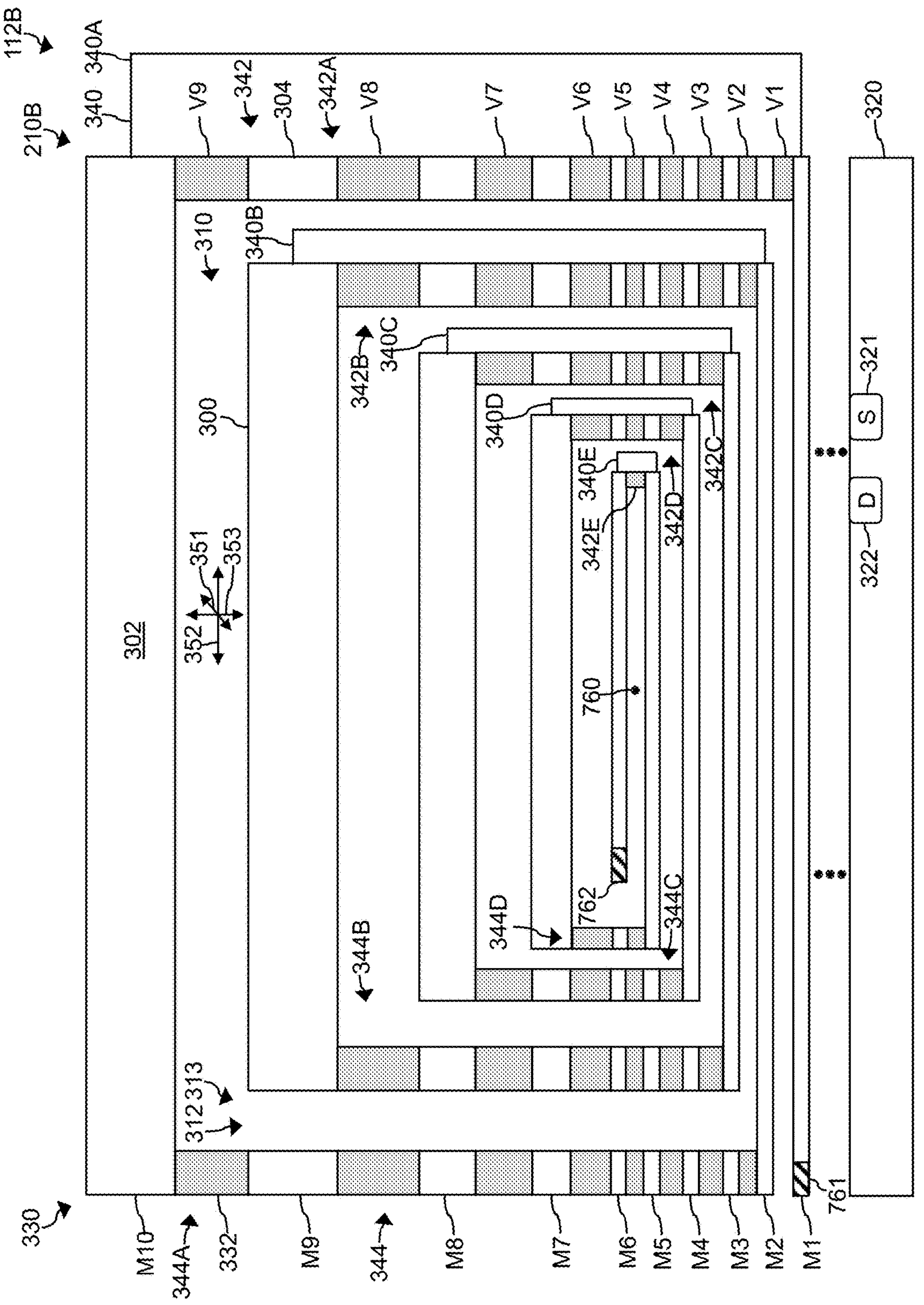
FIG. 8 is a cross section of a spiral in the second electrically conductive coil illustrated in FIG. 2 according to another embodiment.

In FIG. 7, the spiral 210B is wound in the counterclockwise direction with respect to the axis 760. In another embodiment, the spiral 210B is wound in a clockwise direction with respect to the axis 760, as illustrated in FIG. 8.

There are two terminals at the opposing ends of the second spiral 210B. A first terminal 761 is located on (e.g., electrically connected to) the metal wire 302 formed in the M1 metal layer. The first terminal 761 and the first intra-loop metal column 342A can be located on (e.g., electrically connected to) opposing ends of the metal wire 302 formed in the M1 metal layer. A second terminal 762 is located on (e.g., electrically connected to) the metal wire 302 formed in the M6 metal layer. The second terminal 762 and the fifth intra-loop metal column 742E can be located at (e.g., electrically connected to) opposing ends of the metal wire 302 formed in the M6 metal layer.

Neighboring spirals 210B in the second electrically conductive coil 112B are electrically coupled through the first and second terminals 761, 762 and the wires 220B. The first terminal 761 of one spiral 210B is electrically connected to the second terminal 762 of a neighboring spiral 210B through one or more wires 220B. Similarly, the second terminal 762 of one spiral 210B is electrically connected to the first terminal 761 of a neighboring spiral 210B through one or more wires 220B. The terminals 761, 762 at opposing ends of the second electrically conductive coil 112B can be electrically coupled to the processing circuitry 114.

Figure 9:
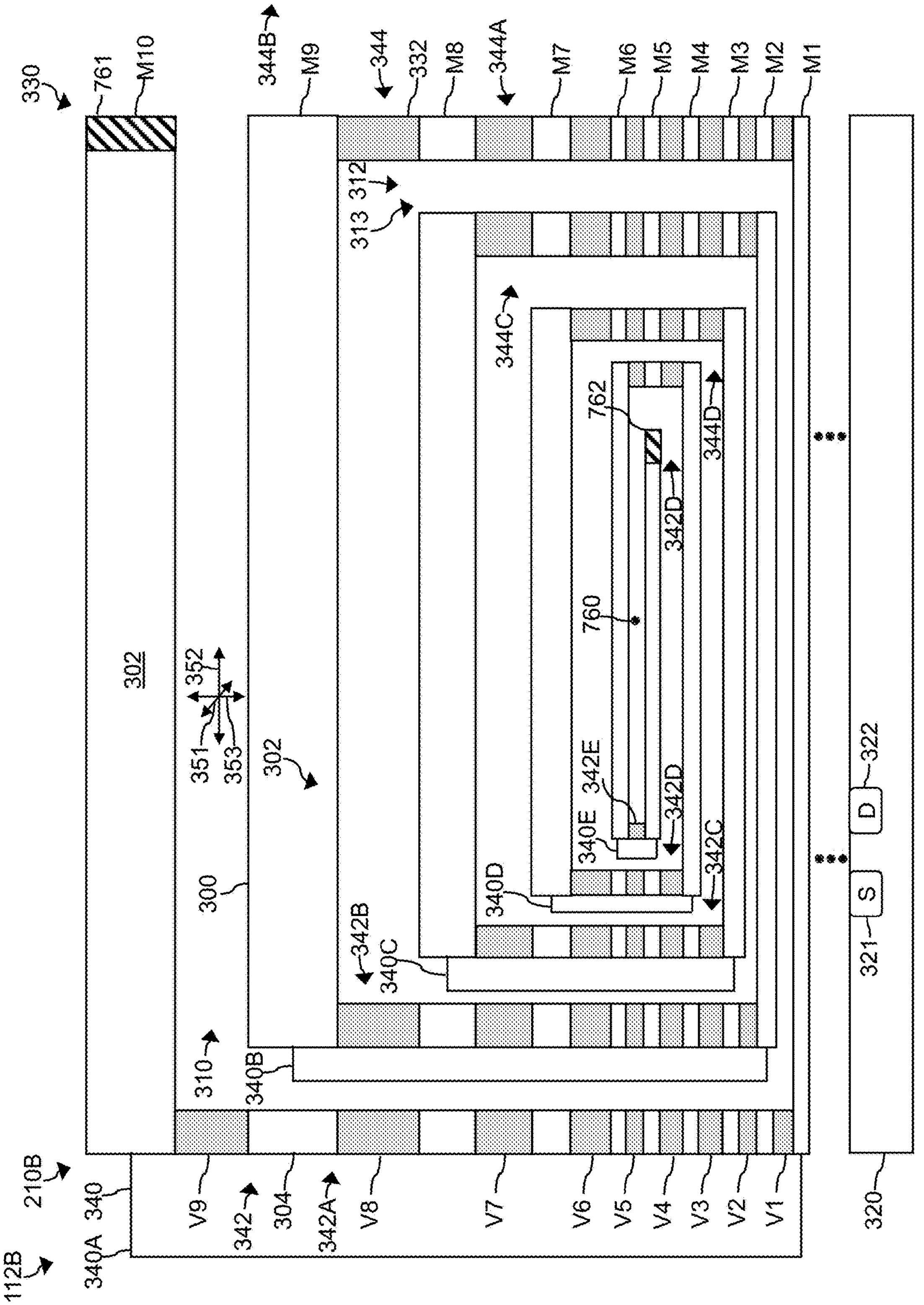
FIG. 9 is a cross section of a spiral in the second electrically conductive coil illustrated in FIG. 2 according to another embodiment.
Figure 10:
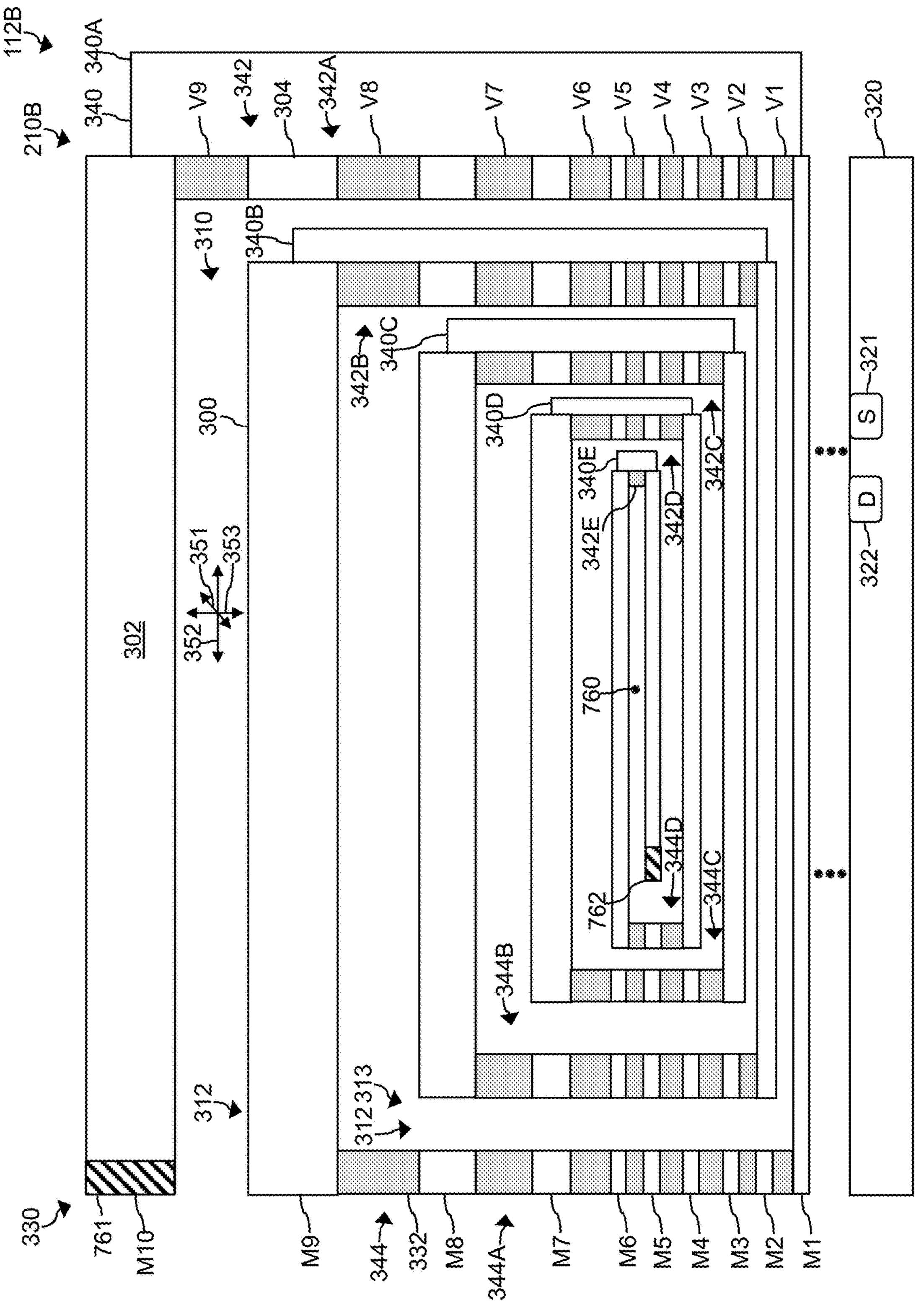
FIG. 10 is a cross section of a spiral in the second electrically conductive coil illustrated in FIG. 2 according to another embodiment.

In another embodiment, the first terminal 761 is located on (e.g., electrically connected to) the metal wire 302 formed in the M10 metal level, for example as illustrated in FIGS. 9 and 10. In FIG. 9, the spiral 210B is wound in a counterclockwise direction with respect to the axis 760. In FIG. 10, the spiral 210B is wound in a clockwise direction with respect to the axis 760.

Figure 11:
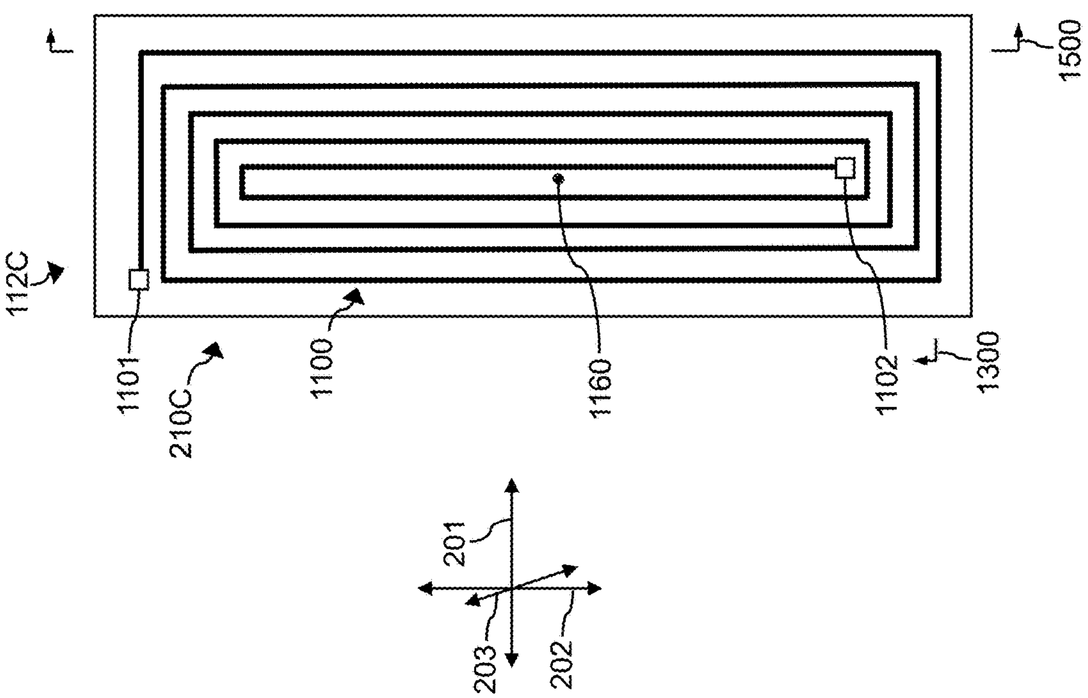
FIG. 11 is an isolated top view of the third electrically conductive coil illustrated in FIG. 2 according to an embodiment.

FIG. 11 is an isolated top view of the third electrically conductive coil 112C illustrated in FIG. 2. The spiral 210C is formed by metal wires in one or more metal levels of the semiconductor chip 120. The third electrically conductive coil 112C includes two terminals 1101, 1102 at the opposing ends of the spiral 210C. The terminals 1101, 1102 can be electrically coupled to the processing circuitry 114. The spiral 210C is generally planar and lies within or parallel to the plane defined by the first and second axes 351, 352.

Figure 12:
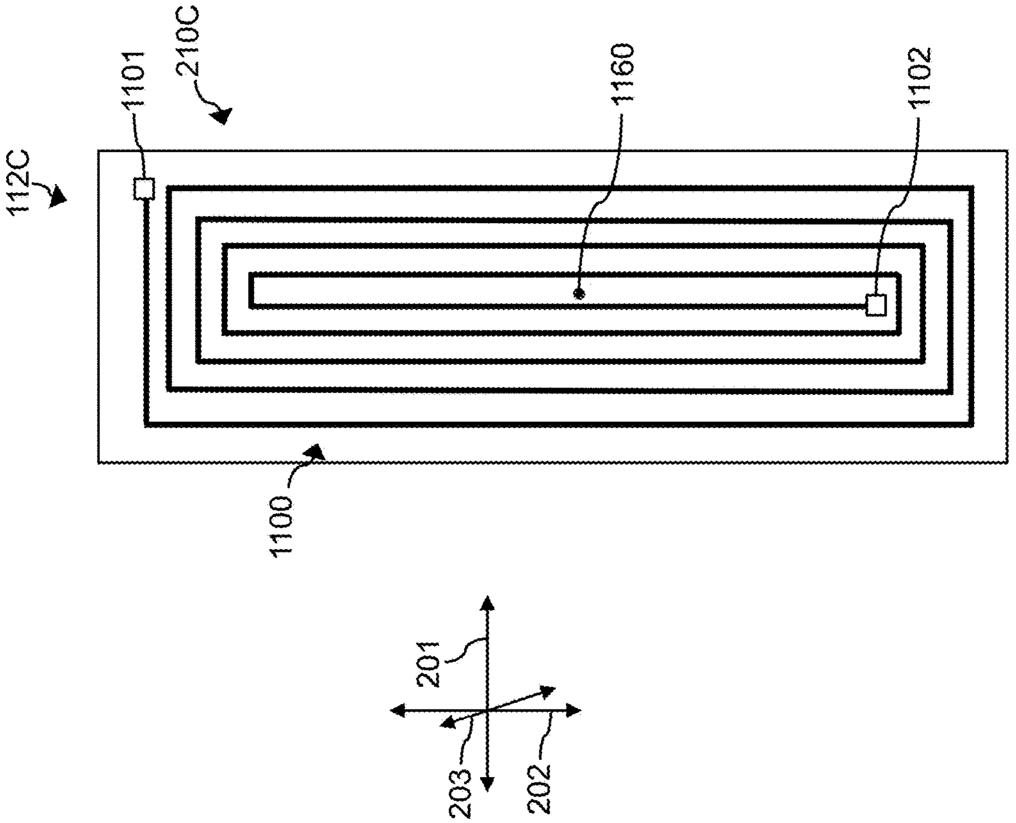
FIG. 12 is an isolated top view of the third electrically conductive coil illustrated in FIG. 2 according to another embodiment.

The spiral 210C has a plurality of interconnected loops 1100 and is wound about an axis 1160 that is parallel to the third axis 203. The windings can be closely spaced to increase the density of the spiral 210C. The spiral 210C is wound is a clockwise direction with respect to the axis 1160. In another embodiment, the spiral 210C is wound is a counterclockwise direction with respect to the axis 1160, for example as illustrated in FIG. 12.

A large number of turns in the spiral 210C and/or a large cross-sectional area of the spiral 210C, which can be achieved by using a plurality (e.g., some or all) of metal layers to form the spiral 210C, can increase the EMF induced by the third electrically conductive coil 112C.

Figure 13:
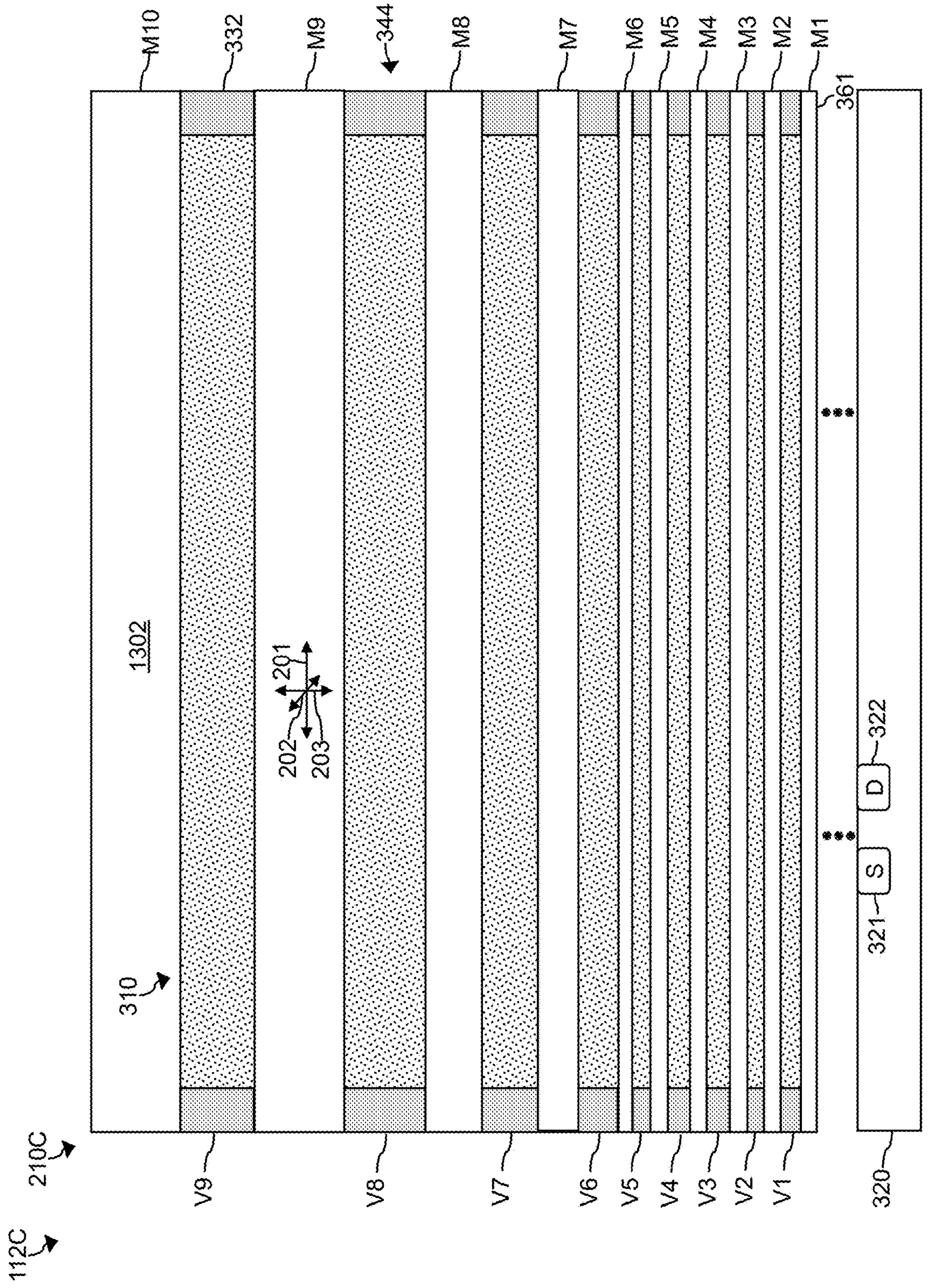
FIG. 13 is a first cross section of the spiral in the third electrically conductive coil in FIG. 11 according to an embodiment

FIG. 13 is a cross section of the spiral 210C in the third electrically conductive coil 112C through plane 1300 in FIG. 11 according to an embodiment. In this embodiment, the spiral 210C includes a plurality of metal layers 300 and a plurality of insulation layers 310 that are disposed on the semiconductor substrate 320. Active elements such as a source 321 and a drain 322 can be defined on or in the portion of the semiconductor substrate 320 beneath the spiral 210C.

The spiral 210C includes a plurality of wires 1302 formed in a plurality of metal levels M1-M10. The wires 1302 are vertically stacked and aligned. The wires 1302 in neighboring metal levels are electrically connected by one or more conductive vias 332 that is/are formed in a respective insulation layer 310.

Figure 14:
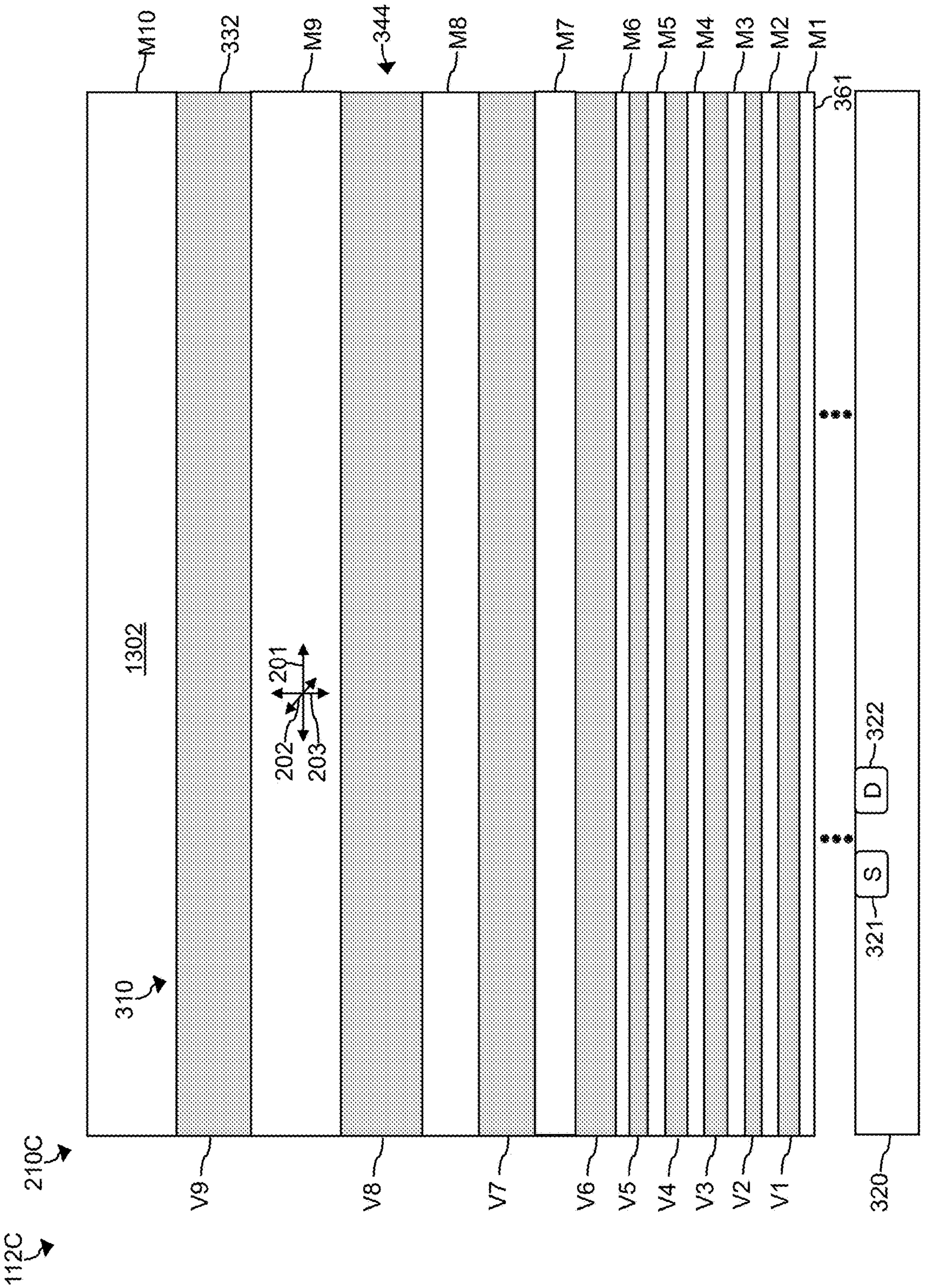
FIG. 14 is a first cross section of the spiral in the third electrically conductive coil in FIG. 11 according to another embodiment.
Figure 15:
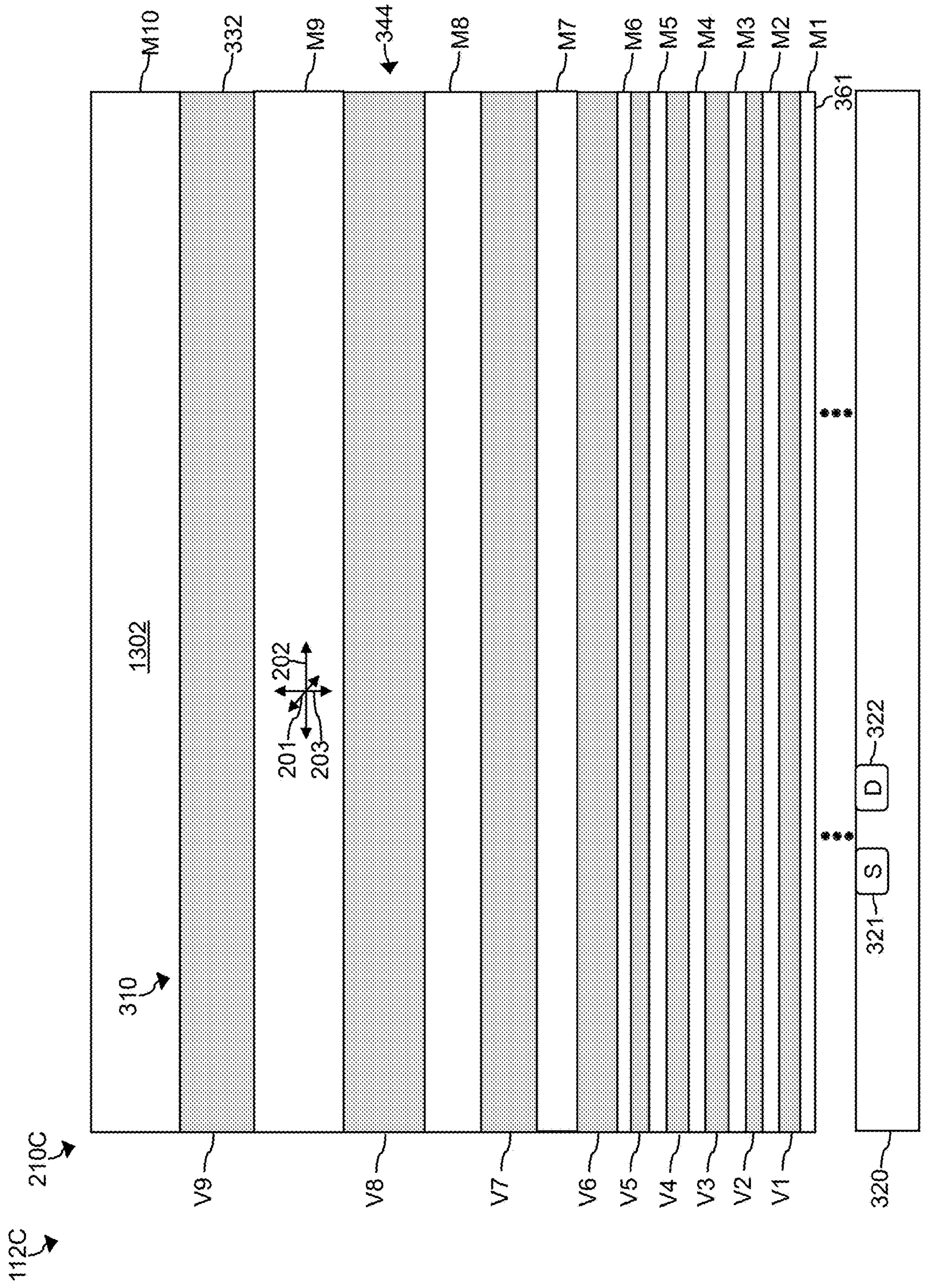
FIG. 15 is a second cross section of the spiral in the third electrically conductive coil according to an embodiment
Figure 16:
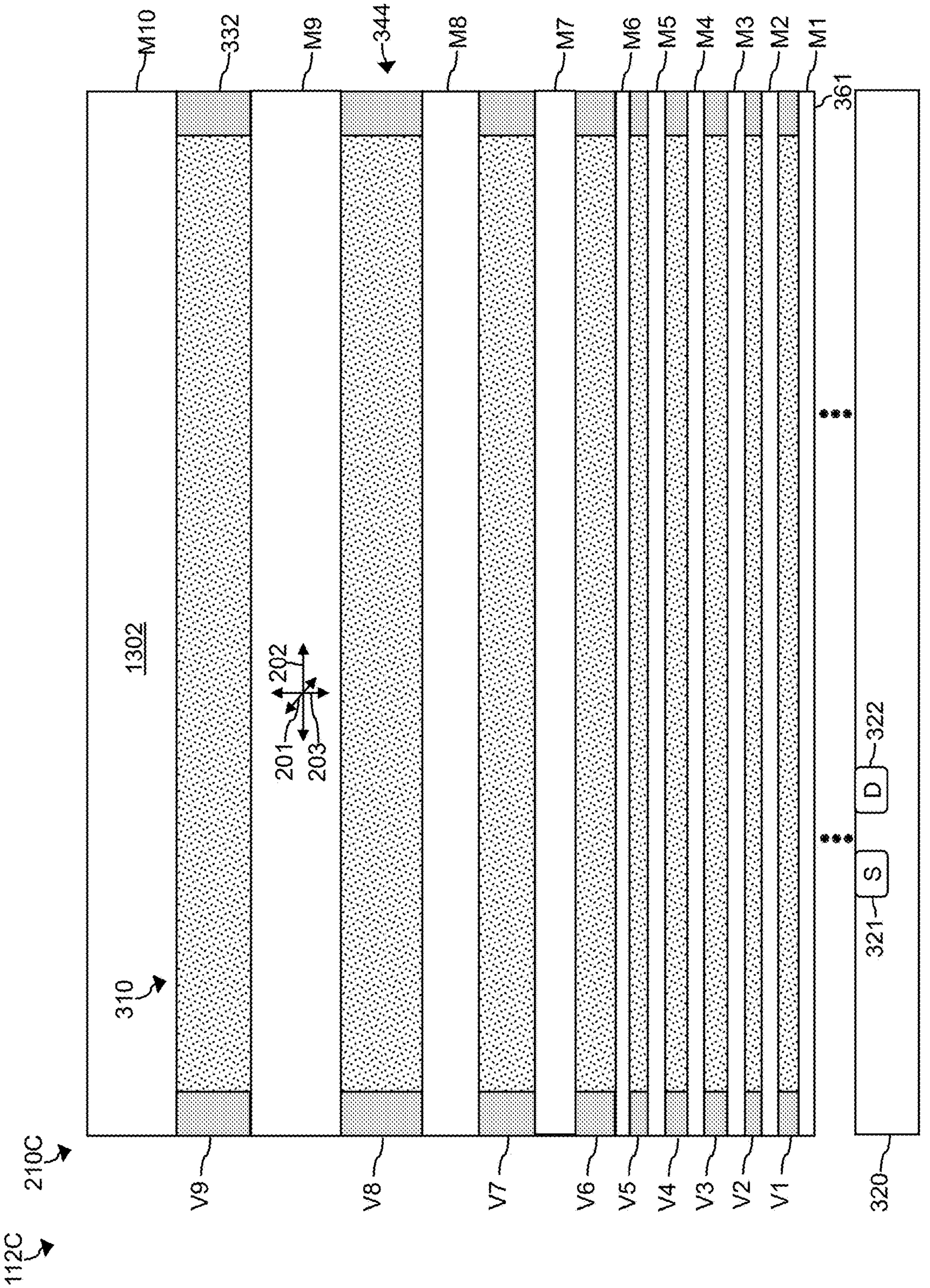
FIG. 16 is a second cross section of the spiral in the third electrically conductive coil according to another embodiment.

In some embodiments, the vias 332 and the wires 1302 can have the same or approximately the same length and/or width, for example as illustrated in FIG. 14, to maximize the cross-sectional area of the spiral 210C and of the third electrically conductive coil 112C. In FIG. 14, the vias 332 and the wires 1302 have the same length, which can be measured with respect to the first axis 201. In FIG. 15, which is a cross section of the spiral 210C in the third electrically conductive coil 112C through plane 1500 in FIG. 11 according to an embodiment, the vias 332 and the wires 1302 have the same width, which can be measured with respect to the second axis 202. As such, the vias 332 and the wires 1302 can, in combination, form interconnected metal loops 1100 that are solid and/or a continuous metal structure with respect to the third axis 203 along the length of the spiral 210C. FIG. 16 is a is a cross section of the spiral 210C through plane 1500 in FIG. 11 according to the embodiment illustrated in FIG. 13.

For the spiral third electrically conductive coil 112C illustrated in FIGS. 11 and 12, Z, the equivalent definition of N.A. in Eq. (6) changes to:

$$N.A. = A1 + A2 + \ldots\ An \tag{15}$$

where A1 denotes the area of the outer-most loop 1100, A2 denotes the area of the second loop 110, and so on. As evident from Eq. (15), a multi-turn spiral coil would produce a correspondingly large EMF. To achieve that, the third electrically conductive coil 112C can be designed with minimum width and spacing requirements set by the design-rule check (DRC) in order to achieve the maximum number of turns for a given area. To achieve a further increase in the effective area, identical coils can be implemented in some or all the metal layers such as from M1 on bottom to M10 on top, as illustrated in FIGS. 13-16, and are stacked together to form a single spiral spanning some or all the available metal layers.

Figure 17:
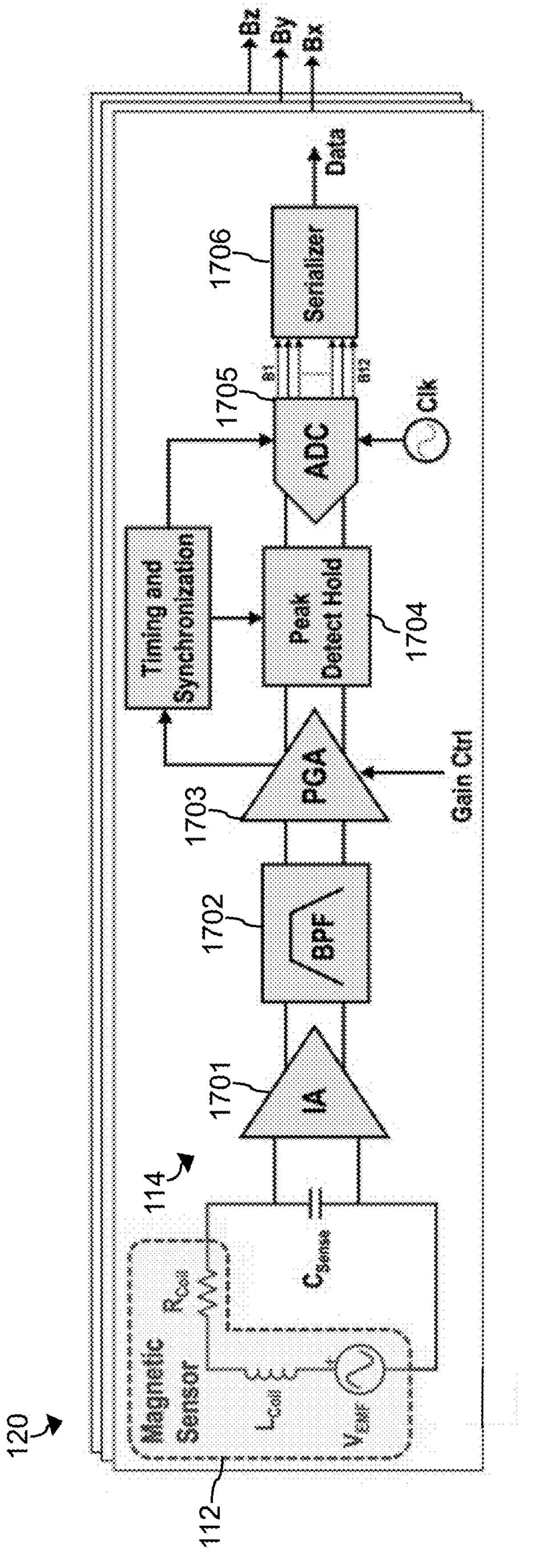
FIG. 17 is a block diagram of the equivalent circuits formed in the semiconductor chip of the 3D magnetic field sensor for the first and second electrically conductive coils.

FIG. 17 is a block diagram of the equivalent circuits formed in the semiconductor chip 120 of the 3D magnetic field sensor 110.

The circuits include an instrumentation amplifier (IA) 1701, a band-pass filter (BPF) 1702, a programmable gain amplifier (PGA) 1703, a peak-detect-and-hold (PDH) circuit 1704, and an analog-to-digital (ADC) converter 1705, and a serializer 1706. The input of the IA 1701 is electrically coupled to an electrically conductive coil 112 (e.g., electrically conductive coil 112A or 112B). The output of the IA 1701 is electrically coupled to the input of the BPF 1702. The output of the BPF 1702 is electrically coupled to the input of the PGA 1703. The output of the PGA 1703 is electrically coupled to the input of the PDH circuit 1704. The output of the PDH circuit 1704 is electrically coupled to the input of the ADC 1705. The output of the ADC is electrically coupled to the input of the serializer 1706.

Each electrically conductive coil 112 is represented as an inductor $L_{Coil}$ having a parasitic resistance $R_{Coil}$. The oscillating (e.g., AC) magnetic field gradient produced by the 3D magnetic field generator 100 (FIG. 1) induces an EMF in the inductor $L_{Coil}$ having a corresponding oscillating voltage $V_{EMF}$.

The parasitic resistance $R_{Coil}$ introduces a wideband noise of $\sqrt{4kTR_{coil}}$ with units $$\frac{V}{\sqrt{Hz}}$$

where k is Boltzman's constant and T is the temperature in degrees Kelvin. An optional sensing capacitor $C_{sense}$ can reduce the wideband noise to $\sqrt{kT/C_{sense}}$. $C_{sense}$ cannot be arbitrarily large for noise suppression since the RC lowpass frequency should be higher than the EMF signal's frequency of about 100 Hz to about 100 kHz including about 500 Hz. $R_{Coil}$ can be out about 10 MOhm to about 10 MOhm including about 2 MOhm, about 6 MOhm, about 8 MOhm, and any value or range between any two of the foregoing values, for each electrically conductive coil 112 (e.g., for the first electrically conductive coil 112A (e.g., the X magnetic sensor), for the second electrically conductive coil 112B (e.g., the Y magnetic sensor), and for the third electrically conductive coil 112C (e.g., the Z magnetic sensor). The parasitic resistance $R_{Coil}$ can be the same or different for each electrically conductive coil 112. In an example, when $R_{Coil}$ is 8MΩ for the first and second electrically conductive coils 112A, B and is 5.4MΩ for the third electrically conductive coil 112C, there is a thermal noise floor of 364 nV/$\sqrt{Hz}$ for first and second electrically conductive coils 112A, B and of 300 nV/$\sqrt{Hz}$ for the third electrically conductive coil 112C.

To provide a magnetic-field resolution of ≤10 μT for the 3D magnetic field sensor 110 in each axis, the electrically conductive coils 112A-C were simulated with 10 μT oscillating magnetic fields at a frequency of 500 Hz to determine the tolerable noise floor for the front-end circuit blocks. The first and second electrically conductive coils 112A, B generated 660 nV of EMF while the Z-sensor generated 40 μV of EMF in response to the 10 μT field. Since the EMF of the first and second electrically conductive coils 112A, B is close to their thermal noise floor, the front-end instrumentation amplifier (IA) 1701 can have about a 5× to about a 10×, including any subranges, lower input-referred noise (IRN) floor, i.e. ≈40 nV/$\sqrt{Hz}$, as detailed below.

Figure 18:
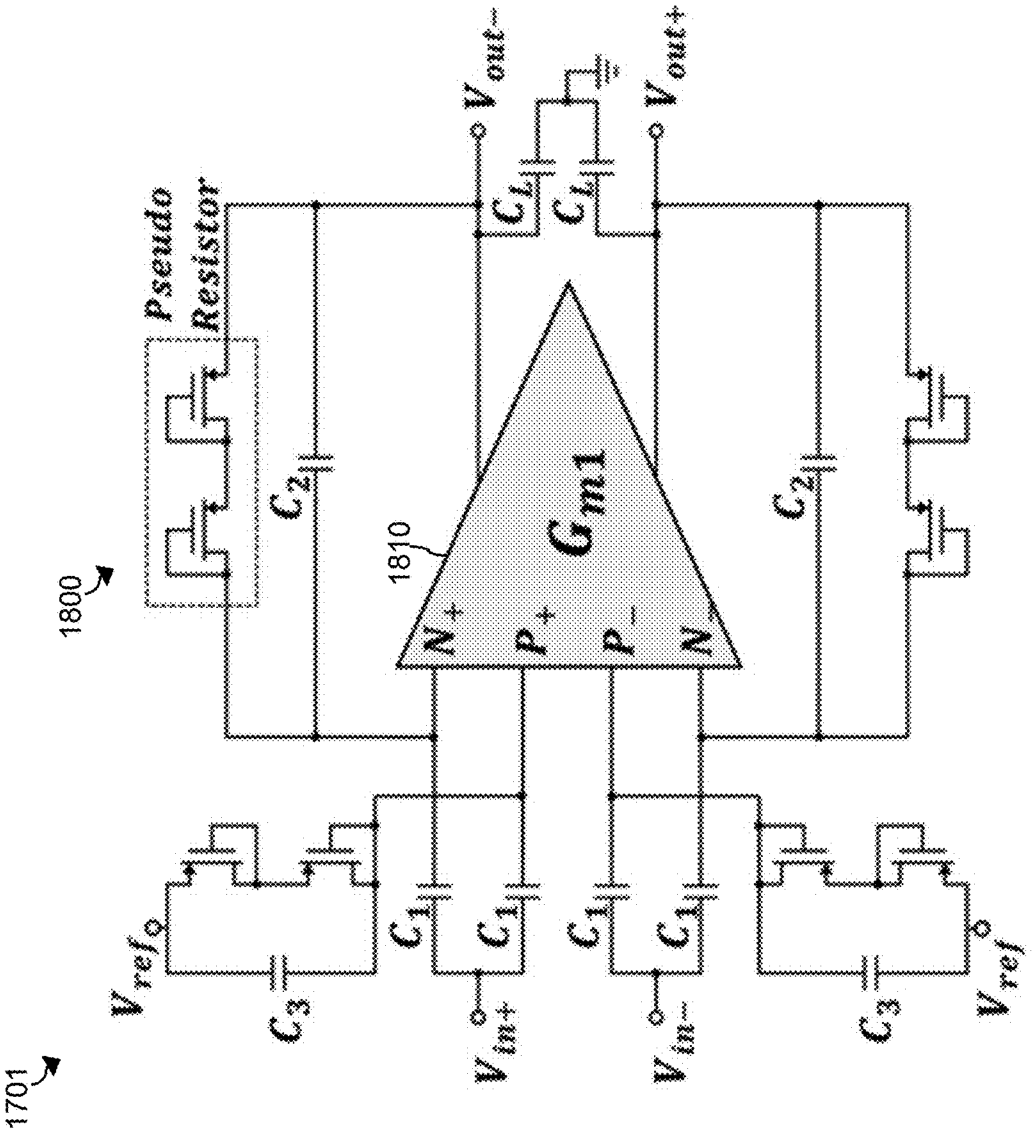
FIG. 18 which is a circuit diagram of the instrumentation amplifier illustrated in FIG. 17.

The IA 1701 is capacitively coupled to the input to avoid DC offsets and low frequency noise, as illustrated in FIG. 18 which is a circuit diagram of the IA 1701. The IA 1701 can be implemented in a fully-differential closed-loop architecture to achieve high common-mode noise rejection and ensure sufficient linearity. The input coupling capacitor $C_1$ can be $X^*C_2$ where X can be about 10 to about 100, including about 25, about 50, about 75, and any value or range between any two of the foregoing values. The value of X can be determined based on the required gain, the total capacitance value, the area limitation, and/or other factors. In one example, $C_2$ can be about 230 fF metal-oxide-metal (MOM) capacitor, rendering a total closed-loop gain of 50V/V. The gain is not kept to be very high to avoid amplifying the input noise. Pseudo-resistors 1800 realized using transistors can be added in the feedback path of the IA 1701 to provide GΩ-level impedance, which can be used to set the high-pass corner frequency to be within about 10 to about 100 Hz including any subranges. The low-pass corner frequency of the IA 1701 is determined by the output impedance of the $G_{m1}$ block 1810 and the load capacitor $C_L$, which can be about 25 pF. The value of the load capacitor $C_L$ can be determined based on the required gain, the total capacitance value, the area limitation, and/or other factors.

Figure 19:
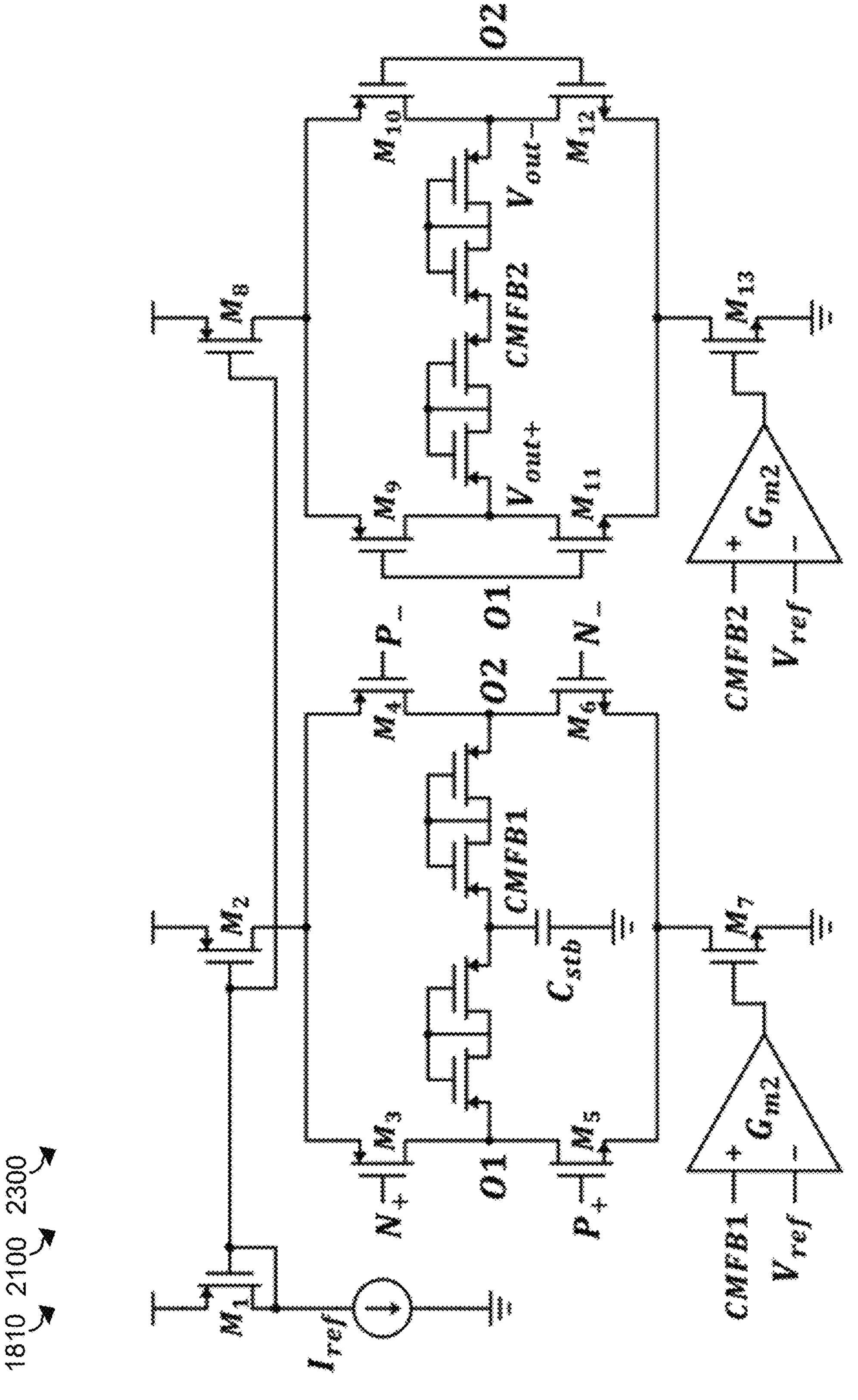
FIG. 19 is a circuit diagram of the $G_{m1}$ block of the instrumentation amplifier illustrated in FIG. 18.
Figure 20A:
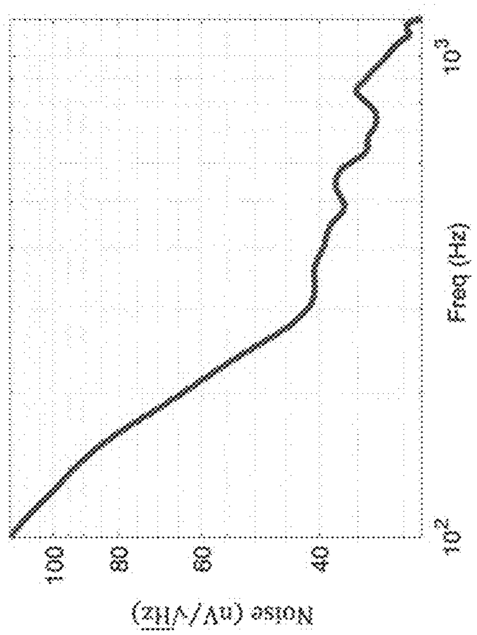
FIG. 20A is a graph of the input-referred noise the measured IRN of the of the instrumentation amplifier illustrated in FIG. 17 as a function of frequency.
Figure 20B:
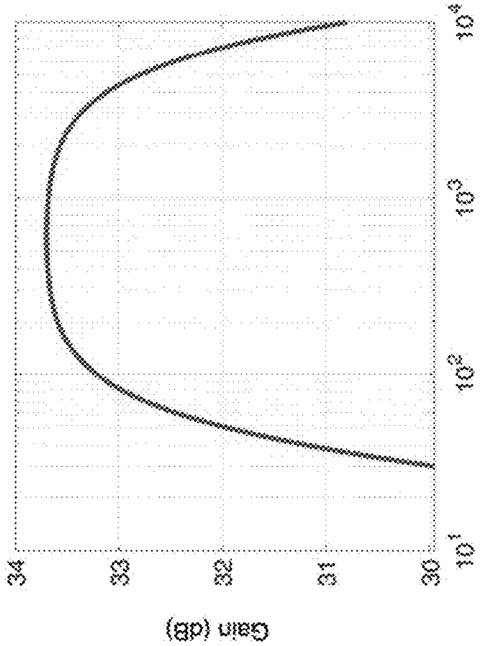
FIG. 20B is a graph of gain as a function of frequency.

The $G_{m1}$ block 1810 can be implemented as a cascade of two current-reuse stages, as illustrated in FIG. 19. Since both $M_3$ and $M_5$ (and $M_4$ and $M_6$) carry the same current, the IRN of the first stage is given by:

$$\text{Input Referred Noise}\left(V^2/\text{Hz}\right) = \frac{16kT}{3} * \frac{1}{g_{m3} + g_{m5}} \tag{16}$$

where k is Boltzmann's constant, T is the absolute temperature, and $g_{m3}$ and $g_{m5}$ are the transconductances of $M_3$ and $M_5$ respectively. In the absence of the current-reuse topology, the last term in Eq. (16) reduces to $1/g_{m3}$ (or $1/g_{m5}$), illustrating that this topology helps reduce the noise power by half. Due to the high $g_m$ requirement of stage-1 for achieving low noise, it is the most power-hungry block in the entire design with a bias current of 800 nA flowing through $M_2$ from a supply voltage (Vdd) of 1.2 V. The bias current in stage-2 can be up to 10× lower. The total power consumption of the IA 1701 can be 1.3 μW. 2.5V thick-oxide transistors can be used to minimize gate leakage and can be operated in the sub-threshold regime to further reduce the noise. To reduce the 1/f flicker noise, input stage transistors ($M_3$-$M_6$) can be designed with a large gate area with each having a width in the range of about 100 μm to about 1,000 μm including about 200 μm, about 400 μm, about 600 μm, about 800 μm, any value or range between any two of the foregoing values. The measured IRN of the IA 1701 is lower than 40 nV/$\sqrt{\text{Hz}}$ at or near the example EMF signal's frequency of 500 Hz, as illustrated in FIG. 20A. The measured frequency response of the IA 1701 shows that 500 Hz is well within the pass-band, as illustrated in FIG. 20B.

For the IA 1701, the relatively low gain is compensated later in the chain using the PGA after the sensitive EMF signal is filtered by the bandpass filter following the IA. Pseudo-resistors are used in the IA 1701 to bias the non-feedback nodes $P_+$ and $P_-$ to $V_{ref}$ which can be equal to Vdd/2. By separating the biasing of the $N_+$ and $P_+$ nodes (and similarly $N_-$ and $P_-$ nodes), the two can be biased independently to drive both NMOS and PMOS transistors using the same input signal $V_{in+}$ (and similarly $V_{in-}$) [31]. The common-mode voltage at the output of each stage of the IA 170 can be set to $V_{ref}$ (chosen as Vdd/2) using $G_{m2}$, which can be chosen independently of the $V_{ref}$ used for biasing the non-feedback path. The differential outputs of the PGA 1702 can also be centered around a common mode voltage of Vdd/2=600 mV on the semiconductor chip 120.

The IA 1701 is used at the front-end of the first and second electrically conductive coils 112A, B due to their stringent noise requirement compared to the third electrically conductive coil 112C which is directly connected to a band-pass filter (BPF) 1702 (FIG. 17). In other words, the equivalent circuits for the first and second electrically conductive coils 112A, B include the IA 1701 which has an input that is electrically coupled to the first electrically conductive coil 112A (in the equivalent circuit for the first electrically conductive coil 112A) or to the second electrically conductive coil 112B (in the equivalent circuit for the second electrically conductive coil 112B). In the equivalent circuits for the first and second electrically conductive coils 112A, B, the output of the IA 1701 is electrically coupled to the input of the BPF 1702. In the equivalent circuits for the third electrically conductive coils 112C, the output of the IA 1701 is electrically coupled to the input of the BPF 1702, as illustrated in FIG. 21.

Figure 21:
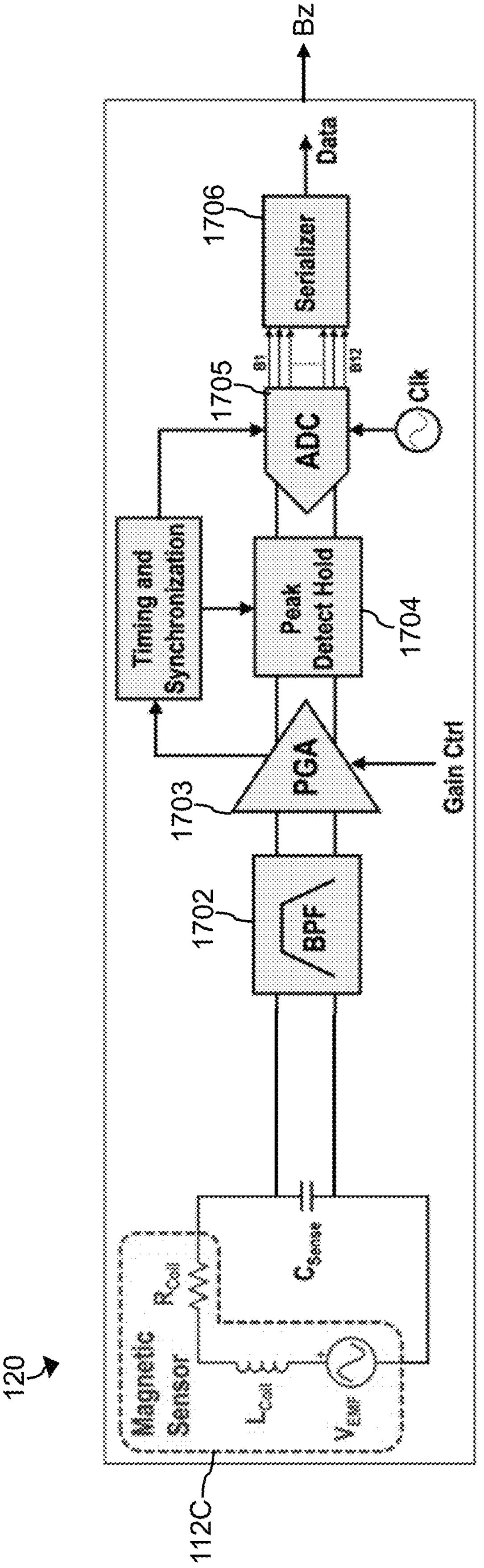
FIG. 21 is a block diagram of the equivalent circuits formed in the semiconductor chip of the 3D magnetic field sensor for the third electrically conductive coil.
Figure 22:
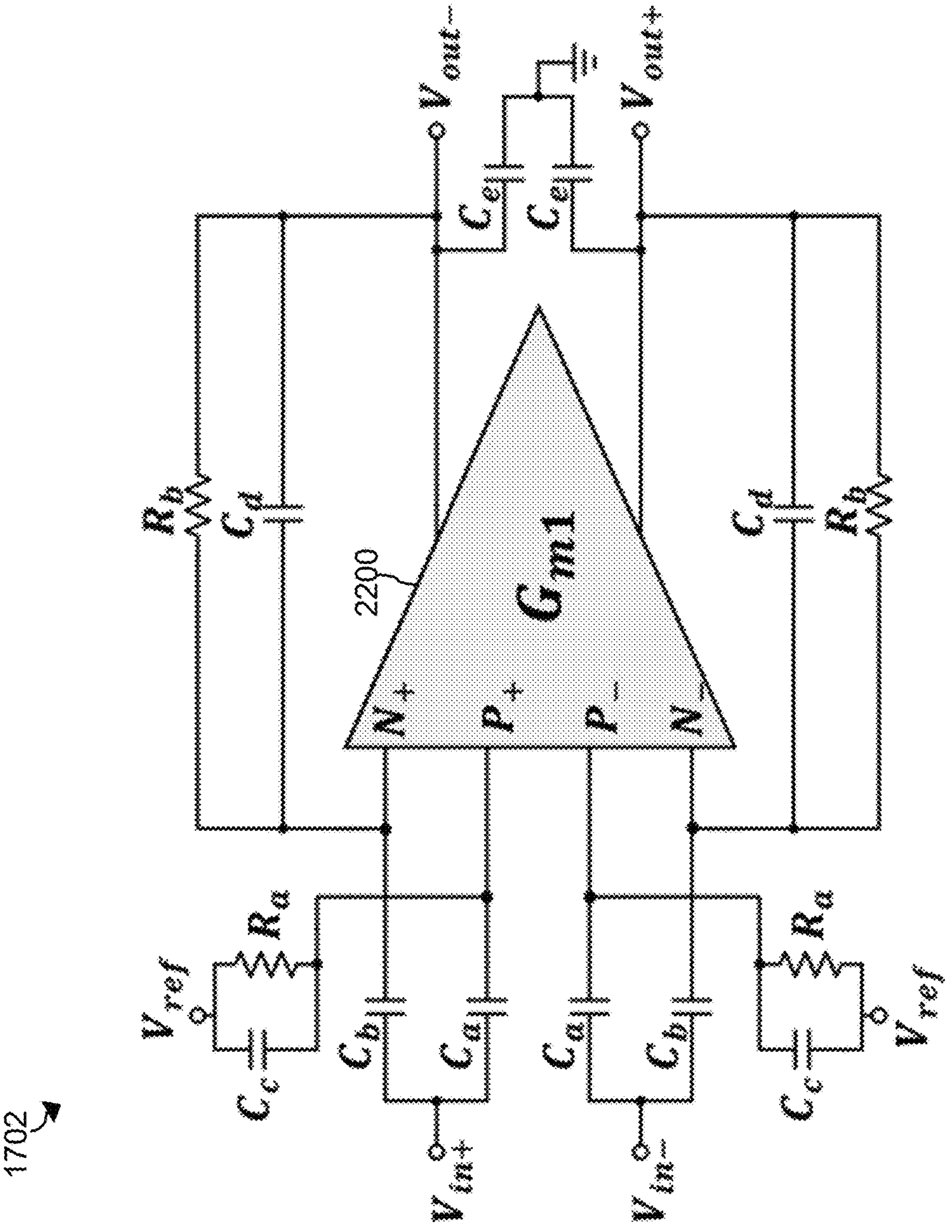
FIG. 22 is a circuit diagram of the band-pass filter illustrated in FIG. 17 according to an embodiment.

FIG. 22 is a circuit diagram of the BPF 1702 according to an embodiment. The BPF 1702 is configured to filter out the excessive out-of-band noise and improve the signal-to-noise ratio (SNR). This BPF 1702 is implemented as a capacitively-coupled, fully-differential and closed-loop architecture. The BPF 1702 can be implemented in other architectures, as understood by those of skill in the art. To achieve a sharp BPF response, the low-pass corner frequency should be lower than the high-pass corner frequency, resulting in the intersection of the two responses in their steep slope regions to yield a sharp filter response. A slight disadvantage of this is less than unity gain at the output, which can be about 0.4V/V at a center frequency of 500 Hz, which is not problematic since the gain can be compensated by the programmable gain amplifier (PGA) 1703 (FIGS. 17, 21) in the following block. The $G_{m1}$ stage 2100 of the BFP 1702 can be implemented in the same manner as the $G_{m1}$ block 1810 of the IA 1701. Thus, the circuit diagram of the $G_{m1}$ block 1810 in FIG. 19 can also be a circuit diagram of the $G_{m1}$ stage 2100. Since the output impedance of $G_{m1}$ of the BFP 1702 helps control the filter response, the biasing node of the output stage (gate terminal of $M_8$ in FIG. 19) is controlled externally by a tunable DC voltage and not by the on-chip reference current $I_{ref}$ (FIG. 19). This can allow the filter response to be adjusted post-fabrication, especially because the transistors are operated in the sub-threshold regime which is more susceptible to process variations. Example values of the passive components used in the BPF are: $C_a$=1 pF, $C_b$=15 pF, $C_c$=1 pF, $C_d$=1 pF, $C_e$=106 pF, $R_a$=10.4kΩ and $R_b$=105.5kΩ. Other values can be used in other embodiments. The resistors $R_a$ and $R_b$ are not implemented as pseudo-resistors as those are more prone to process variations, which are undesirable for the BPF. $V_{ref}$ is chosen as Vdd/2 which can be in the range of about 500 mV to about 800 mV, including about 600 mV, about 700 mV, and any value or range between any two of the foregoing values.

The output of the BPF 1702 is electrically coupled to the input of the PGA 1703, as illustrated in FIGS. 17, 21. The PGA 1703 can be implemented as another amplifier in other embodiments. The PGA's function is to amplify the EMF signal sufficiently for the analog-to-digital converter (ADC) 1705 (FIGS. 17, 21) to process.

Figure 23:
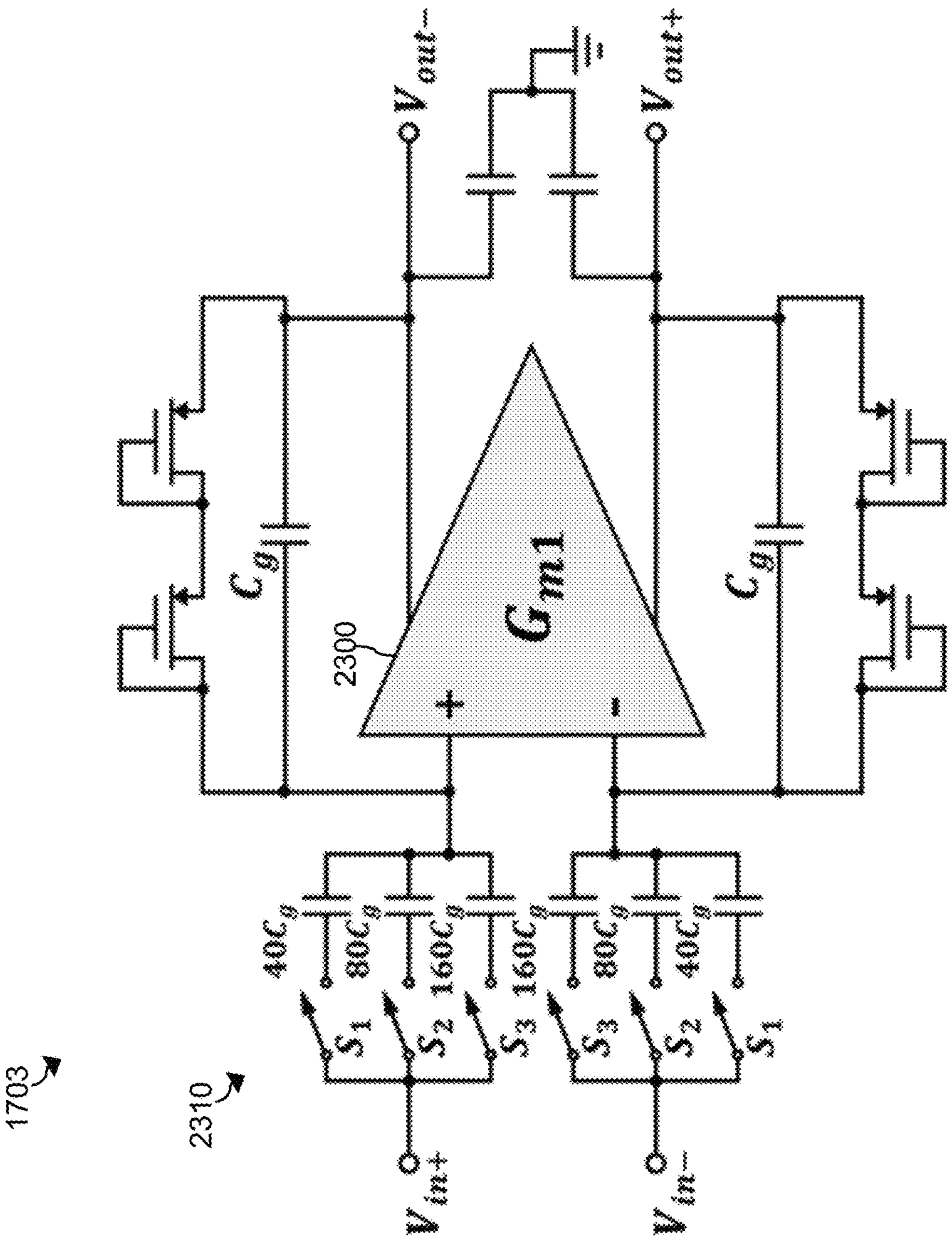
FIG. 23 is a circuit diagram of the programmable gain amplifier illustrated in FIG. 17 according to an embodiment.

The PGA 1703 can be implemented as a capacitively-coupled and fully-differential architecture but with its $N_+$-$P_+$ and $N_-$-$P_-$ nodes tied together as illustrated in FIG. 23, unlike the IA 1701 and the BPF 1702. At the input of the PGA 1703, a 3-bit tunable capacitive network 2310 is implemented to control the gain of the PGA 1703 from 40V/V to 280V/V in steps of 40V/V. The tunability accommodates the varying range of the EMF signal due to the varying peak field magnitude produced by the gradient coils throughout the field-of-view (FOV) of the 3D magnetic field generator 100. The feedback capacitor $C_g$ can be about 44.6 fF or another value. The value of the feedback capacitor $C_g$ can be determined based on the required gain, the total capacitance value, the area limitation, and/or other factors. The switches $S_1$-$S_3$ can be implemented using pass-transistor logic and driven using inverter-based drivers.

The $G_{m1}$ stage 2300 of the PGA 1703 can be implemented in the same manner as the $G_{m1}$ block 1810 of the IA 1701. Thus, the circuit diagram of the $G_{m1}$ block 1810 in FIG. 19 can also be a circuit diagram of the $G_{m1}$ stage 2300.

The measured differential outputs of the PGA 1703 for a typical mV-level input have an amplitude of about $1V_{pp}$, which is sufficient for the ADC 1705 to digitize. The total integrated noise at the output of the PGA is about 8 $mV_{rms}$ (root-mean squared) for the first and second electrically conductive coils 112A, B and about 1 $mV_{rms}$ for the third electrically conductive coil 112C, which translates to a raw magnetic field resolution of about 64 $\mu T_{rms}$ and about 8 $\mu T_{rms}$ respectively. In other embodiments, the magnetic field resolution for each electrically conductive coil 112 can be in the range of about 1 μTrms to about 100 $\mu T_{rms}$, including about 25 $\mu T_{rms}$, about 50 $\mu T_{rms}$, about 75 $\mu T_{rms}$, and any range of value between any of the foregoing values. The resolution can be further improved by averaging several consecutive samples, as discussed herein.

The output of the PGA 1703 is electrically coupled to the input of the peak detect and hold (PDH) circuit 1704, as illustrated in FIGS. 17 and 21.

Figure 24A:
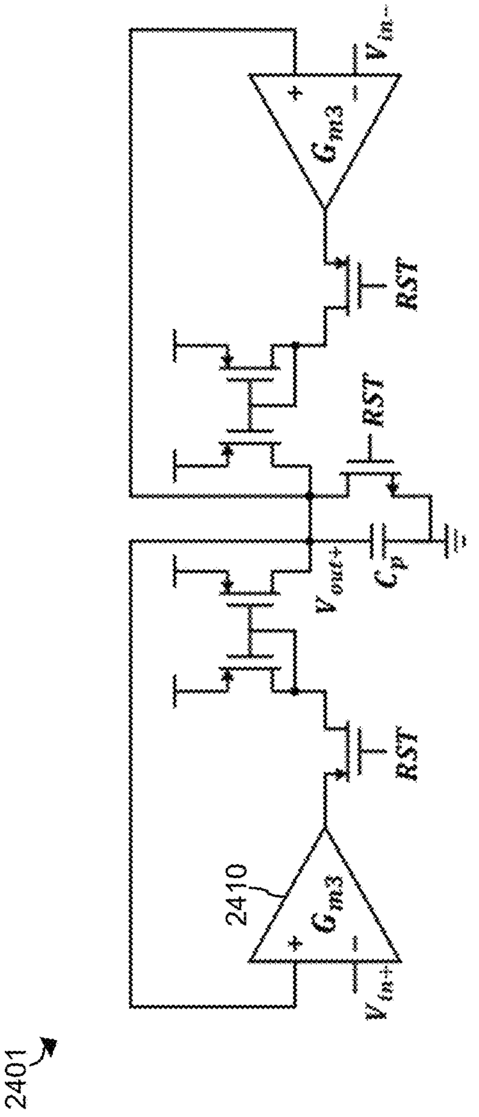
FIG. 24A is a circuit diagram of a positive differential peak detect and hold circuit according to an embodiment.
Figure 24B:
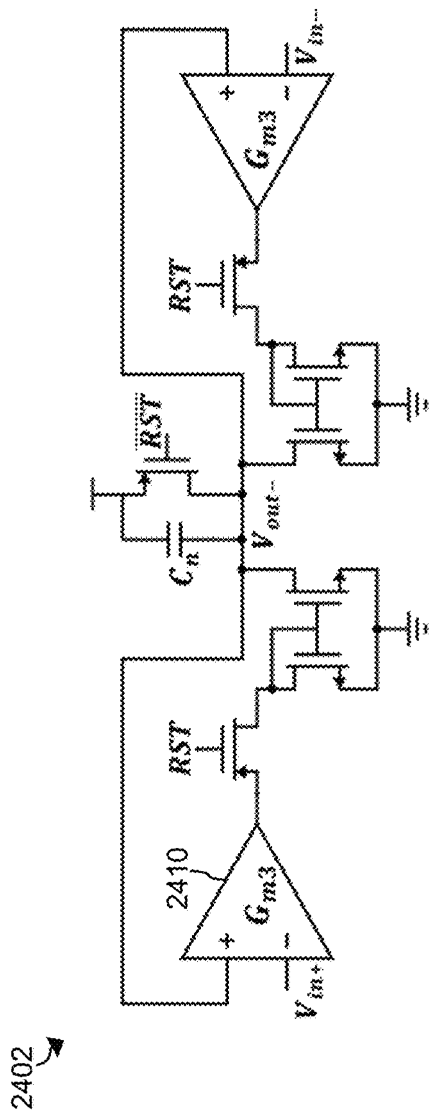
FIG. 24B is a circuit diagram of a negative differential peak detect and hold circuit according to an embodiment.

As mentioned earlier, the peak magnitude of the sinusoidal magnetic field at any given point of interest in the FOV is the only necessary signal for the purpose of position decoding. This relaxes the constraint on the ADC which can be configured to digitize only the peak values and not operate in continuous mode to reduce power significantly. To extract the peak magnitude from the differential outputs of the PGA 1703, a positive differential PDH circuit 2401 is implemented for positive peak extraction, as illustrated in FIG. 24A. In addition, a negative differential PDH circuit 2402 is implemented for negative peak extraction, as illustrated in FIG. 24B. The positive and negative differential PDH circuits 2401, 2402 operate in three modes: peak detect, peak hold, and reset.

For the positive PDH circuit 2401, as $V_{in+}$ increases, the output of $G_{m3}$ decreases, leading to an increased current in the current-mirror pair which causes $V_{out+}$ to increase until a positive peak is detected. When $V_{in+}$ starts decreasing, $V_{out+}$ is unable to follow as the hold capacitor $C_p$ (e.g., 15 pF) cannot discharge from the current-mirror transistor on top, thus holding the previous peak value. After the ADC 1705 performs digitization of the peak value stored on the hold capacitor $C_p$, the reset transistor at $V_{out+}$ (RST) discharges $C_p$ immediately for the next cycle. Since the input to the PDH is differential, an identical circuit is used to extract the positive peaks from $V_{in-}$ and its output is connected to $V_{out+}$. A similar operation takes place for negative peak extraction in the negative PDH circuit 2402.

Figure 25:
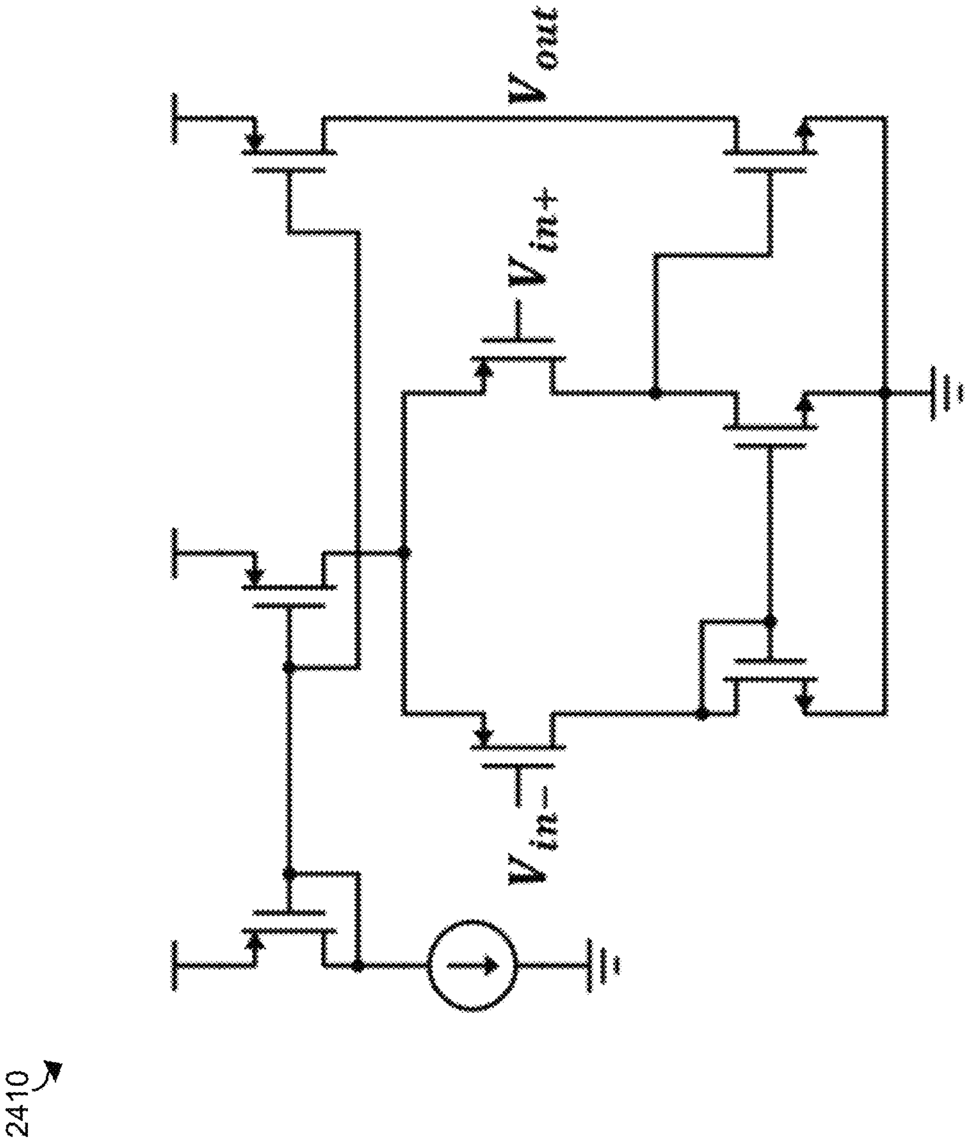
FIG. 25 is a circuit diagram of the $G_{m3}$ stage of the positive and negative differential peak detect and hold circuits illustrated in FIGS. 24A and 24B, respectively.
Figure 26A:
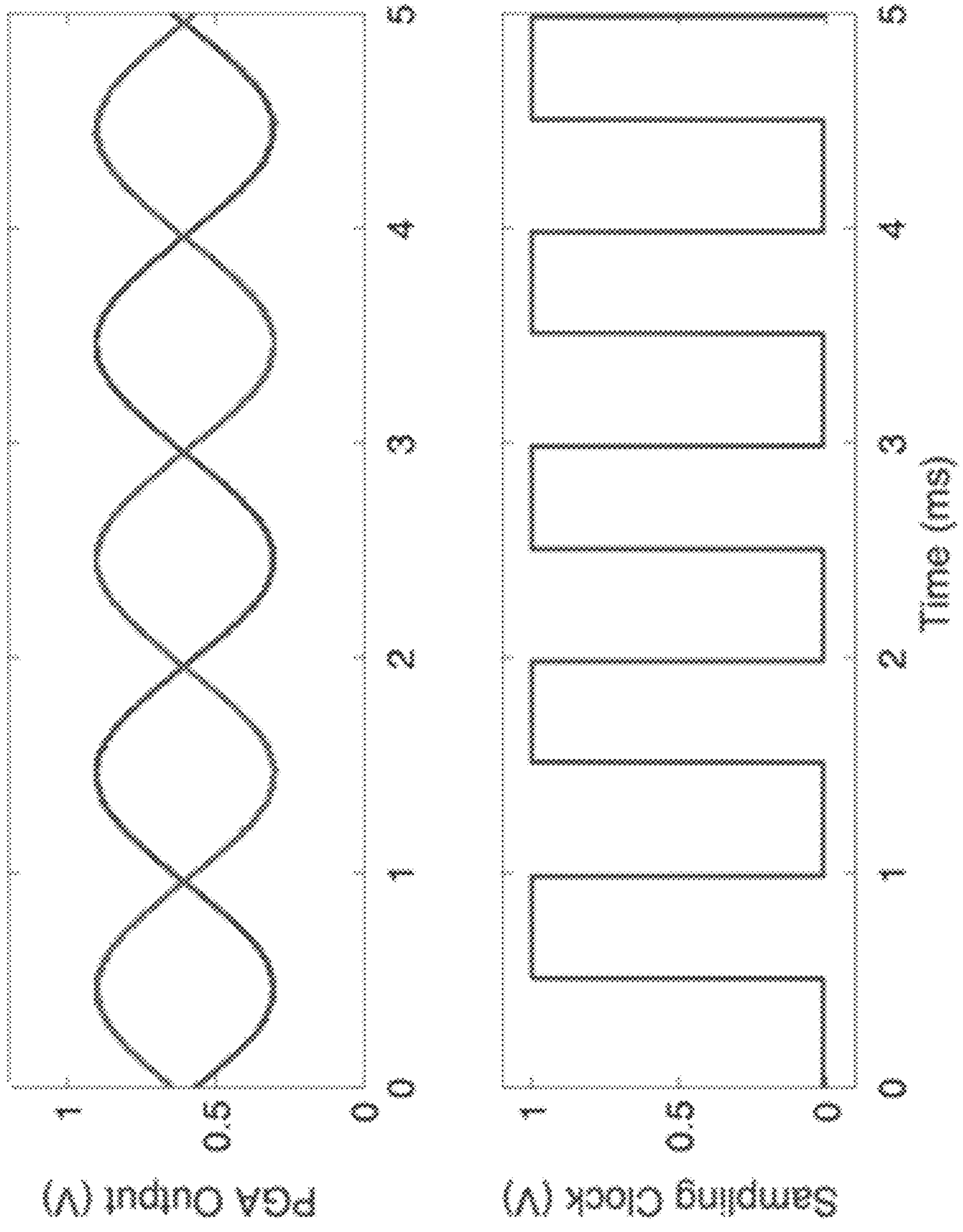
FIG. 26A illustrates a sampling clock that is synchronized with the peaks of the EMF signal.
Figure 26B:
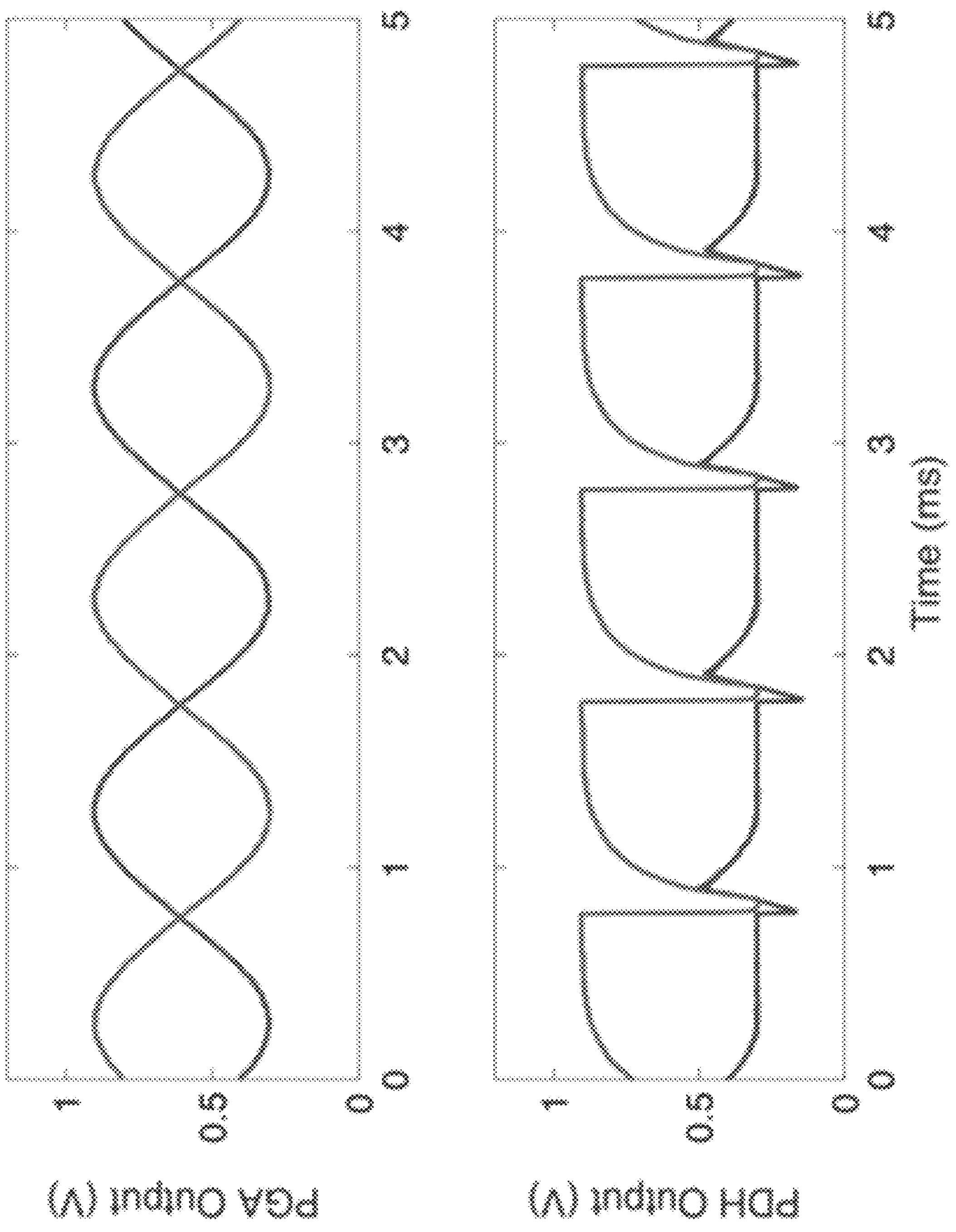
FIG. 26B illustrates graphs of the programmable gain amplifier output and the peak detect and hold circuit output.
Figure 37A:
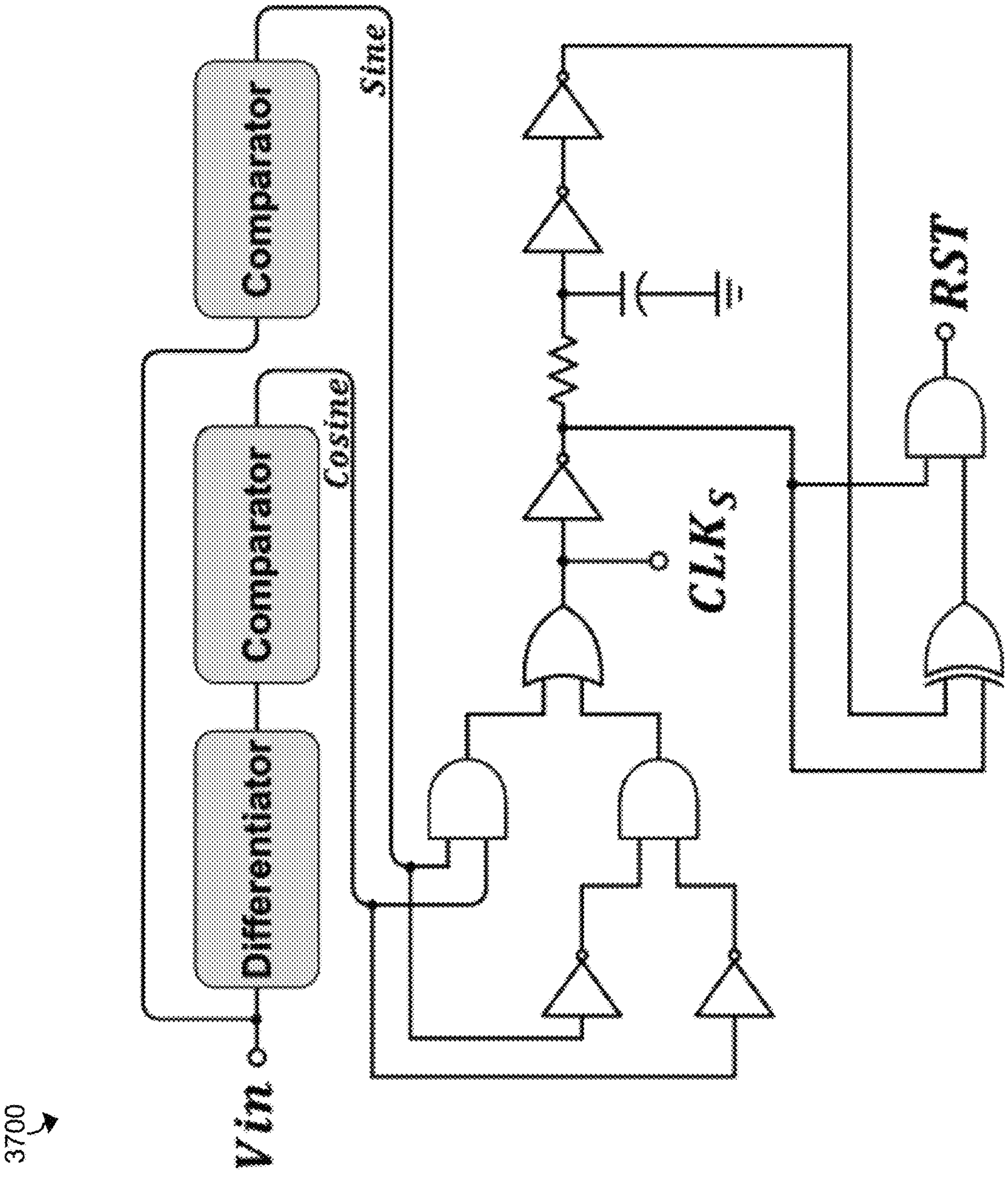
FIGS. 37A and 37B illustrate logic blocks and a digital sine signal and for producing the reset (RST) signal in FIGS. 24A and 24B.
Figure 37B:
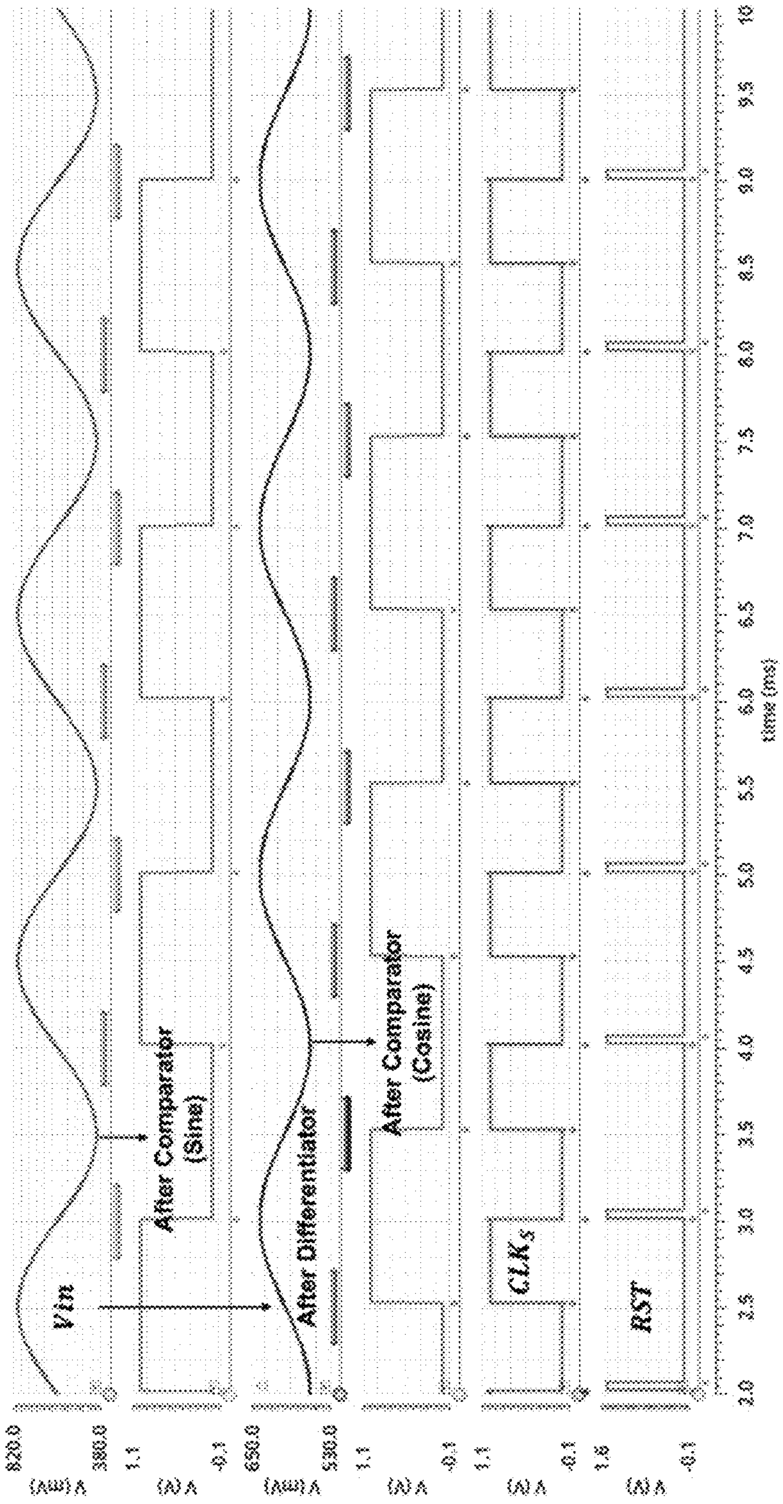

Each $G_{m3}$ stage 2410 of the positive and negative differential PDH circuits 2401, 2402 can be implemented as shown in the circuit diagram illustrated in FIG. 25. For the ADC 1705 to digitize the outputs of the PDH circuit 1704, a sampling clock can be generated that is synchronized with the peaks of the EMF signal, as illustrated in FIG. 26A. The power consumption of the complete PDH circuit 1704 can be about 1. μW such as about 1.14 μW. The sampling clock needs to be high for the duration of the peak hold time, which spans from the peak of the sinusoid to the common mode (600 mV) crossing, as illustrated in FIG. 26B. This is accomplished by converting the sine signal to rail-to-rail digital voltage using a comparator whose other input is connected to 600 mV. A cosine waveform is generated by differentiating the sine signal and is also converted to rail-to-rail digital voltage. By using an XOR operation on these two digital signals, we obtain the sampling clock shown in FIG. 26A. The reset (RST) signal in FIGS. 24A and 24B is also obtained using the digital sine signal and associated logic blocks 3700, as illustrated in FIGS. 37A and 37B.

Figure 27:
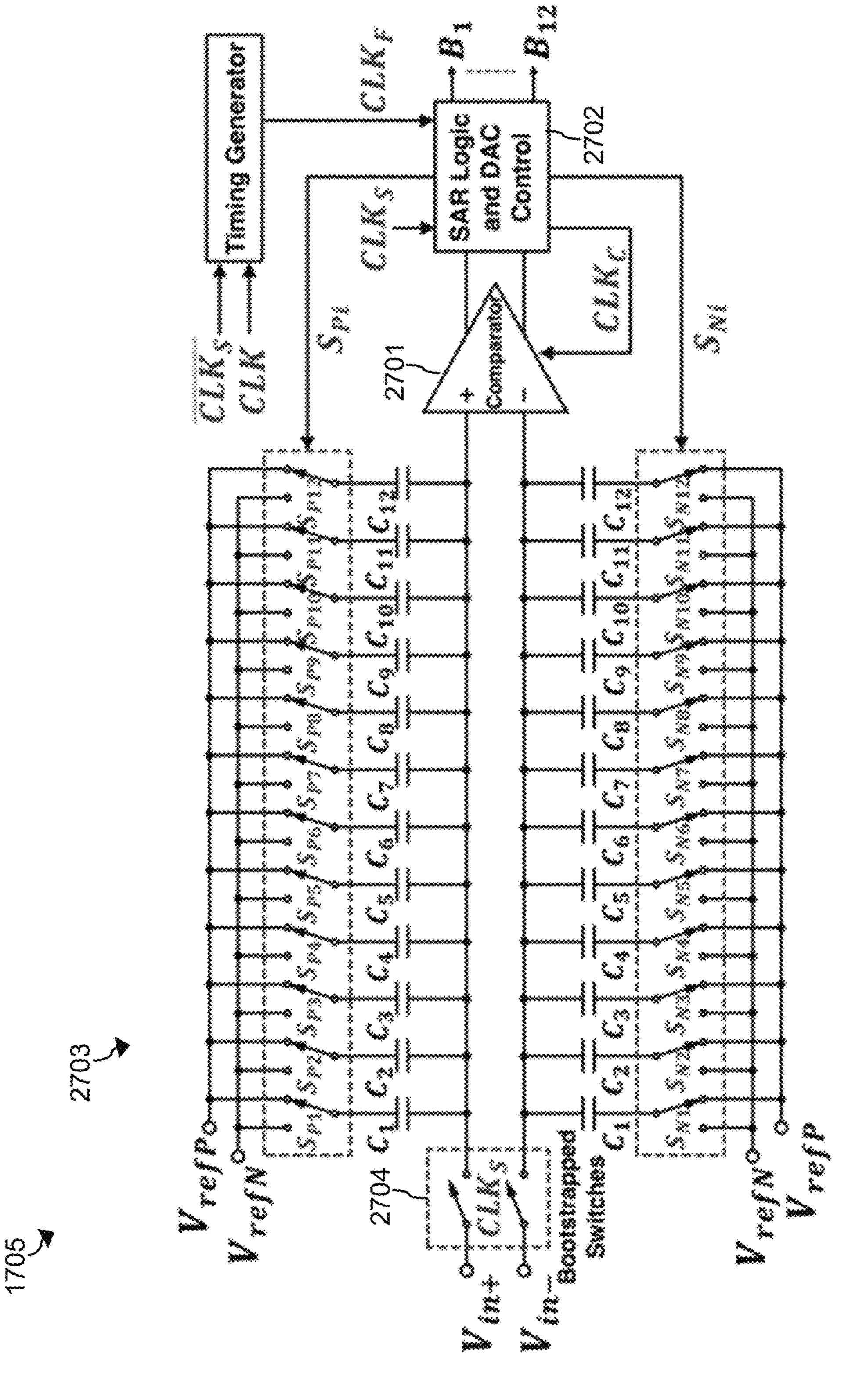
FIG. 27 is an example circuit diagram of the analog-to-digital converter illustrated in FIG. 17.

The differential outputs of the PDH circuit 1704 are fed to a 12-bit differential-input successive approximation register (SAR)-based ADC 1705. The ADC 1705 can have a different number of bits and/or a different implementation in other embodiments. An example circuit diagram of the ADC 1705 is illustrated in FIG. 27. SAR ADCs have a high power-efficiency at the relatively low sampling rate (e.g., about 20 kS/s) used for the 3D magnetic field sensor 110. By adopting a monotonic capacitor switching procedure (e.g., a downward switching procedure), as illustrated in FIG. 27, the power and area requirements are further reduced. In addition, discharging through NMOS transistors is faster compared to PMOS transistors. The ADC 1705 includes four major blocks: a comparator 2701, a capacitive digital-to-analog converter (DAC) 2702, a SAR logic block 2703, and bootstrapped switches 2704. The input is first sampled on the top plates of the capacitors via the boot-strapped switches 2704 while all the bottom plates are connected to $V_{refP}$ (1.2V). When the boot-strapped switches 2704 are turned off, the comparator 2701 performs the first comparison without switching any capacitor. If the comparator output is high (most-significant bit (MSB)=1), capacitor $C_1$ on the higher voltage side ($V_{in+}$) is switched to $V_{refN}$ (0V) and the $C_1$ on the lower voltage side (Vin_) remains unchanged. An opposite scenario is executed if MSB=0. This process is repeated until the least-significant bit (LSB) is computed. As evident, there is only one capacitor switching per bit computation, which reduces the charge transfer in the DAC and the control logic, resulting in significant power saving. The DAC capacitors can be binary weighted with $C_i=2*C_{i+1}$ for $i\in(1,10)$ and $C_{11}=C_{12}=4$ fF.

Figure 28:
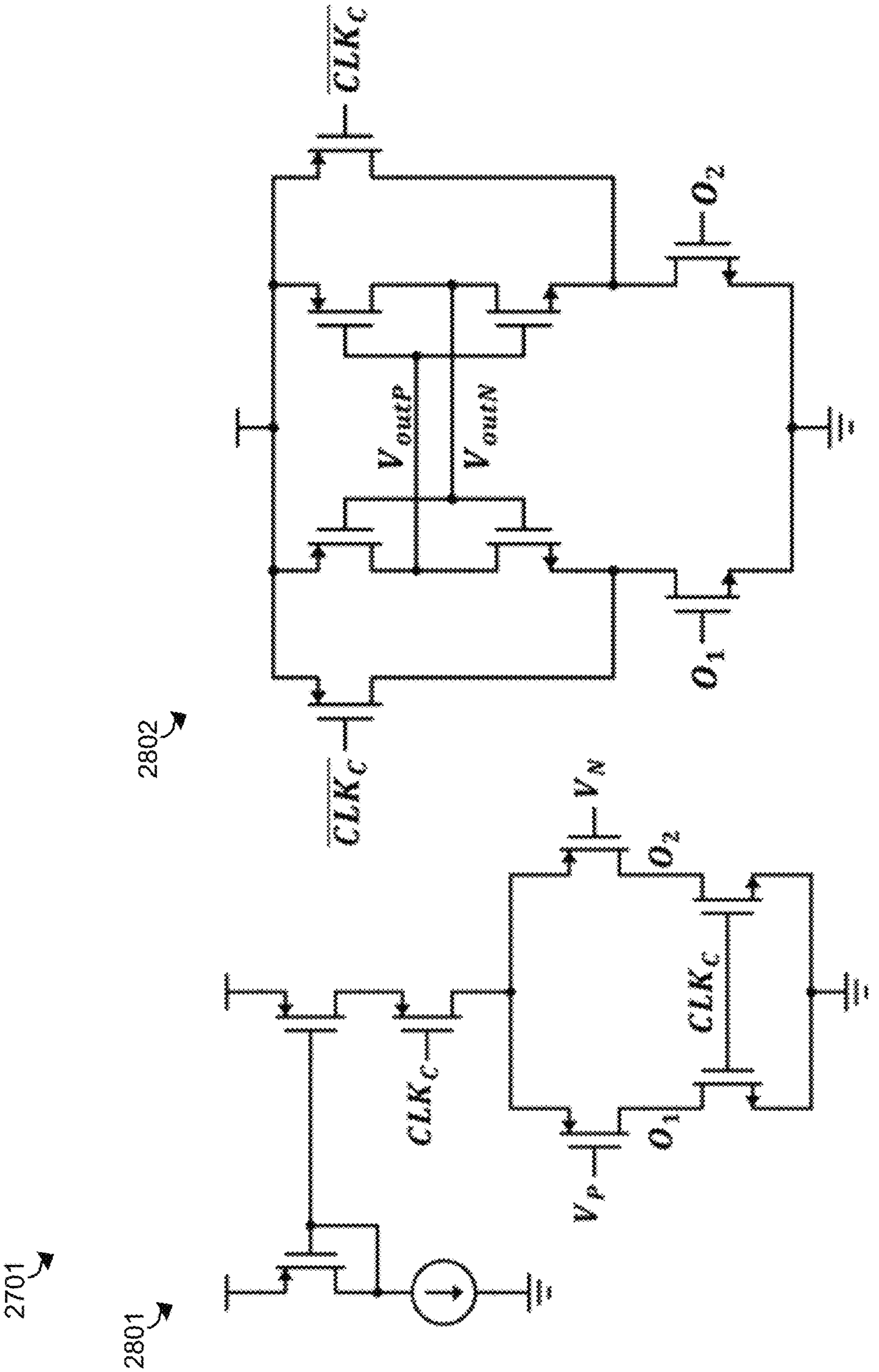
FIG. 28 is a circuit diagram of the comparator 2701 in the analog-to-digital converter illustrated in FIG. 27.

FIG. 28 is a circuit diagram of the comparator 2701 includes a pre-amplifier 2801 followed by a regenerative latch 2802 for optimum performance. The dynamic nature of the comparator ensures no static power consumption. When the ADC clock (CLK) is high, the outputs $O_1$ and $O_2$ are reset. When the clock is low, $V_p$ and $V_N$ are compared by the pre-amplifier 2801 and the result is fed to the regenerative latch 2802 to produce a digital output. By biasing the pre-amplifier's input transistors in sub-threshold regime using the current mirror on top, we achieve low noise and high power-efficiency. The SAR logic and DAC control block generate the controls and clock signals using an external 50 kHz clock. The 12-bit output of the ADC 1705 is serialized to produce a single stream of the X, Y and Z sensor data. The ADC can consume a total power of 2.26 μW.

Figure 29:
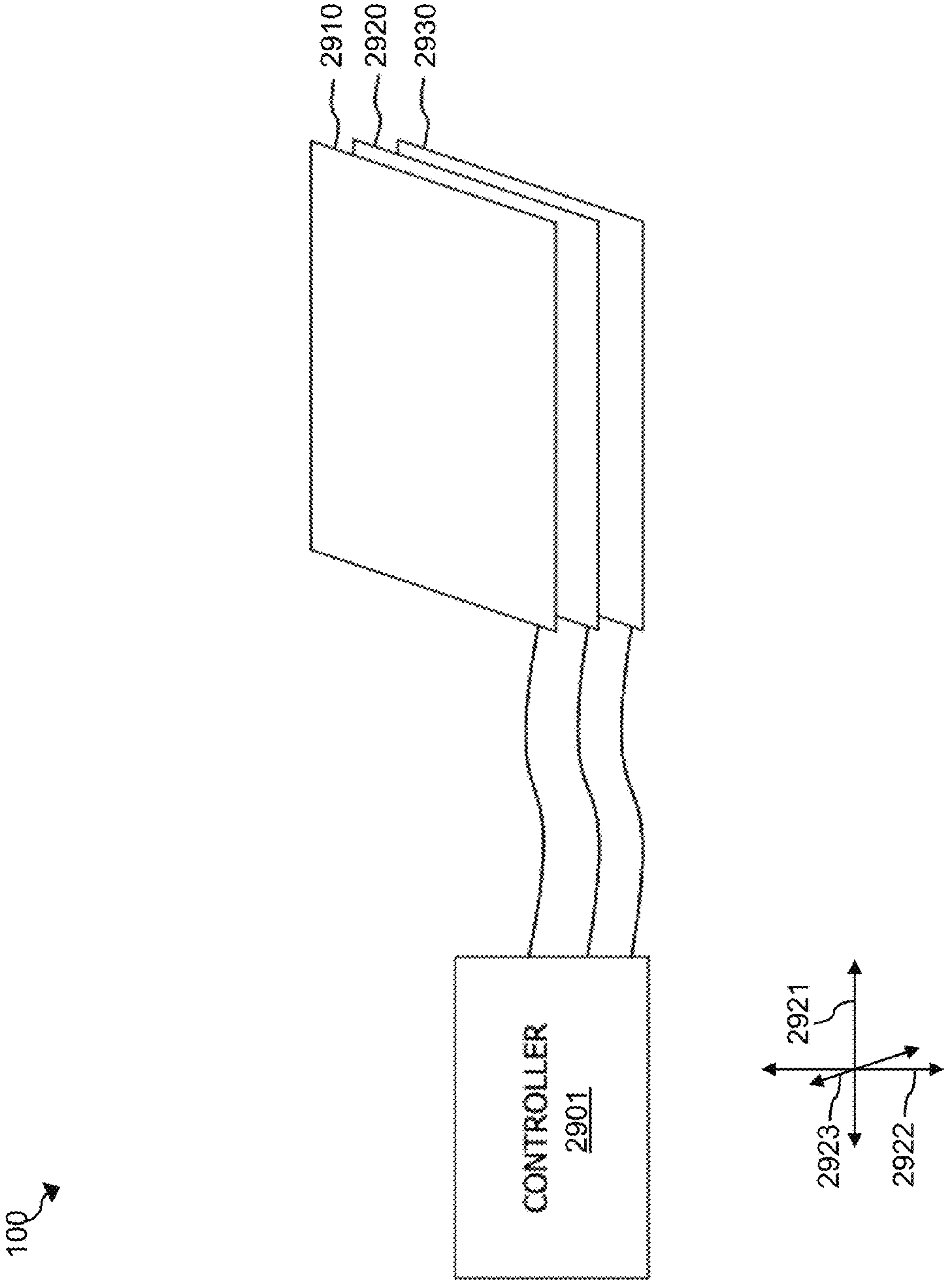
FIG. 29 is a block diagram of the 3D magnetic field generator for producing oscillating magnetic field gradients according to an embodiment.

FIG. 29 is a block diagram of the 3D magnetic field generator 100 for producing oscillating magnetic field gradients according to an embodiment. The 3D magnetic field generator 100 includes a controller 2901, a first electromagnet coil set 2910, a second electromagnet coil set 2920, and a third electromagnet coil set 2930. The first electromagnet coil set 2910 is configured to produce a first oscillating magnetic field gradient with respect to a first axis 2921 (e.g., the X axis in the Cartesian coordinate system). The second electromagnet coil set 2920 is configured to produce a second oscillating magnetic field gradient with respect to the second axis 2922 (e.g., the Y axis in the Cartesian coordinate system). The third electromagnet coil set 2930 is configured to produce a third oscillating magnetic field gradient with respect to the third axis 2923 (e.g., the Z axis in the Cartesian coordinate system). The first, second, and third axes 2921-2923 can alternatively be referred to as first, second, and third localization axes 2921-2923, respectively. Depending on the relative angular and/or rotational orientation of the 3D magnetic field sensor 110 with respect to the 3D magnetic field generator 100, the first, second, and third localization axes 2921-2923 can be parallel to or at another orientation with respect to the first, second, and third chip axes 201-203.

The electromagnet coil sets 2910, 2920, 2930 can be stacked together and/or vertically arranged (e.g., in a vertical arrangement with respect to an underlying surface) along the third axis. The electromagnet coil sets 2910, 2920, 2930 are preferably centered (e.g., concentrically centered) and/or aligned, with respect to the first and second axes, with respect to each other. In addition, the electromagnet coil sets 2910, 2920, 2930 each have upper and lower planar surfaces (e.g., orthogonal to the Z axis), which allows them to be stacked and integrated or embedded into a flat device, such as a board, a wall, the back of a chair, a conformable wearable belt, or other location to minimize patient discomfort.

The controller 2901 is electrically coupled to the first electromagnet coil set 2910, to the second electromagnet coil set 2920, and to the third electromagnet coil set 2930. The controller 2901 is configured to selectively provide power to first electromagnet coil set 2910, to the second electromagnet coil set 2920, and/or to the third electromagnet coil set 2930. Selectively powering the electromagnet coil sets 2910, 2920, and/or 2930 can sequentially produce a total oscillating magnetic field gradient, with respect to each axis, where at least a portion and/or a substantial portion of each total oscillating magnetic field gradient has a monotonically-varying peak magnitude along the respective axis so as to encode a relative position of the 3D magnetic field sensor 110. For example, the electromagnet coil sets 2910, 2920, and/or 2930 can be selectively powered such that at least a portion of the total oscillating magnetic field gradient with respect to the first axis has a monotonically-varying magnitude. In another example, the electromagnet coil sets 2910, 2920, and/or 2930 can be selectively powered such that at least a portion of the total oscillating magnetic field gradient with respect to the second axis has a monotonically-varying magnitude. In yet another example, the electromagnet coil sets 2910, 2920, and/or 2930 can be selectively powered such that at least a portion of the total oscillating magnetic field gradient with respect to the third axis has a monotonically-varying magnitude. The relative position of a magnetic sensor device, with respect to the electromagnet coil sets 2910, 2920, and/or 2930, can be determined by measuring the total oscillating magnetic field while each oscillating localization magnetic field gradients is produced. The portion of the total oscillating magnetic field gradient having a monotonically-varying magnitude with respect to a given axis can be referred to as a field of view (FOV). The total oscillating magnetic field gradient with respect to each axis uniquely encodes the relative position of the 3D magnetic field sensor 110 within the FOV of the 3D magnetic field generator 100.

Figure 30:
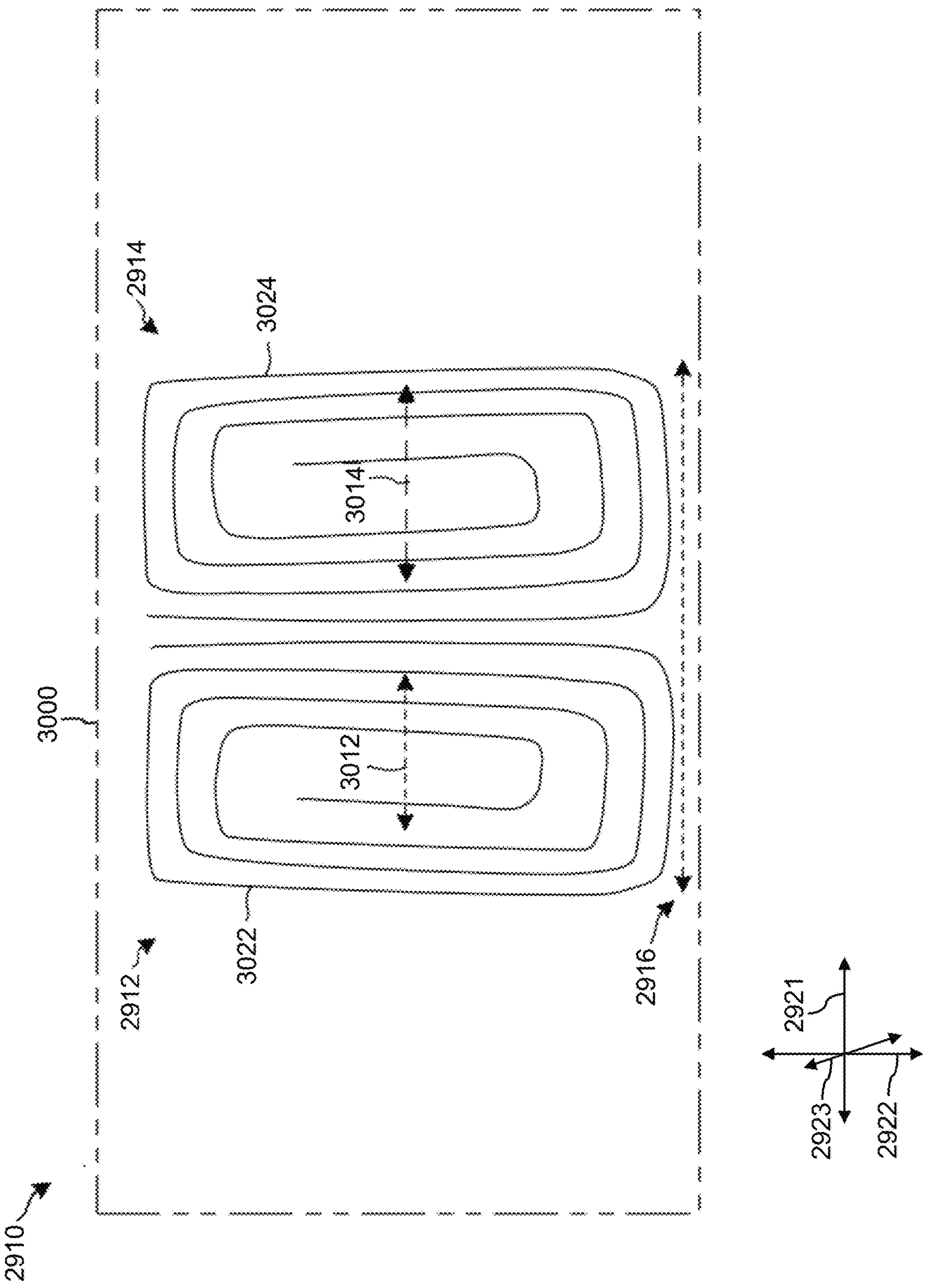
FIG. 30 is a schematic top view of the first electromagnet coil set illustrated in FIG. 29 according to an embodiment.

FIG. 30 is a schematic top view of the first electromagnet coil set 2910 according to an embodiment. The first electromagnet coil set 2910 includes a clockwise spiral winding 2912 and a counterclockwise spiral winding 2914 that are disposed adjacent to or next to each other. The spiral windings 2912, 2914 can be mirror images of each other. Each spiral winding 2912, 2914 has a respective axis of symmetry 3012, 3014 that is parallel to the first axis 2921 (e.g., the X axis). The axes of symmetry 3012, 3014 are aligned in the spiral windings 2912, 2914 to produce a uniform or substantially uniform oscillating magnetic field gradient (e.g., a first oscillating magnetic field gradient) with respect to the first axis 2921. The spiral windings 2912, 2914 are elongated along the second axis 2922 (e.g., the Y axis), such as to form ovals, racetracks (e.g., stadium shapes), rectangles, rounded rectangles, or other elongated shapes. The spiral windings 2912, 2914 can have an elongated length of about 15 cm along the second axis 2922 which can keep the first oscillating magnetic field gradient substantially homogenous across the Y FOV (e.g., the FOV with respect to the second axis 2922). The width 2916 of the first electromagnet coil set 2910 is measured along or parallel to the first axis 2921 (e.g., the X axis). The length of the first electromagnet coil set 2910 is measured along or parallel to the second axis 2922.

The spiral windings 2912, 2914 are formed by respective wires 3022, 3024 (e.g., first and second wires). Alternatively, more than one wire can be connected together to form a spiral winding. The spiral windings 2912, 2914 have a thickness (e.g., a profile) defined by the thickness of the respective wires 3022, 3024. The wires 3022, 3024 can be identical and thus have the same thickness. Thus, the spiral windings 3022, 3024 have top and bottom planar surfaces (or substantially planar surfaces (e.g., at least 95% planar)) that are parallel to an X-Y plane 3000 (e.g., the plane defined by the first and second axes 2921, 2922). The top and bottom planar surfaces of the spiral windings 2912, 2914 are defined by the respective top and bottom surfaces of the wires 3022, 3024. The thickness of the spiral windings 2912, 2914 with respect to the third axis 2923 (e.g., the Z axis) is equal to the thickness of the wires 3022, 3024. The wires 3022, 3024 can have an appropriate number of windings or turns to produce the first oscillating magnetic field gradient.

The wires 3022, 3024 can be configured to receive an AC current in the range of about 10 A to about 50 A including about 20 A, about 30 A, and about 40 A, or another current. For example, the wires 3022, 3024 can be copper wires such as Litz 50/32 AWG wires, which denotes 50 strands of 32 AWG wires bundled together. The wires 3022, 3024 have an insulated covering to prevent electrical shorting therebetween.

Figure 31:
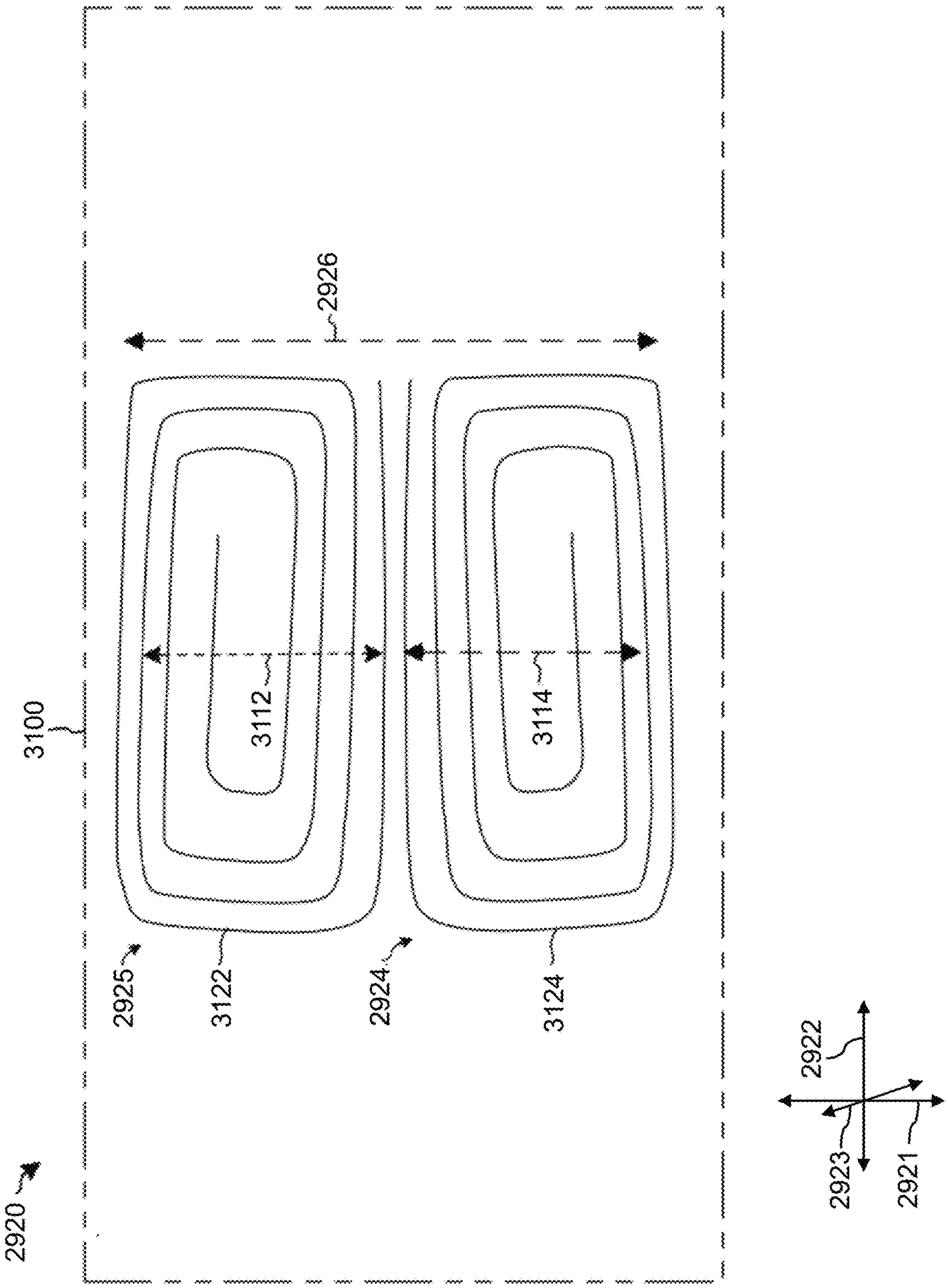
FIG. 31 is a schematic top view of the second electromagnet coil set illustrated in FIG. 29 according to an embodiment.

FIG. 31 is a schematic top view of the second electromagnet coil set 2920 according to an embodiment. The second electromagnet coil set 2920 includes a clockwise spiral winding 2925 and a counterclockwise spiral winding 2924 that are disposed adjacent to or next to each other. The spiral windings 2924, 2925 can be mirror images of each other. Each spiral winding 2924, 2925 has a respective axis of symmetry 3112, 3114 that is parallel to the second axis 2922 (e.g., the Y axis). The axes of symmetry 3112, 3114 are aligned in the spiral windings 2924, 2925 to produce a uniform or substantially uniform oscillating magnetic field gradient (e.g., a second oscillating magnetic field gradient) with respect to the second axis 2922. The second electromagnet coil set 2920 is the same as the first electromagnet coil set 2910 except that the second electromagnet coil set 2920 is rotated by 90 degrees compared to the first electromagnet coil set 2910. In other embodiments, the second electromagnet coil set 2920 can have other configuration differences compared to the first electromagnetic coil set 2910.

The spiral windings 2925, 2924 are formed by respective wires 3122, 3124 (e.g., third and fourth wires). Alternatively, more than one wire can be connected together to form a spiral winding. The spiral windings 2925, 2924 have a thickness (e.g., a profile) defined by the thickness of the respective wires 3122, 3124. The wires 3122, 3124 can be identical and thus have the same thickness. Thus, the spiral windings 2924, 2925 have top and bottom planar surfaces (or substantially planar surfaces (e.g., at least 95% planar))

that are parallel to X-Y plane 3100 (e.g., the plane defined by the first and second axes 2921, 2922). The top and bottom planar surfaces of the spiral windings 2925, 2924 are defined by the respective top and bottom surfaces of the respective wires 3122, 3124. The thickness of the spiral windings 2925, 2924 with respect to the third axis 2923 (e.g., the Z axis) is equal to the thickness of the wires 3122, 3124. The wires 3122, 3124 can have an appropriate number of windings or turns to produce the second oscillating magnetic field gradient. The length 2926 of the second electromagnet coil set 2920 is measured along or parallel to the first axis 2921 (e.g., the X axis). The width of the second electromagnet coil set 2920 is measured along or parallel to the second axis 2922 (e.g., the Y axis).

The wires 3122, 3124 can be configured to receive an AC current in the range of about 10 A to about 50 A including about 20 A, about 30 A, and about 40 A, or another current. For example, the wires 3122, 3124 can be Litz 50/32 AWG wires. The wires 3122, 3124 can be the same as or different than the respective wires 3022, 3024.

Figure 32:
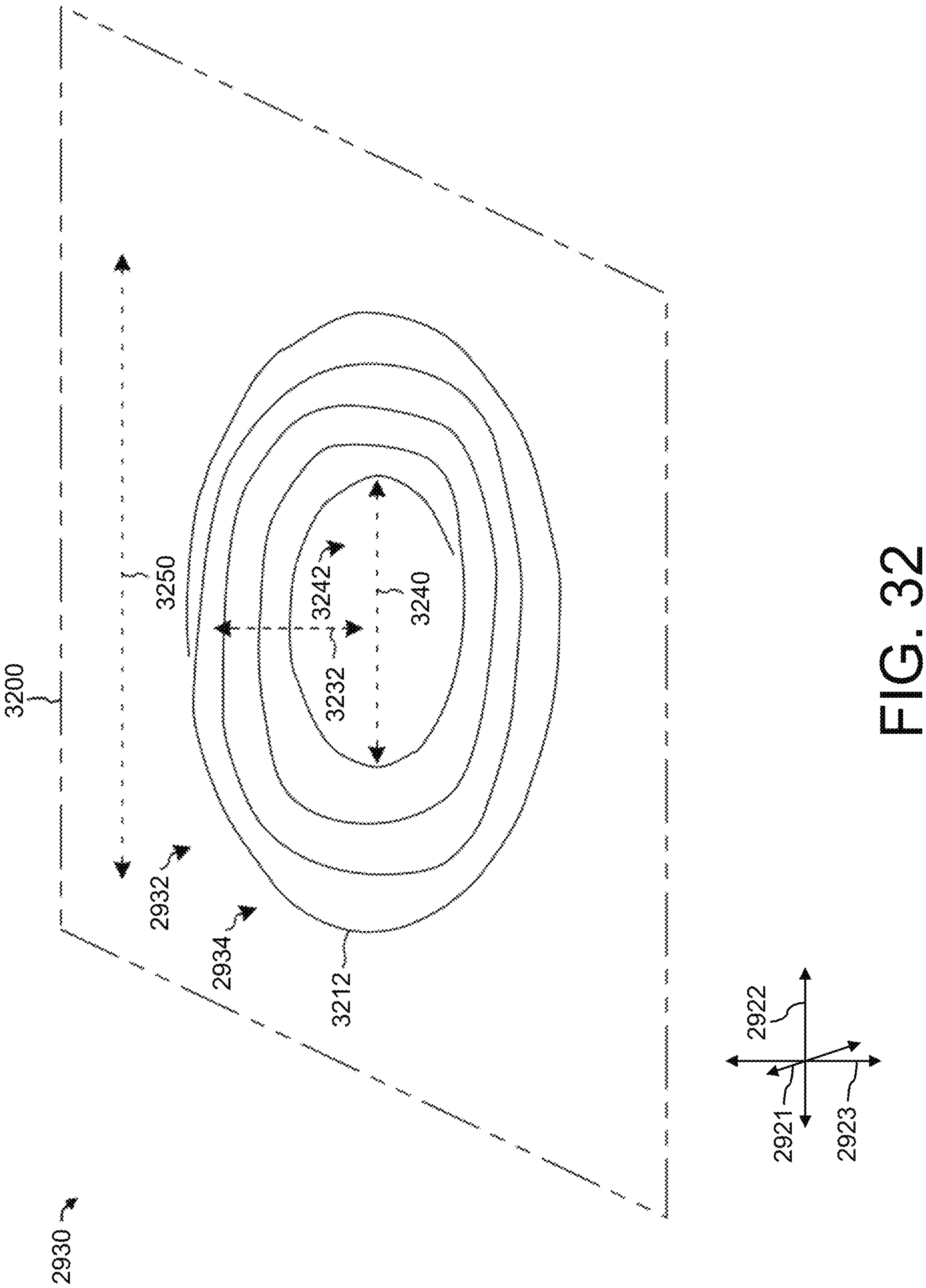
FIG. 32 is a schematic perspective view of the third electromagnet coil set illustrated in FIG. 29 according to an embodiment.

FIG. 32 is a schematic perspective view of the third electromagnet coil set 2930 according to an embodiment. The third electromagnet coil set 2930 includes a spiral winding 2932 that includes one or more wires 3212 that is/are wound in the shape of an annulus, disc, or ring 2934 (in general, annulus). In an embodiment, two or more wires 3212 are wound next to each other to form the annulus 2934. The wire(s) 3212 is/are wound in a counter-clockwise direction but in other embodiments the wire(s) 3212 can be wound in a clockwise direction.

The annulus 2934 has an inner diameter 3240 and an outer diameter 3250, where the inner diameter 3240 defines a hollow region or inner cavity 3242 that does not include the wire(s) 3212. The ratio of the outer diameter 3250 to the inner diameter 3240 can be selected to allow an appropriate number of windings or turns of the wire(s) 3212, to produce the third oscillating magnetic field gradient. In a specific embodiment, the outer diameter 3250 can be about 28 cm and the inner diameter 3240 can be about 10 cm. The wire(s) 3212 can have an insulated covering to prevent electrical shorting therebetween.

The spiral winding 2932 has an axis of symmetry 3232 that is parallel to the third axis 2923 (e.g., the Z axis). The spiral winding 2932 has a thickness (e.g., a profile) defined by the thickness of the wire(s) 3212. Thus, the spiral winding 2932 has top and bottom planar surfaces (or substantially planar surfaces (e.g., at least 95% planar)) that are parallel to the X-Y plane 3200 (e.g., the plane defined by the first and second axes 2921, 2922). The top and bottom planar surfaces of the spiral winding 2932 are defined by the respective top and bottom surfaces of the wire(s) 3212. The thickness of the spiral winding 2932 with respect to the third axis 2923 (e.g., the Z axis) is equal to the thickness of the wire(s) 3212. The wire(s) 3212 can have an appropriate number of windings or turns to produce the third oscillating magnetic field gradient.

The wire(s) 3212 can be configured to receive an AC current in the range of about 10 A to about 50 A including about 20 A, about 30 A, and about 40 A, or another current. For example, the wire(s) 3212 can be Litz 50/32 AWG wires. The wire(s) 3212 can be the same as or different than wires 3022, 3024, 3122, and/or 3124.

Figure 33:
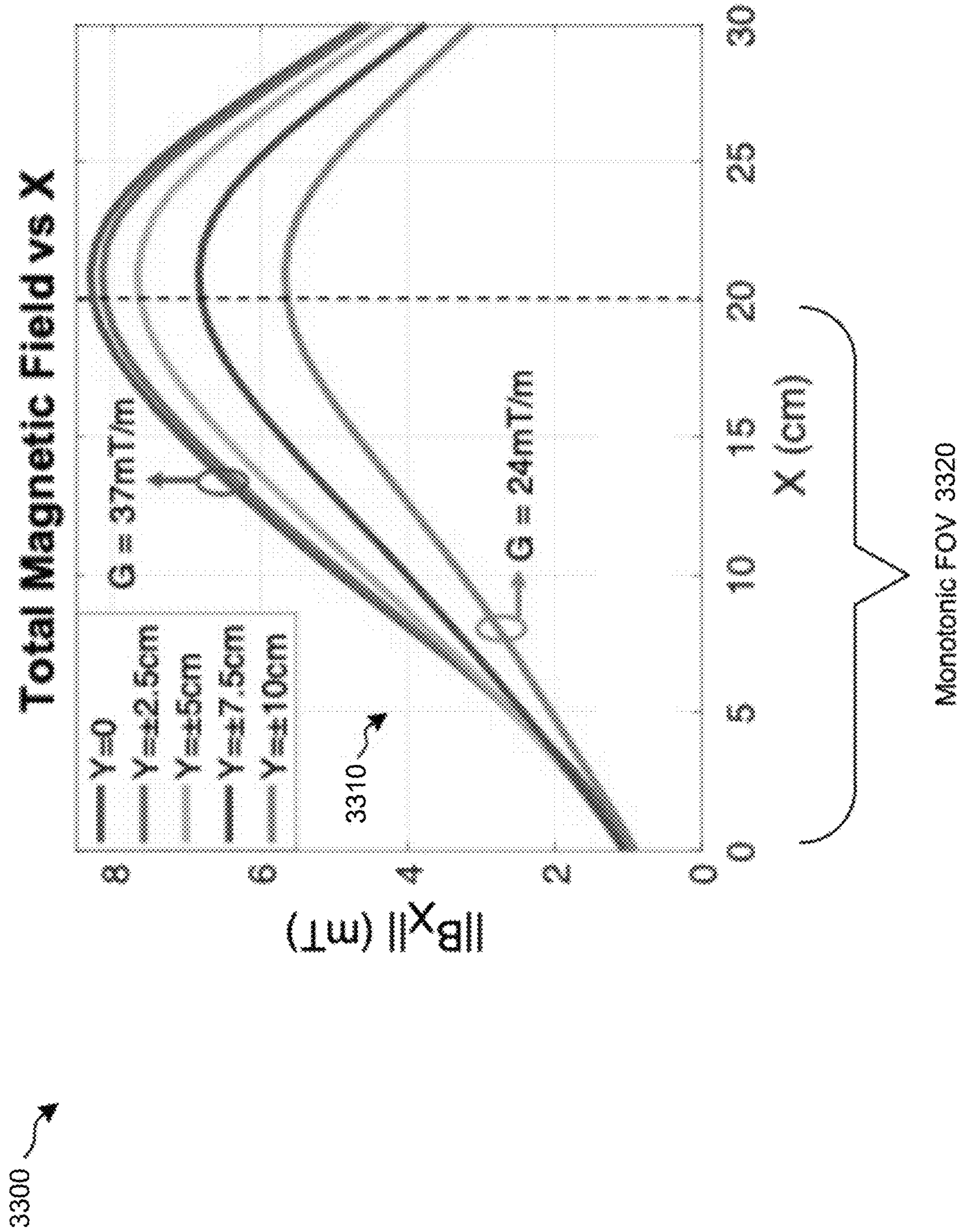
FIG. 33 is a graph that illustrates an example of the total peak magnetic field gradients produced simultaneously by the first and third electromagnet coil sets.

FIG. 33 is a graph 3300 that illustrates an example of the total peak magnetic field gradients 3310 ($\|B_X\|$) produced simultaneously by the first and third electromagnet coil sets 2910, 2930. The graph 3300 illustrates the total peak magnetic fields 3310 (e.g., first peak localization magnetic field gradients) for different Y values from 0 to ±10 cm at ±2.5 cm intervals, while keeping Z=7.5 cm, at various X values. Due to the non-homogenous nature of the Z-coil's magnetic field along the X-axis as the Y-coordinate is varied, the total peak magnetic field gradient strength reduces monotonically from 37 mT/m at Y=0 to 24 mT/m at Y=±10 cm. When operated simultaneously at 30 A of AC power, the first and third electromagnet coil sets 2910, 2930 can have a monotonic X FOV 3320 of about 20 cm in which the magnitude of the total peak magnetic field 3310 varies (increases) monotonically to uniquely encode the relative position with respect to the X axis (e.g., the first axis 2921).

Figure 34:
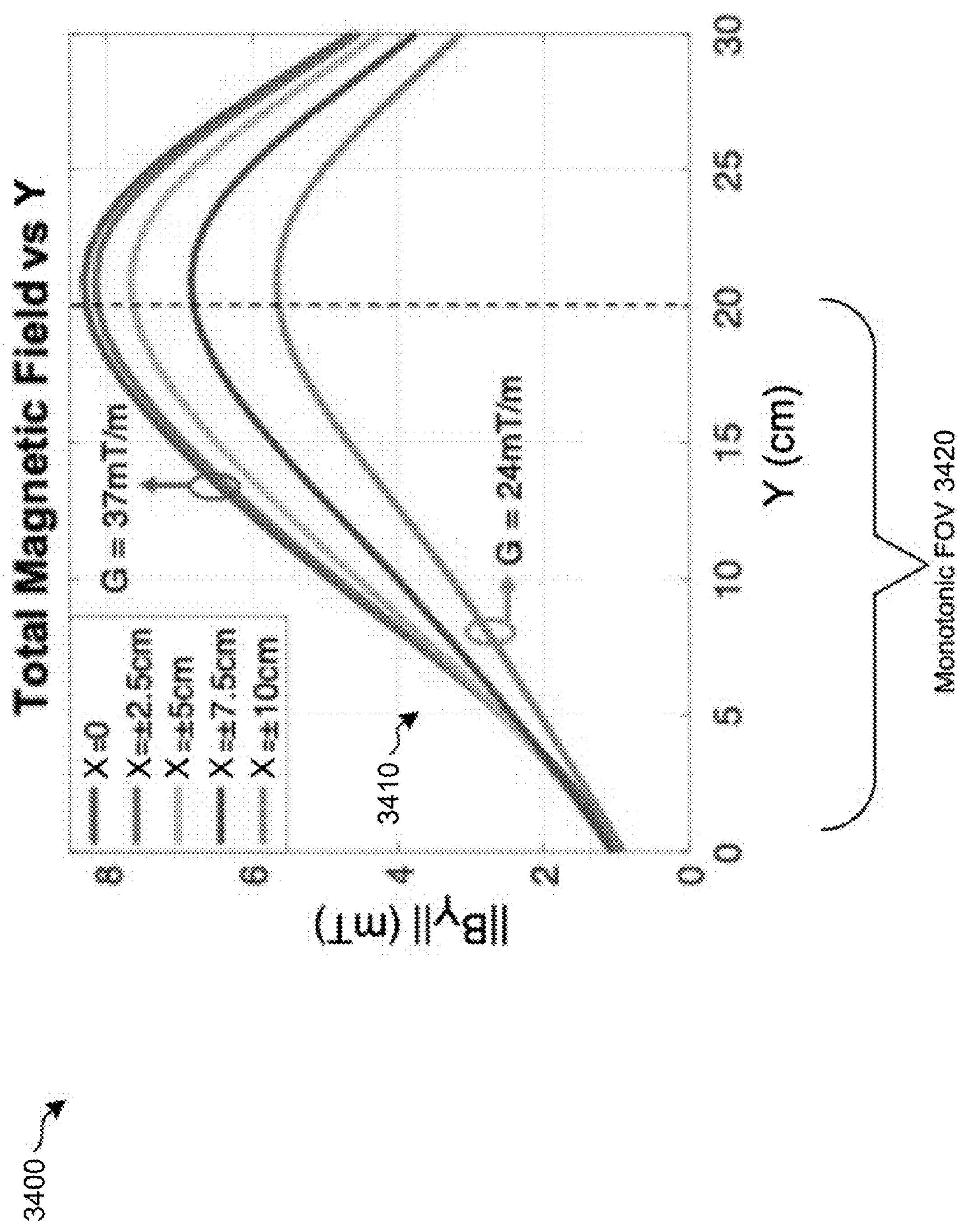
FIG. 34 is a graph that illustrates an example of the total peak magnetic field gradients produced simultaneously by the second and third electromagnet coil sets.

FIG. 34 is a graph 3400 that illustrates an example of the total peak magnetic field gradients 3410 produced simultaneously by the second and third electromagnet coil sets 2920, 2930. The graph 3400 illustrates the total peak magnetic field gradients 3410 (e.g., second peak localization magnetic field gradients) for different X values from 0 to ±10 cm at ±2.5 cm intervals, while keeping Z=7.5 cm, at various Y values. Due to the non-homogenous nature of the Z-coil's magnetic field along the Y-axis as the X-coordinate is varied, the total gradient strength reduces monotonically from 37 mT/m at X=0 to 24 mT/m at X=±10 cm, similar to graph 3300. When operated simultaneously at 30 A of AC power, the second and third electromagnet coil sets 2920, 2930 have a monotonic Y FOV 3420 (e.g., with respect to the second axis 2922) of about 20 cm in which the magnitude of the total peak magnetic field 3410 varies (increases) monotonically to uniquely encode the relative position with respect to the Y axis (e.g., the second axis 2922).

Figure 35:
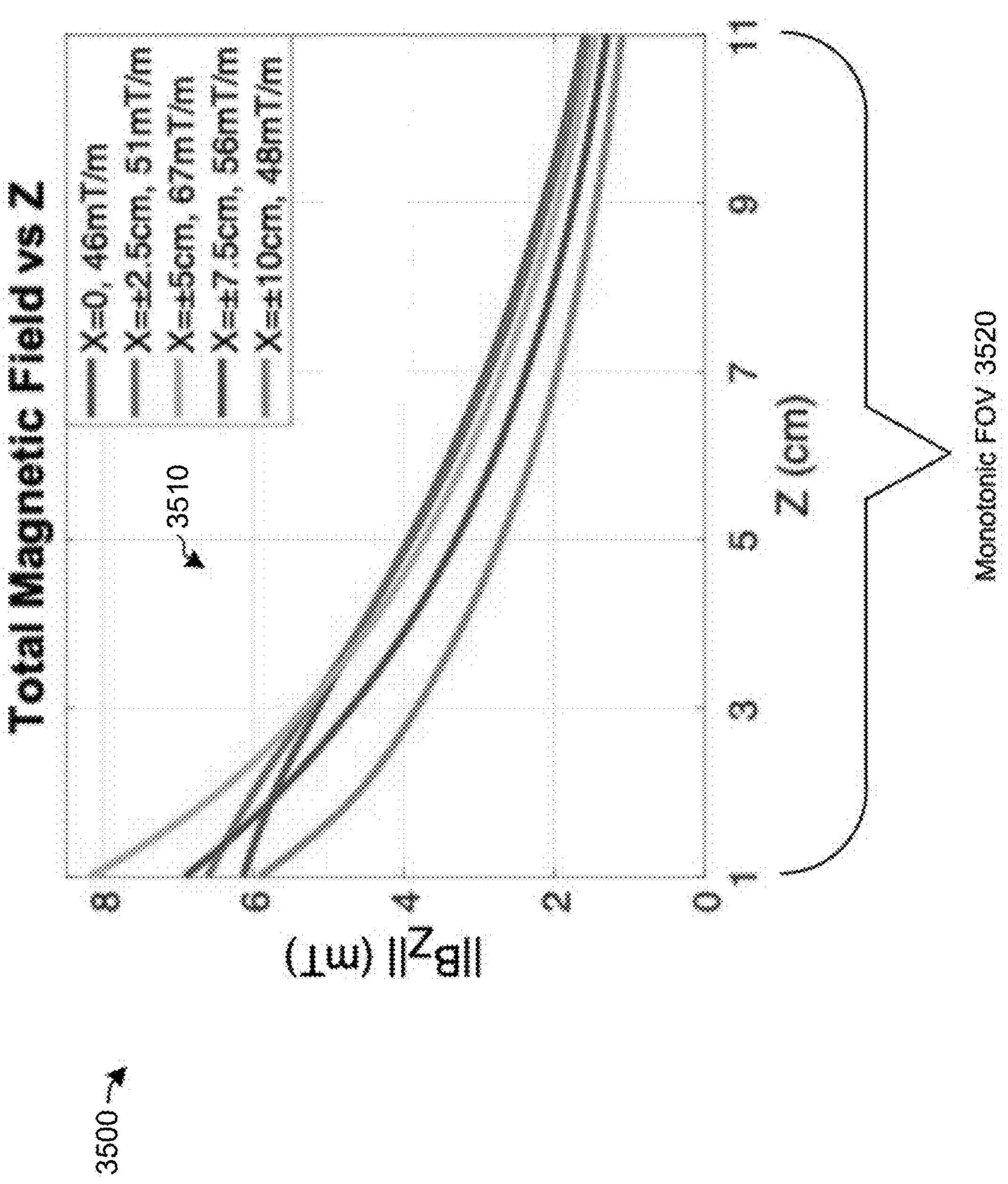
FIG. 35 is a graph that illustrates an example of the monotonically-varying peak magnetic total fields produced by the third electromagnet coil set.

FIG. 35 is a graph 3500 that illustrates an example of the monotonically-varying peak magnetic total fields 3510 ($\|B_Z\|$) produced by the third electromagnet coil set 2930. Each total peak magnetic field 3510 (e.g., third peak localization magnetic field) plot can be measured with a respective relative X position as a function of Z position. Each total peak magnetic field 3510 plot can be measured using a relative Y position of 0 cm. In addition, each total peak magnetic field 3510 can be measured over 10 cm from Z=1 cm to Z=11 cm, where the Z distance is the height from the top surface of the third electromagnet coil set 2930 (e.g., with respect to the third axis 2923).

In general, the magnitude of the total peak magnetic fields 3510 decreases monotonically and with increasing height (Z position) (e.g., with respect to the third axis 2923) from the third electromagnet coil set 2930. In addition, the total magnetic fields 3510 are linear over most heights (Z). It is believed that the inner cavity 3242 enhances the linearity of the total magnetic fields 3510, which is more exponential in the absence of the inner cavity 3242. The third electromagnet coil set 2930 can have a monotonic Z FOV 3520 (e.g., with respect to the third axis 2923) of about 10 cm in which the magnitude of the total peak magnetic field 3510 varies (decreases) monotonically to uniquely encode the relative position with respect to the Z axis (e.g., the third axis 2923).

The gradient strength G is 46 mT/m at X=0 cm, reaches a maximum of 67 mT/m at X=±5 cm, and comes down to 48 mT/m at X=±10 cm, thus ensuring G>30 mT/m over a length of 20 cm along the X-axis. An AC current of 12.5 A can be used in the third electromagnet coil set 1030 to produce the graph 3500, which results in an average magnetic gradient efficiency $\eta$ of 4.3 mT/m/A.

Since the spiral winding 2932 is symmetrical with respect to the X and Y axes, the total peak magnetic fields are the same when measured at a relative X position of 0 cm, at relative Y positions of ±2.5 cm, ±5 cm, ±7.5 cm, and ±10 cm, and from Z=1 cm to Z=11 cm (i.e., where X and Y are switched in graph 3500).

Figure 36:
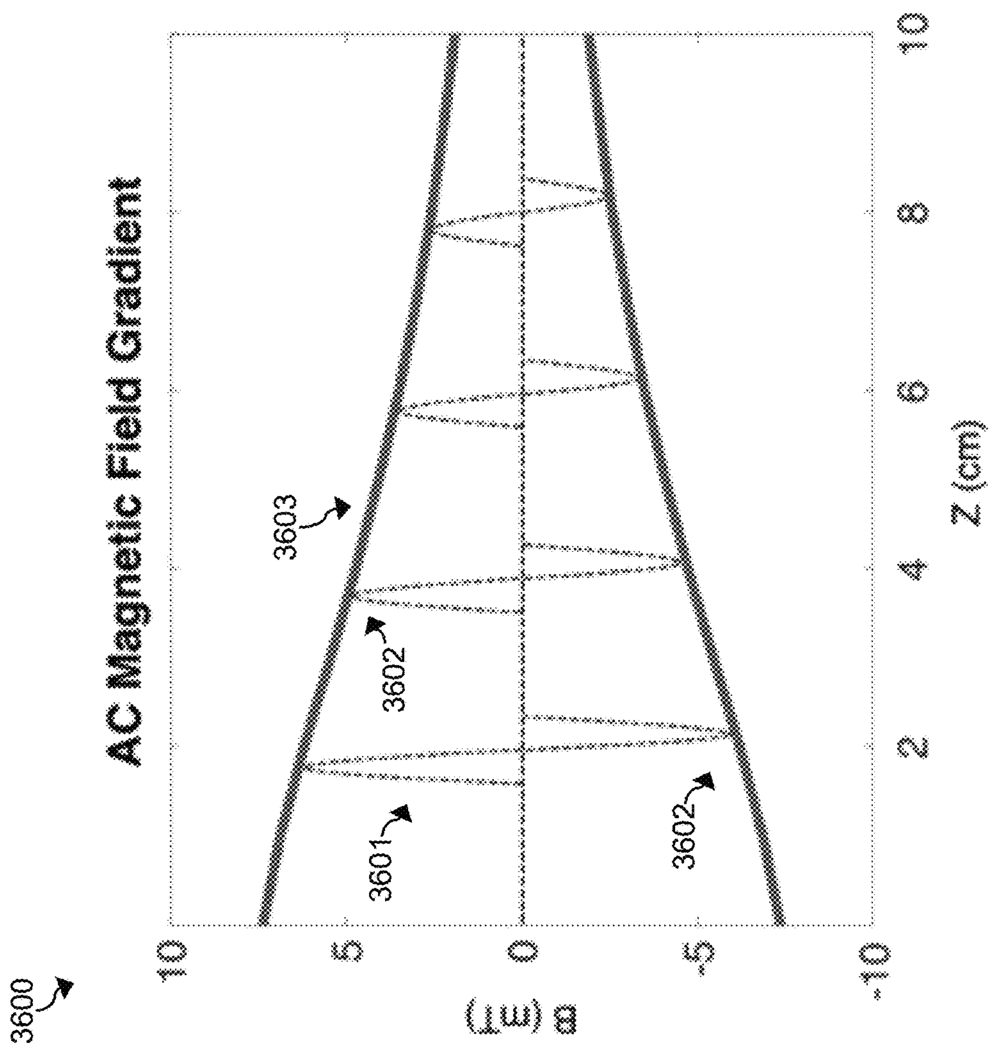
FIG. 36 illustrates an example of an oscillating magnetic field gradient and peak values for a total peak magnetic field gradient in the Z direction.

It is noted that the graphs 3300, 3400, and 3500 illustrate the total peak magnetic fields. Though AC current is used to produce oscillating magnetic fields, only the peak values are used in the graphs 3300, 3400, and 3500. The peak values correspond to the total magnetic fields produced when DC current is used to produce oscillating magnetic fields, for example as disclosed in U.S. Pat. No. 11,457,835, titled "Electromagnet Gradient Coil Apparatus For Micro-Device Localization," which is hereby incorporated by reference. An example of an oscillating magnetic field gradient 3601 and the peak values 3602 for a total peak magnetic field gradient 3603 in the Z direction is illustrated in graph 3600 in FIG. 36.

To perform spatial mapping using the magnetic field measurements by the 3D magnetic field sensor 110, the 500 Hz AC magnetic field were characterized in the FOV of the planar gradient coils of the 3D magnetic field generator 100. However, there were no commercially available sensors that could measure a 500 Hz magnetic field with a resolution of <10 μT while maintaining a 10-15 mT range. This presented a challenge in taking magnetic field measurements of the desired 500 Hz signal using sensors that had too low of an output data rate and would thus alias the frequency content of the oscillating magnetic field. We hypothesized that we could exploit the frequency-independent nature of the peak values of the sinusoidal magnetic field to predict the peak values at 500 Hz without needing to measure a full 500 Hz signal. To accomplish that, magnetic field measurements at lower frequencies were taken to find a scaling or cross-correlation factor that could reliably predict the measurements at the desired frequency of 500 Hz.

An AK09970N sensor was chosen to perform the magnetic field measurements, given its low-noise performance. The sensor was mounted on an automated 3D stage consisting of X, Y and Z linear actuators, positioned above the stacked X, Y and Z gradient coils. Measurements from 0-5 cm in increments of 1 cm were taken. These measurements were performed at several low frequency values ranging 47 Hz to 251 Hz. At each position for a given frequency, 150 measurements were averaged to calculate the peak field magnitude. The peak magnetic field measurements are independent of frequency and the peak field magnitude stays consistent around a mean value (with some standard deviation) for each fixed point along the Z-axis. The margin of error can be attributed to the 10-20 μT of sensor noise. This observation gave us the ability to characterize high-frequency magnetic fields (still under 1 kHz) without needing to actually create the high-frequency signal for characterization purposes. During the actual characterization phase, the sensor was mounted on the automated 3D stage and is moved in the 20×20×10 $cm^3$ of FOV in increments of 1 mm. At each step, magnetic field measurements were made and stored in a look-up table (LUT) for position decoding later.

Figure 38:
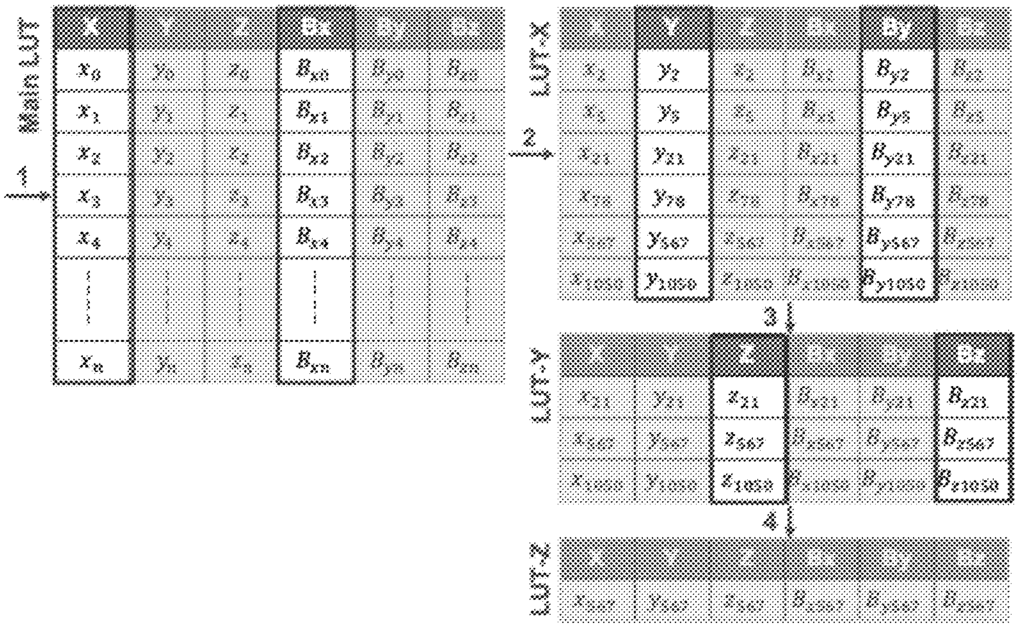
FIG. 38 is a flow chart for an example algorithm to determine the 3D position coordinates that correspond to the measured total peak magnetic field values of the 3D magnetic field sensor.

The LUT can be used to determine the 3D position coordinates that correspond to the measured total peak magnetic field values of the 3D magnetic field sensor 110, for example according to example algorithm 3800 in FIG. 38.

The three magnetic field vectors obtained during the measurements are: (i) Bxx, Bxy, Bxz (measured when X-gradient on), (ii) Byx, Byy, Byz (measured when Y-gradient on), and (iii) Bzx, Bzy, Bzz (measured when Z-gradient on). These nine values can be compared with the values stored in the LUT during the characterization phase and can be used to decode the angular orientation of the 3D magnetic field sensor 110 relative to the known orientation used during characterization. The vrrotvec( ) function in MATLAB was chosen to find the angular transformation between the measured magnetic field vectors and the reference dataset from the LUT. It returns an axis-angle representation of the rotation transformation, which can then be converted into other types such as rotation matrix, Euler angle, or quaternion forms.

Figure 39:
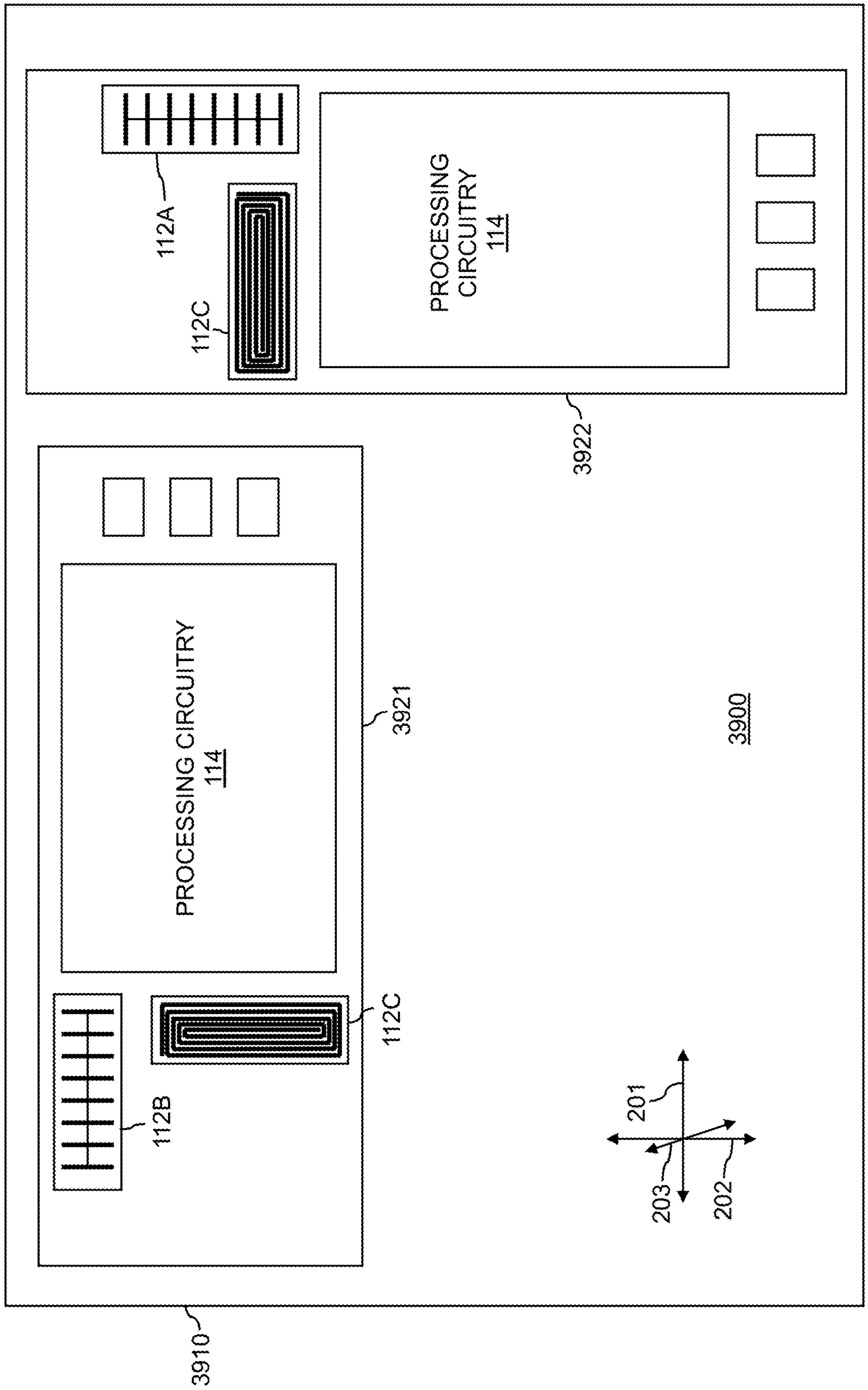
FIG. 39 is a block diagram of a 3D magnetic field sensor according to another embodiment.

FIG. 39 is a block diagram of a 3D magnetic field sensor 3910 according to another embodiment. Sensor 3910 is the same as sensor 110 except that sensor 3910 includes two semiconductor chips 3921, 3922. Semiconductor chips 3921, 3922 are identical except that semiconductor chip 3922 is rotated by 90 degrees with respect to semiconductor chip 3921. The 90-degree rotation causes the second electrically conductive coil 112B in semiconductor chip 3921 to function as a first electrically conductive coil 112A in semiconductor chip 3922. Both semiconductor chips 3921, 3922 include a third electrically conductive coil 112C and processing circuitry 114. The semiconductor chips 3921, 3922 can be mounted on a common substrate or a printed circuit board 3900.

In another embodiment, each electrically conductive coil 112A-C can be formed in a respective/corresponding semiconductor chip.

Figure 40B:
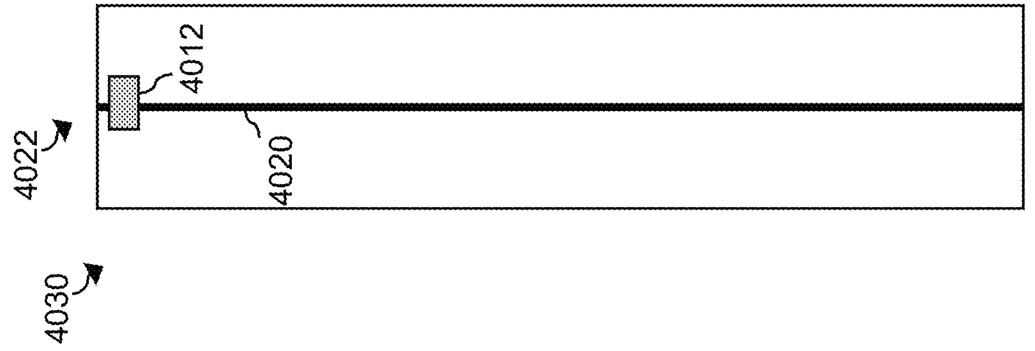
FIG. 40B is a top view of a 3D magnetic field sensor attached to a guidewire in a sheath or cannula.
Figure 40A:
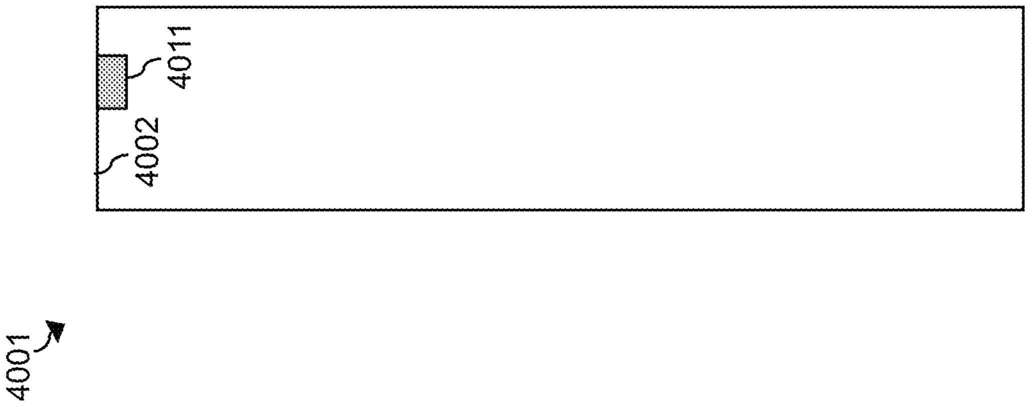
FIG. 40A is a top view of a 3D magnetic field sensor attached to a catheter.

FIG. 40A is a top view of a 3D magnetic field sensor 4011 attached to a catheter 4001. The 3D magnetic field sensor 4011 can be attached to the tip 4002 or to another portion of the catheter 4001 to localize the catheter 4001 (e.g. using a 3D magnetic field generator 100) during positioning such as during a medical procedure. The 3D magnetic field sensor 4011 can be the same as the 3D magnetic field sensor 110 or the 3D magnetic field sensor 3910.

FIG. 40B is a top view of a 3D magnetic field sensor 4012 attached to a guidewire 4020 in a sheath or cannula 4030. The 3D magnetic field sensor 4012 can be attached to the tip 4022 or to another portion of the guidewire 4020 to localize the guidewire 4020 (e.g. using a 3D magnetic field generator 100) during positioning such as during a medical procedure. The 3D magnetic field sensor 4012 can be the same as the 3D magnetic field sensor 110 or the 3D magnetic field sensor 3910.

Figure 41:
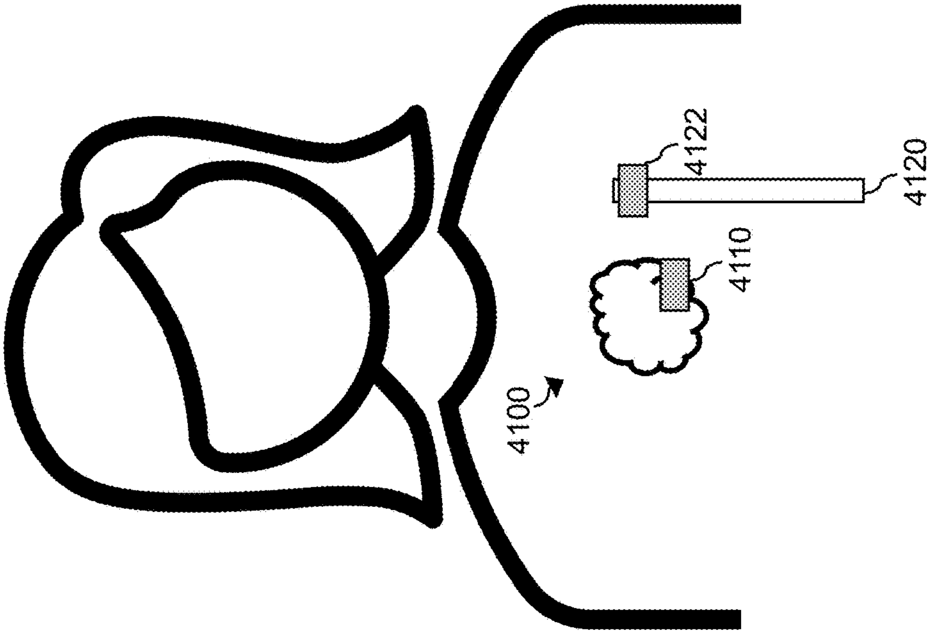
FIG. 41 is a top view of a 3D magnetic field sensor attached to an anatomical feature, such as an organ, of a human or other mammal.

FIG. 41 is a top view of a 3D magnetic field sensor 4110 attached to an anatomical feature, such as an organ 4100, of a human or other mammal. The 3D magnetic field sensor 4110 can be used to localize the anatomical feature (e.g., organ 4100) using a 3D magnetic field generator 100. Additionally or alternatively, the relative position of the anatomical feature with respect to a medical device 4120, such as a catheter (e.g., catheter 4001) and/or a guidewire (e.g., guidewire 4020), that includes a 3D magnetic field sensor 4122 can be determined using the 3D magnetic field sensor 4110 and a 3D magnetic field generator 100. The 3D magnetic field sensor 4110, 4122 can be the same as the 3D magnetic field sensor 110 or the 3D magnetic field sensor 3910.

Figure 42:
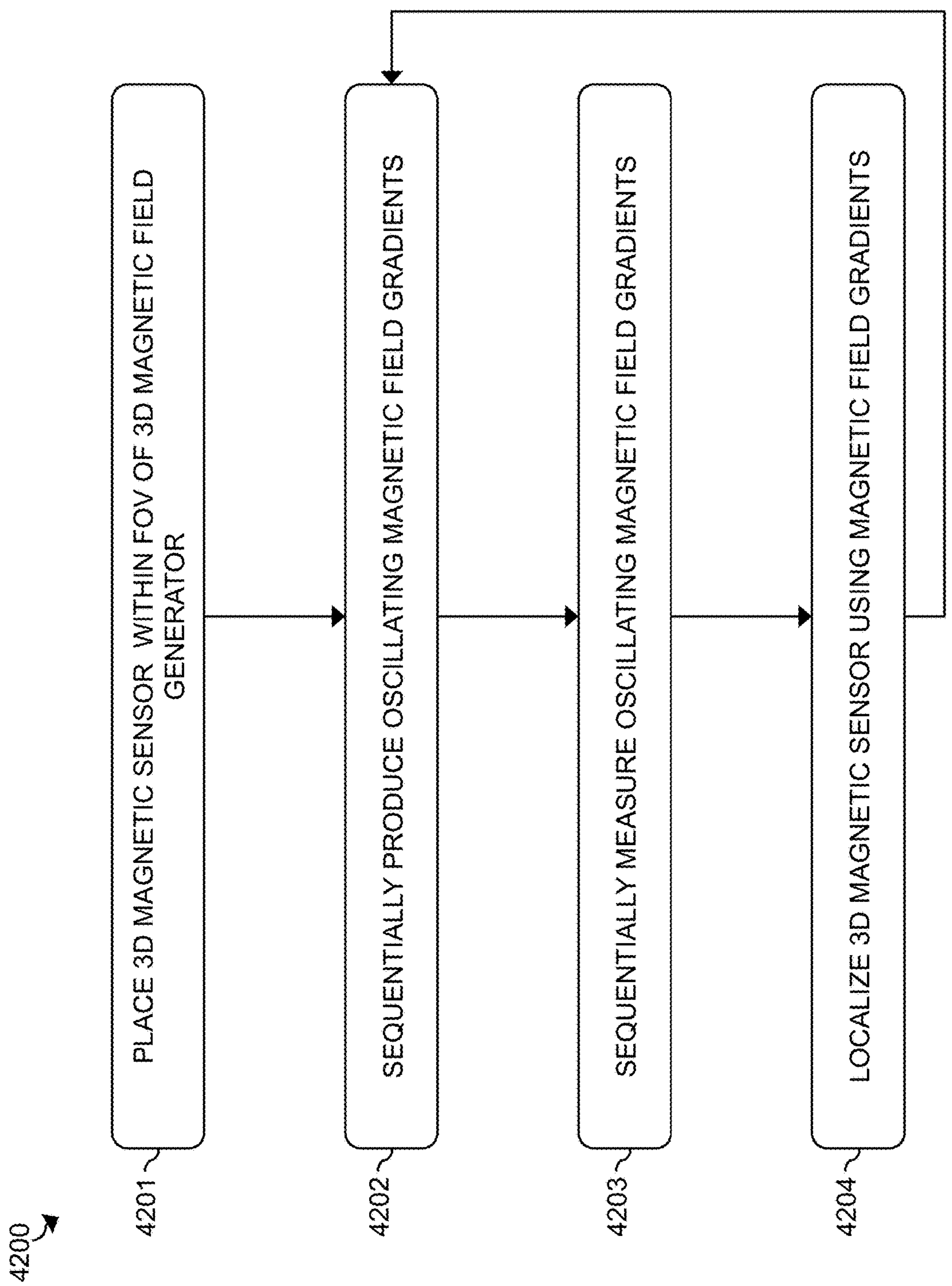
FIG. 42 is a flow chart of a method for 3D localization of an object using oscillating magnetic field gradients according to an embodiment.

FIG. 42 is a flow chart of a method 4200 for 3D localization of an object using oscillating magnetic field gradients according to an embodiment. Method 4200 can be performed using system 10.

In step 4201, a 3D magnetic field sensor is placed within a FOV of a 3D magnetic field generator. The 3D magnetic field sensor is configured to sense oscillating magnetic fields and to determine the peak values or magnitudes of the oscillating magnetic fields. The 3D magnetic field sensor can be the same as 3D magnetic field sensor 110, 3910, 4110, and/or 4122. The 3D magnetic field generator can be the same as the 3D magnetic field generator 100.

In step 4202, the 3D magnetic field generator sequentially produces oscillating magnetic field gradients with respect to three orthogonal axes, such as with respect to axes 2921-2923. At least a portion of each oscillating magnetic field gradient has a monotonically-varying peak magnetic field magnitude along a respective axis, which corresponds to the FOV of each axis. Examples of the FOV of each axis include the monotonic X FOV 3320, the monotonic Y FOV 3420, and the monotonic Z FOV 3520.

In step 4203, the 3D magnetic field sensor (e.g., using a respective electrically conductive coil 112) sequentially measures respective peak voltages that corresponds to the monotonically-varying peak magnetic field magnitude of each oscillating magnetic field gradient. For example, a first peak voltage corresponds to the monotonically-varying peak magnetic field magnitude of the first oscillating magnetic field gradient, a second peak voltage corresponds to the monotonically-varying peak magnetic field magnitude of the second oscillating magnetic field gradient, and a third peak voltage corresponds to the monotonically-varying peak magnetic field magnitude of the third oscillating magnetic field gradient.

In step 4204, the relative position of the 3D magnetic field sensor, with respect to the 3D magnetic field generator, is determined using the respective peak voltages. The relative position can determined using a look-up table, a model, such as a trained machine learning model, and/or an algorithm (e.g., algorithm 3800) to determine the relative position of the 3D magnetic field sensor with respect to the FOV of the 3D magnetic field generator.

In some embodiments, the 3D magnetic field sensor can take multiple samples/measurements of each oscillating magnetic field gradient to determine a statistic (e.g., average or median) of the respective peak voltages to improve accuracy.

The 3D magnetic field sensor can determine its relative position using circuitry on and/or program instructions stored in the 3D magnetic field sensor. Additionally or alternatively, the 3D magnetic field sensor can transmit the respective peak voltages to an external device (e.g., a computer such as a laptop, a desktop, a tablet, a smartphone, or another computer) using communication circuitry on the 3D magnetic field sensor, such as through Bluetooth, WiFi, NFC, cellular, backscattering, and/or other communications standards or protocols. The external device can then use the peak voltages to determine the relative position of the 3D magnetic field sensor with respect to the FOV of the 3D magnetic field generator. For example the external device (or the 3D magnetic field sensor) can a look-up table, a model, such as a trained machine learning model, and/or an algorithm (e.g., algorithm 3800) to determine the relative position of the 3D magnetic field sensor with respect to the FOV of the 3D magnetic field generator. The relative position of the 3D magnetic field sensor can be graphically displayed, such as on a monitor or display screen coupled to the external device.

In some embodiments, steps 4202-4024 can be repeated while the object is within the FOV of the 3D magnetic field generator to continuously determine the relative position of the 3D magnetic field sensor with respect to the FOV of the 3D magnetic field generator.

In some embodiments, the method 4200 can be performed while the 3D magnetic field sensor is attached and/or mechanically coupled to an object to determine the relative position of the object or a specific portion of an object to which the magnetic field sensor is attached. The object can be a medical device (e.g., a catheter 4001 or a guidewire 4020), an anatomical feature (e.g., an organ 4100) of a mammal, or another object.

In some embodiments, the method 4200 can be performed while a first 3D magnetic field sensor is attached to a first object and a second 3D magnetic field sensor is attached to a second object to determine the relative position of the first object (e.g., of the first magnetic sensor) with respect to the 3D magnetic field generator), the relative position of the second object (e.g., of the second magnetic sensor) with respect to the 3D magnetic field generator, and/or the relative position of the first object (e.g., of the first magnetic sensor) with respect to the second object (e.g., of the second magnetic sensor), for example as illustrated in FIG. 41.

The invention should not be considered limited to the particular embodiments described above. Various modifications, equivalent processes, as well as numerous structures to which the invention may be applicable, will be readily apparent to those skilled in the art to which the invention is directed upon review of this disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of this application need not reside on a single computer or processor but may be distributed in a modular fashion among a number of different computers or processors to implement various aspects of this application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the disclosure and claims include new and novel improvements to existing methods and technologies, which were not previously known nor implemented to achieve the useful results described above. Users of the method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A three-dimensional on-chip magnetic sensor comprising:

a semiconductor chip having a semiconductor substrate;

a plurality of metal layers disposed on the semiconductor substrate;

a plurality of insulator layers disposed on the semiconductor substrate, each insulator layer disposed between a pair of neighboring metal layers to form an alternating arrangement of metal layers and insulator layers;

a plurality of metal vias defined in the insulator layers, each metal via electrically connecting a respective pair of neighboring metal layers; and a first electrically conductive coil having a plurality of first planar spirals formed by the metal layers and the metal vias, each first planar spiral including a plurality of first interconnected loops wound about a first axis, wherein neighboring first planar spirals are electrically connected to each other;

a second electrically conductive coil having a plurality of second planar spirals formed by the metal layers and the metal vias, each second planar spiral including a plurality of second interconnected loops wound about a second axis that is orthogonal to the first axis, wherein neighboring second planar spirals are electrically connected to each other;

a third electrically conductive coil having a third planar spiral formed by at least some of the metal layers and at least some of the metal vias, the third planar spiral including a plurality of third interconnected loops that are wound about a third axis that is orthogonal to the first and second axes, the metal layers spaced apart along the third axis; and a respective readout circuit electrically coupled to a respective electrically conductive coil, the respective readout circuit disposed in the semiconductor chip, wherein:

each electrically conductive coil is configured to produce a respective electromagnetic force (EMF) induced by an oscillating magnetic field produced by an external magnetic field generator, the respective EMF exclusively driving a respective alternating current (AC) through the respective readout circuit, and each readout circuit is configured to detect a respective peak voltage magnitude of the respective AC driven exclusively by the respective EMF.

2. The three-dimensional on-chip magnetic sensor of claim 1, wherein the respective readout circuit comprises:

a respective amplifier and filter circuit electrically coupled having an input coupled to the respective electrically conductive coil;

a respective peak-detect-and-hold (PDH) circuit having an input coupled to an output of the respective amplifier and filter circuit; and a respective analog-to-digital converter (ADC) having an input coupled to an output of the respective peak-detect-and-hold circuit.

3. The three-dimensional on-chip magnetic sensor of claim 2, wherein the respective amplifier and filter circuit includes a band-pass filter having an output coupled to an input of a programmable gain amplifier.

4. The three-dimensional on-chip magnetic sensor of claim 2, wherein the respective PDH circuit includes a respective positive differential PDH circuit and a respective negative differential PDH.

5. The three-dimensional on-chip magnetic sensor of claim 2, wherein the respective ADC comprises a respective differential-input successive approximation register (SAR) ADC.

6. A catheter attached to the three-dimensional on-chip magnetic sensor of claim 1.

7. A guidewire attached to the three-dimensional on-chip magnetic sensor of claim 1.

8. A system for three-dimensional (3D) localization using oscillating magnetic field gradients, comprising:

a 3D magnetic field gradient generator comprising:

a first planar electromagnet coil set configured to produce a first oscillating magnetic field gradient with respect to a first axis;

a second planar electromagnet coil set configured to produce a second oscillating magnetic field gradient with respect to a second axis that is orthogonal to the first axis;

a third planar electromagnet coil set configured to produce a third oscillating magnetic field gradient with respect to a third axis that is orthogonal to the first and second axes, the first, second, and third planar electromagnet coil sets vertically arranged with respect to the third axis; and a controller configured to selectively provide alternating-current (AC) power to the first planar electromagnet coil set, to the second planar electromagnet coil set, and/or to the third planar electromagnet coil set to sequentially produce a respective oscillating localization magnetic field gradient with respect to each of the first, second, and third axes, at least a portion of each oscillating localization magnetic field gradient having a monotonically-varying peak magnetic field magnitude along a respective axis that uniquely encodes a relative position along a respective axis; and a 3D on-chip magnetic sensor comprising:

a semiconductor chip having a semiconductor substrate;

a plurality of metal layers disposed on the semiconductor substrate;

a plurality of insulator layers disposed on the semiconductor substrate, each insulator layer disposed between a pair of neighboring metal layers to form an alternating arrangement of metal layers and insulator layers;

a plurality of metal vias defined in the insulator layers, each metal via electrically connecting a respective pair of neighboring metal layers;

a first electrically conductive coil having a plurality of first planar spirals formed by the metal layers and the metal vias, each first planar spiral including a plurality of first interconnected loops wound about a first chip axis, wherein neighboring first planar spirals are electrically connected to each other;

a second electrically conductive coil having a plurality of second planar spirals formed by the metal layers and the metal vias, each second planar spiral including a plurality of second interconnected loops wound about a second chip axis that is orthogonal to the first chip axis, wherein neighboring second planar spirals are electrically connected to each other;

a third electrically conductive coil having a third planar spiral formed by at least some of the metal layers and at least some of the metal vias, the third planar spiral including a plurality of third interconnected loops that are wound about a third chip axis that is orthogonal to the first and second chip axes, the metal layers spaced apart along the third chip axis; and a respective readout circuit electrically coupled to a respective electrically conductive coil, the respective readout circuit disposed in the semiconductor chip, wherein:

each electrically conductive coil is configured to produce a respective electromagnetic force (EMF) induced by each oscillating localization magnetic field gradient produced by the 3D magnetic field gradient generator, the respective EMF exclusively driving a respective sensor AC through the respective readout circuit, and each readout circuit is configured to detect a respective peak voltage magnitude of the respective sensor AC driven exclusively by the respective EME, the respective peak voltage magnitude corresponding to the monotonically-varying peak magnetic field magnitude of each oscillating localization magnetic field gradient produced by the 3D magnetic field gradient generator.

9. The system of claim 8, wherein:

the controller is configured to provide AC power simultaneously to only the first and third planar electromagnet coil sets to thereby produce a first oscillating localization magnetic field gradient with respect to the first axis, the controller is configured to provide AC power simultaneously to only the second and third planar electromagnet coil sets to thereby produce a second oscillating localization magnetic field gradient with respect to the second axis, and the controller is configured to provide AC power to only the third planar electromagnet coil set to thereby produce a third oscillating localization magnetic field gradient with respect to the third axis.

10. The system of claim 8, wherein:

the first planar spirals are spatially offset from each other along the first chip axis, and the second planar spirals are spatially offset from each other along the second chip axis.

11. The system of claim 8, wherein each first interconnected loop and each second interconnected loop includes a respective pair of metal wires disposed in respective metal layers, a respective intra-loop column that electrically connects the respective pair of metal wires of a respective interconnected loop, and a respective inter-loop column that electrically connects one of the metal wires of the respective interconnected loop to one of the metal wires in a subsequent interconnected loop.

12. The system of claim 8, wherein the at least some of the metal layers and the at least some of the metal vias form a continuous metal structure, with respect to the third chip axis, along a length of the third planar spiral.

13. The system of claim 8, wherein the respective readout circuit comprises:

a respective amplifier and filter circuit electrically coupled having an input coupled to the respective electrically conductive coil;

a respective peak-detect-and-hold (PDH) circuit having an input coupled to an output of the respective amplifier and filter circuit; and a respective analog-to-digital converter (ADC) having an input coupled to an output of the respective peak-detect-and-hold circuit.

14. The system of claim 13, wherein the respective amplifier and filter circuit includes a band-pass filter having an output coupled to an input of a programmable gain amplifier.

15. The system of claim 13, wherein the respective PDH circuit includes a respective positive differential PDH circuit and a respective negative differential PDH.

16. The system of claim 13, wherein the respective ADC comprises a respective differential-input successive approximation register (SAR) ADC.

17. The system of claim 8, further comprising a catheter, the 3D on-chip magnetic sensor attached to the catheter.

18. The system of claim 8, further comprising a guidewire, the 3D on-chip magnetic sensor attached to the guidewire.

19. A method of three-dimensional (3D) localization, comprising:

placing a 3D magnetic sensor within a field of view (FOV) of a 3D magnetic field gradient generator, the 3D magnetic sensor including first, second, and third electrically conductive coils and first, second, and third readout circuits, each readout circuit electrically coupled to a respective electrically conductive coil;

sequentially producing, with the 3D magnetic field gradient generator, first, second, and third oscillating localization magnetic field gradients with respect to first, second, and third axes, respectively, the first, second, and third axes mutually orthogonal to one another, wherein the FOV corresponds to at least a portion of each oscillating localization magnetic field gradient having a monotonically-varying peak magnitude along a respective axis;

sequentially inducing first, second, and third electromagnetic forces (EMFs) in each of the first, second, and third electrically conductive coils in the 3D magnetic sensor, the first, second, and third EMFs induced exclusively by the first, second, and third oscillating localization magnetic field gradients, respectively, sequentially produced by the 3D magnetic field generator;

sequentially exclusively driving, with each of the first, second, and third EMFs in each of the first, second, and third electrically conductive coils, a respective alternating current (AC) through each readout circuit;

sequentially measuring, with each readout circuit, a respective peak voltage magnitude of each AC driven by each of the first, second, and third EMFs, the respective peak voltage magnitude of each AC driven by each of the first, second, and third EMFs corresponding to the monotonically-varying peak magnitude of each oscillating localization magnetic field gradient; and determining a relative position of the 3D magnetic sensor, with respect to the 3D magnetic field gradient generator, using the respective peak voltage magnitude of each AC driven by each of the first, second, and third EMFs.

20. The method of claim 19, further comprising attaching and/or mechanically coupling the 3D magnetic sensor to an object, whereby the relative position of the 3D magnetic sensor corresponds to a relative position of the object.

* * * * *